(12) United States Patent
Humphreys et al.

(10) Patent No.: US 9,970,935 B2
(45) Date of Patent: May 15, 2018

(54) USES OF GLI1 IN DETECTING TISSUE FIBROSIS

(71) Applicant: THE BRIGHAM AND WOMEN'S HOSPITAL, INC., Boston, MA (US)

(72) Inventors: Benjamin D. Humphreys, Brookline, MA (US); Rafael Kramann, Lemiers (NL); Derek Dirocco, Brookline, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days. days.

(21) Appl. No.: 15/116,722

(22) PCT Filed: Feb. 6, 2015

(86) PCT No.: PCT/US2015/014796
§ 371 (c)(1),
(2) Date: Aug. 4, 2016

(87) PCT Pub. No.: WO2015/120257
PCT Pub. Date: Aug. 13, 2015

(65) Prior Publication Data
US 2016/0341726 A1 Nov. 24, 2016

Related U.S. Application Data

(60) Provisional application No. 61/936,783, filed on Feb. 6, 2014, provisional application No. 62/011,259, filed on Jun. 12, 2014.

(51) Int. Cl.
| | | |
|---|---|---|
| *G01N 33/50* | (2006.01) | |
| *G01N 33/569* | (2006.01) | |
| *C12N 5/0775* | (2010.01) | |
| *G01N 33/68* | (2006.01) | |
| *A61K 38/06* | (2006.01) | |

(52) U.S. Cl.
CPC ..... *G01N 33/56966* (2013.01); *A61K 38/063* (2013.01); *C12N 5/0668* (2013.01); *G01N 33/5023* (2013.01); *G01N 33/6887* (2013.01); *G01N 2333/4703* (2013.01); *G01N 2333/4712* (2013.01); *G01N 2800/085* (2013.01); *G01N 2800/347* (2013.01)

(58) Field of Classification Search
None
See application file for complete search history.

(56) References Cited

U.S. PATENT DOCUMENTS

| | | | | |
|---|---|---|---|---|
| 2011/0183948 A1* | 7/2011 | Levine | ............... | C07D 491/048 514/171 |
| 2011/0183962 A1* | 7/2011 | Dorsch | ................ | A61K 31/167 514/211.08 |
| 2012/0010230 A1 | 1/2012 | MacDougall et al. | | |

FOREIGN PATENT DOCUMENTS

WO    2013/148232 A1    10/2013

OTHER PUBLICATIONS

Mason et al., PLoS One. 2011;6(11):e27699. doi: 10.1371/journal.pone.0027699.*
Bansal et al., "Darinaparsin Inhibits Prostate Tumor Initiating Cells and Du145 Xenografts and Is an Inhibitor of Hedgehog Signaling", Mol. Cancer Ther. 14(1):23-30 (2014).
Beauchamp et al., "Arsenic trioxide inhibits human cancer cell growth and tumor development in mice by blocking Hedgehog/GLI pathway", The Journal of Clinical Investigation 121(1):148-160 (2011).
Cigna et al., "The Hedgehog System Machinery Controls Transforming Growth Factor-β-Dependent Myofibroblastic Differentiation in Humans: Involvement in Idiopathic Pulmonary Fibrosis", The American Journal of Pathology 181 (6):2126-2137 (2012).
Crisan et al., "A Perivascular Origin for Mesenchymal Stem Cells in Multiple Human Organs", Cell Stem Cell 3:301-313 (2008).
Crisan et al., "Perivascular Multipotent Progenitor Cells in Human Organs", Ann. N.Y. Acad. Sci. 1176:118-123 (2009).
Ding et al., "Sonic Hedgehog Signaling Mediates Epithelial-Mesenchymal Communication and Promotes Renal Fibrosis", J. Am. Soc. Nephrol. 23:801-813 (2012).
Dirocco et al., "Wnt4/β-Catenin Signaling in Medullary Kidney Myofibroblasts", J. Am. Soc. Nephrol. 24:1399-1412 (2013).
Dominici et al., "Minimal criteria for defining multipotent mesenchymal stromal cells. The International Society for Cellular Therapy position statement", Cytotherapy 8(4):315-317 (2006).
Fabian et al., "Hedgehog-Gli Pathway Activation during Kidney Fibrosis", The American Journal of Pathology 180 (4):1441-1453 (2012).
Horwitz et al., "Clarification of the nomenclature for MSC: The International Society for Cellular Therapy position statement", Cytotherapy 7(5):393-395 (2005).
Humphreys et al., "Fate Tracing Reveals the Pericyte and Not Epithelial Origin of Myofibroblasts in Kidney Fibrosis", The American Journal of Pathology 176(1):85-97 (2010).
Humphreys et al., "Lineage-tracing methods and the kidney", Kidney International 86:481-488 (2013).
Kim et al., "Arsenic antagonizes the Hedgehog pathway by preventing ciliary accumulation and reducing stability of the Gli2 transcriptional effector", PNAS 107(30):13432-13437 (2010).
Kramann et al., "Fluorescence Microangiography for Quantitative Assessment of Peritubular Capillary Changes after AKI in Mice", J. Am. Soc. Nephrol. 25:1924-1931 (2014).
Kramann et al., "Matrix Producing Cells in Chronic Kidney Disease: Origin, Regulation, and Activation", Curr. Pathobiol. Rep. 1(4): (2013).

(Continued)

*Primary Examiner* — Daniel C Gamett
(74) *Attorney, Agent, or Firm* — David S. Resnick; Teresa A. Ptashka; Nixon Peabody LLP

(57) ABSTRACT

Methods are provided herein for the use of Gli-1 as a specific marker for myofibroblast progenitor cells, thereby permitting the diagnosis of early stages of fibrosis prior to the onset of organ failure. Also provided herein are methods of isolating Gli-1+ cells for e.g., use in high-throughput screening of compounds for the treatment or prevention of fibrosis. In another aspect, provided herein are methods of treating or preventing fibrosis (e.g., kidney fibrosis) in a subject by administering a Gli inhibitor, particularly a Gli-2 inhibitor or a Gli-1/Gli-2 inhibitor.

7 Claims, 43 Drawing Sheets

(56) References Cited

OTHER PUBLICATIONS

Kramann et al., "Perivascular Gli1+ progenitors are key contributors to injury-induced organ fibrosis", Cell Stem Cell 16(1):51-66 (2015).

Lauth et al., "Inhibition of GLI-mediated transcription and tumor cell growth by small-molecule antagonists", PNAS 104(20):8455-8460 (2007).

Lebleu et al., "Origin and Function of Myofibroblasts in Kidney Fibrosis", Nat. Med. 19(8):1047-1053 (2013).

Lin et al., "Pericytes and Perivascular Fibroblasts are the Primary Source of Collagen-Producing Cells in Obstructive Fibrosis of the Kidney", The American Journal of Pathology 173(6):1617-1627 (2008).

Matise et al., "Gli2 is required for induction of floor plate and adjacent cells, but not most ventral neurons in the mouse central nervous system", Development 125:2759-2770 (1998).

Otranto et al., "The role of the myofibroblast in tumor stroma remodeling", Cell Adhesion and Migration 6 (3):203-219 (2012).

Park et al., "Mouse Gli1 mutants are viable but have defects in SHH signaling in combination with a Gli2 mutation", Development 127:1593-1605 (2000).

Plaisant et al., "Inhibition of Hedgehog Signaling Decreases Proliferation and Clonogenicity of Human Mesenchymal Stem Cells", PLoS One 6(2):e16798 (2011).

Zhao et al., "Secretion of Shh by a neurovascular bundle niche supports mesenchymal stem cell homeostasis in the adult mouse incisor", Cell Stem Cell 14(2):160-173 (2014).

Castella et al., "Regulation of myofibroblast activities: Calcium pulls some strings behind the scene", Exp Cell Res 316(15), 2390-2401, 2010.

Hinz, "The myofibroblast: Paradigm for a mechanically active cell", J Biomech 43(1), 146-155, 2010.

Kelley et al., "A Population of Selected Renal Cells Augments Renal Function and Extends Survival in the ZSF1 Model of Progressive Diabetic Nephropathy", Cell Transplantation 22(6), 1023-1039, 2013.

Kramann et al., "Understanding the origin, activation and regulation of matrix-producing myofibroblasts for treatment of fibrotic disease", J Pathol 231(3), 273-289, 2013.

\* cited by examiner

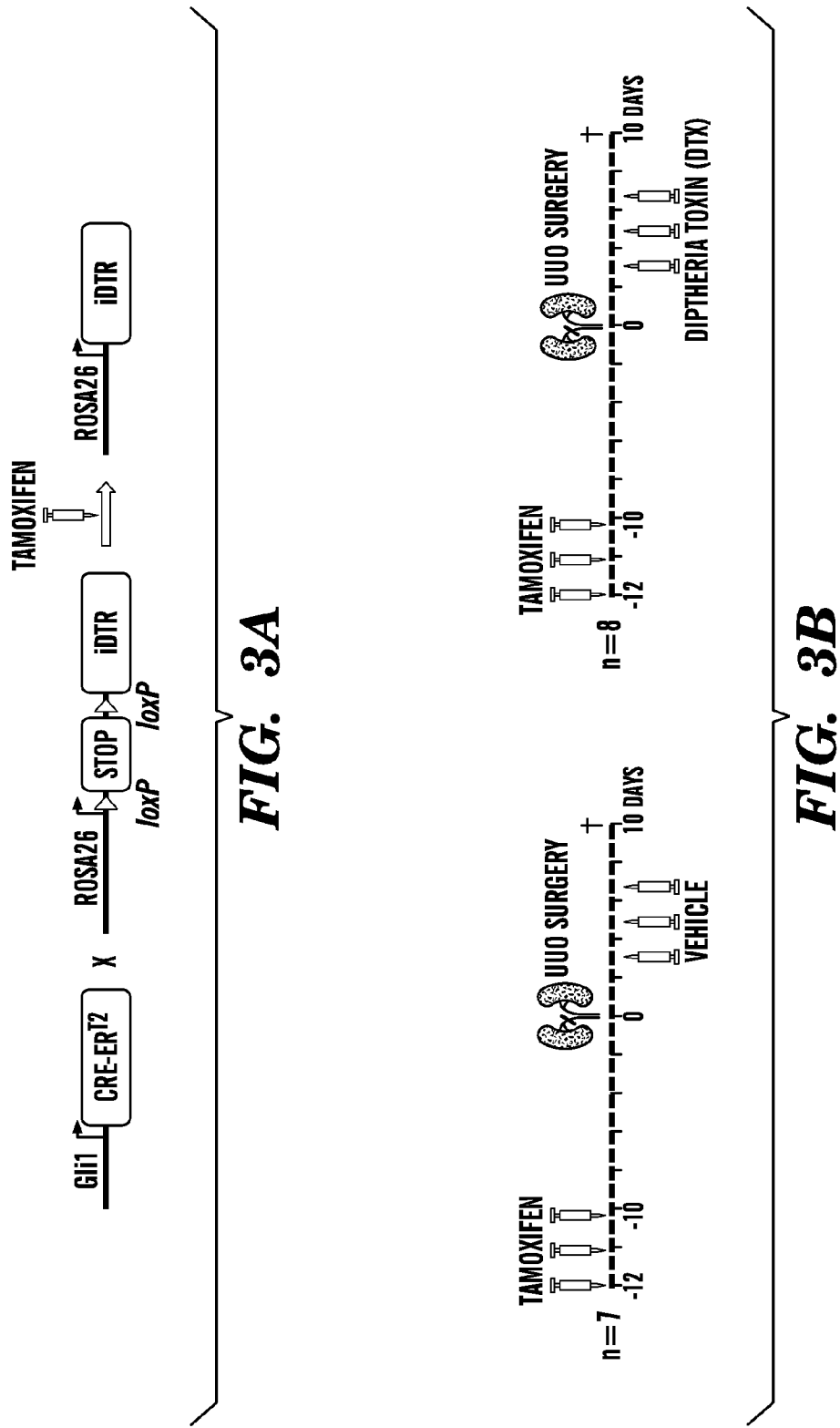

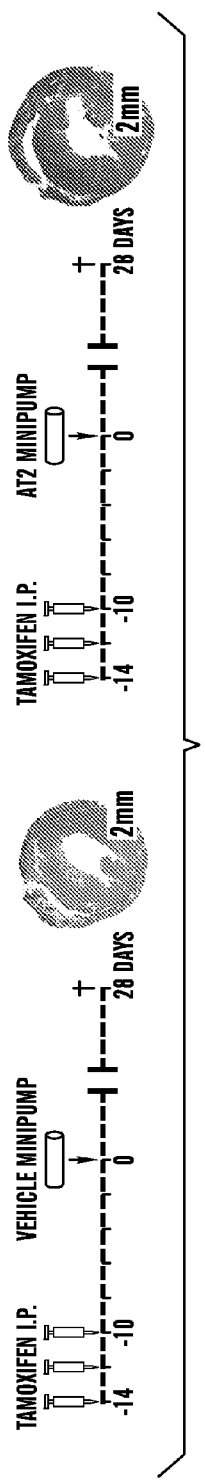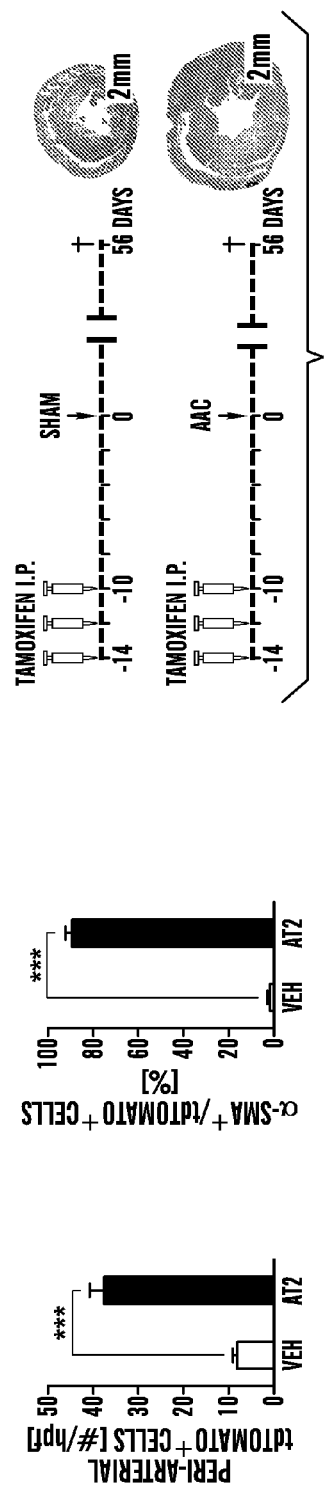
FIG. 9B  FIG. 9C  FIG. 9D  FIG. 9E

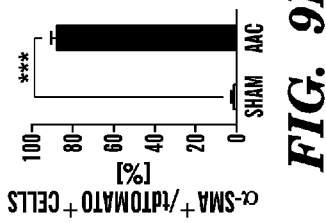
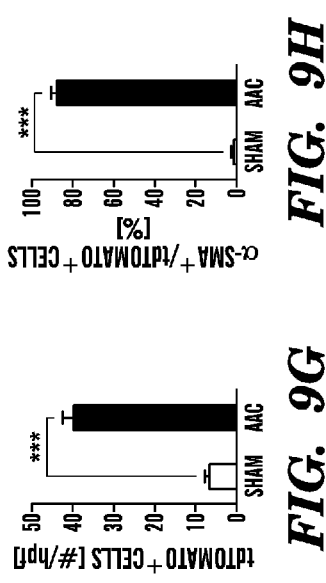
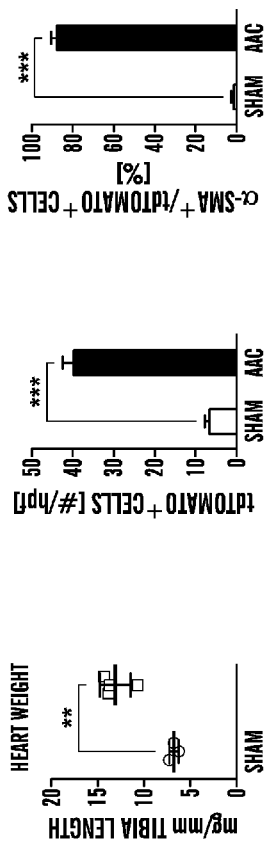
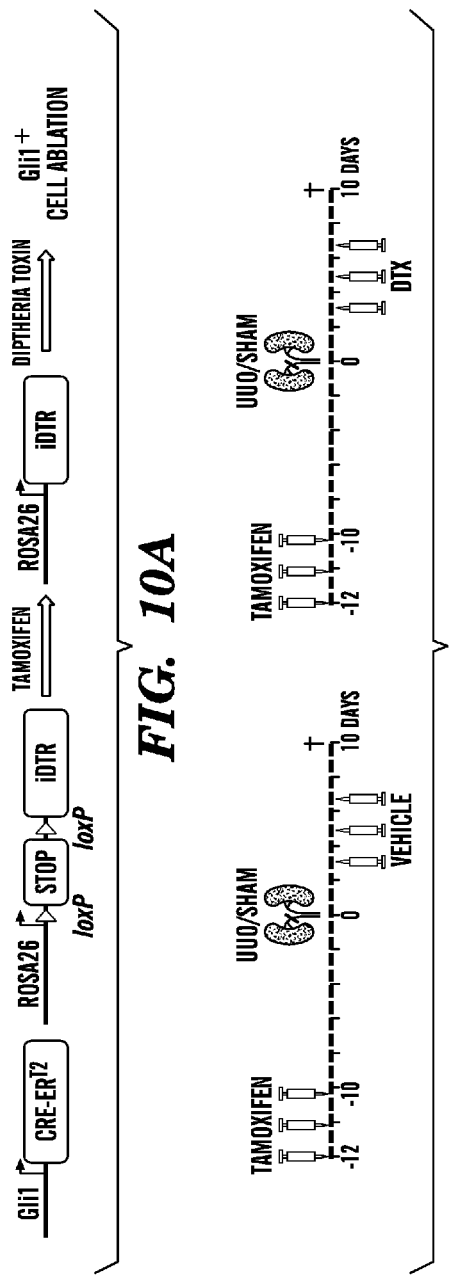

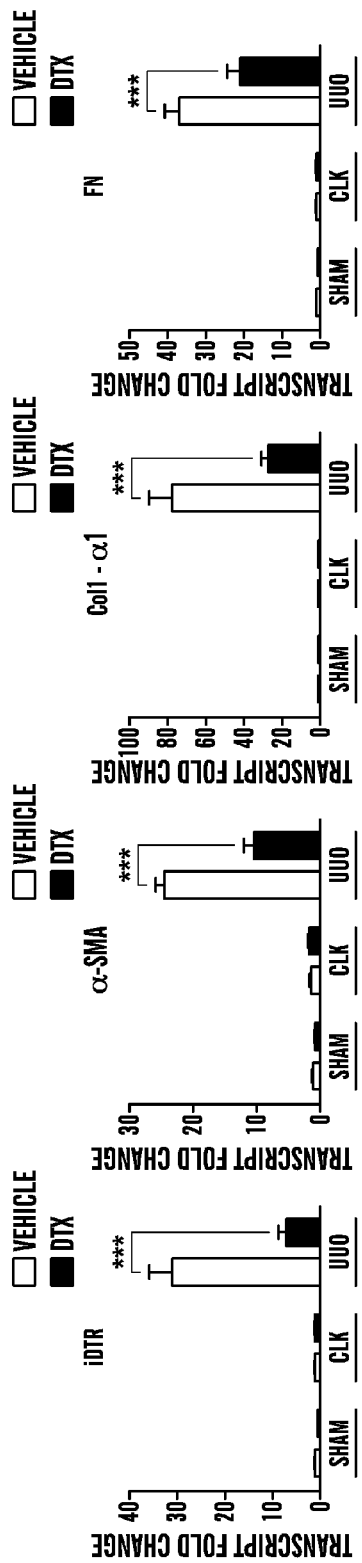
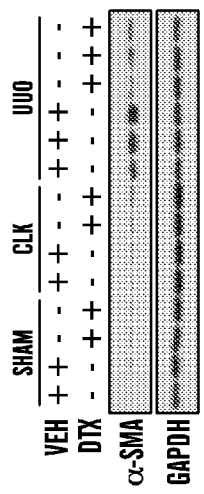
FIG. 10H  FIG. 10I  FIG. 10J  FIG. 10K  FIG. 10L

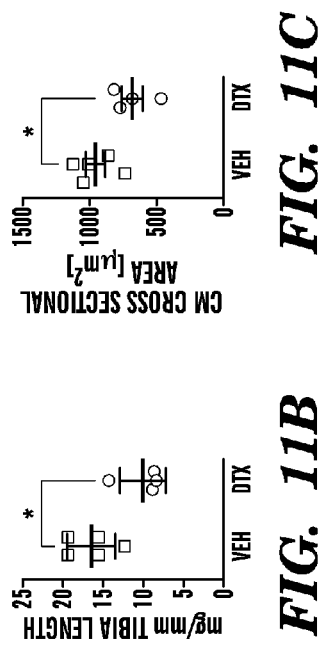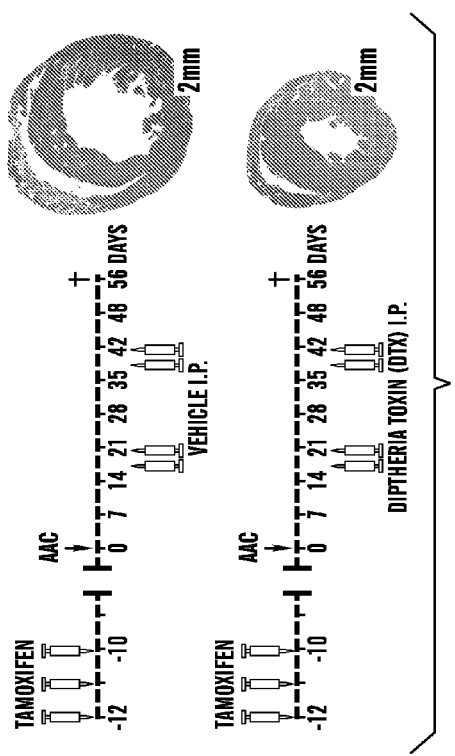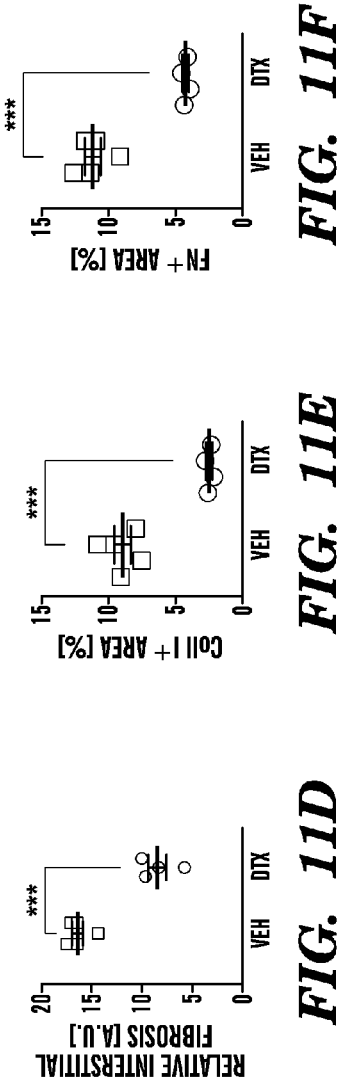
FIG. 11A, FIG. 11B, FIG. 11C, FIG. 11D, FIG. 11E, FIG. 11F

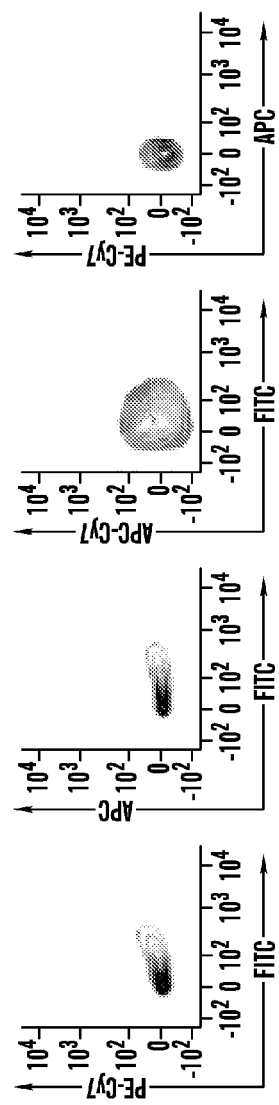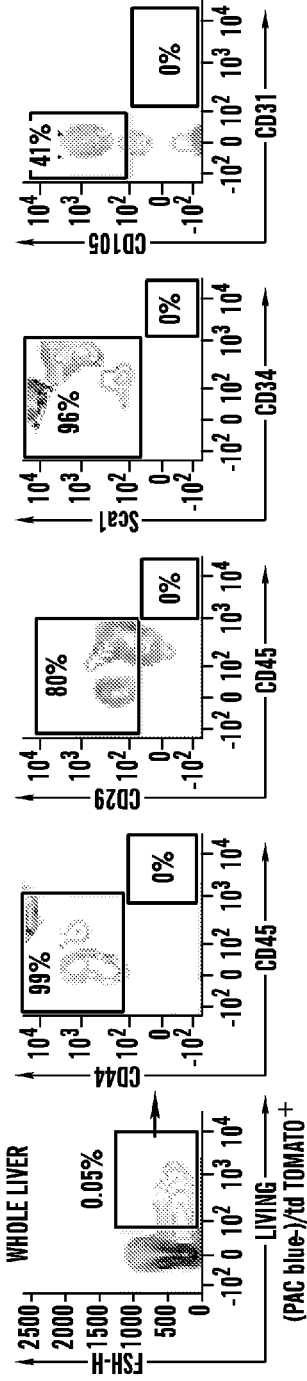
FIG. 13B
FIG. 13C

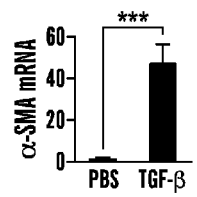
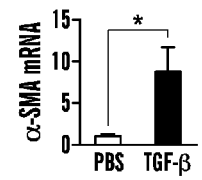
*FIG. 15C*  *FIG. 15D*
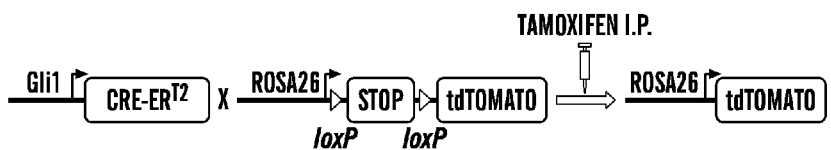
*FIG. 16A*
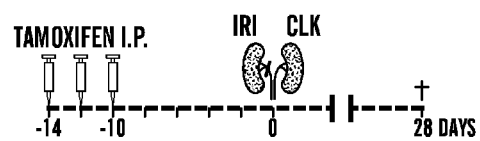
*FIG. 16B*
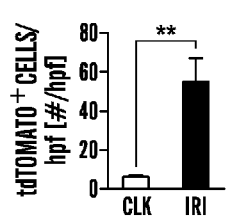
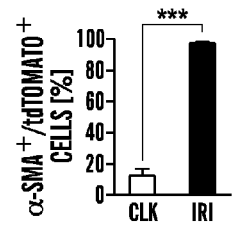
*FIG. 16C*  *FIG. 16D*

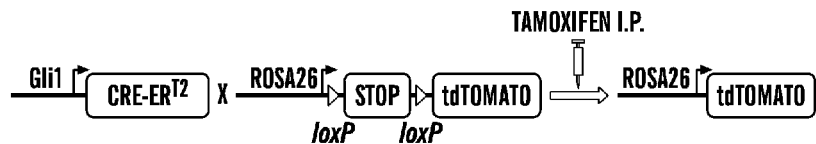
FIG. 17A
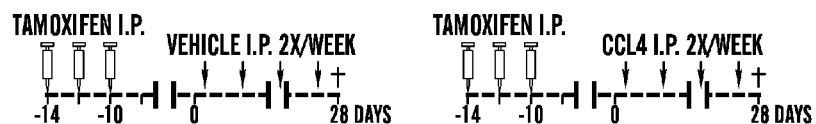
FIG. 17B
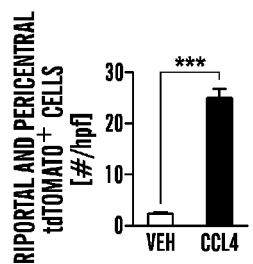 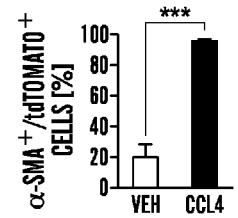
FIG. 17C  FIG. 17D

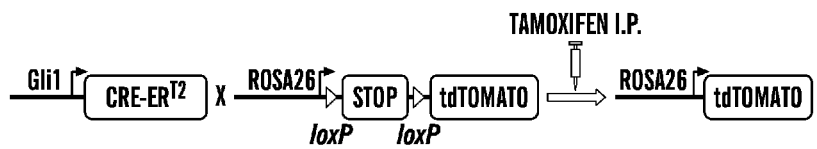
FIG. 18A
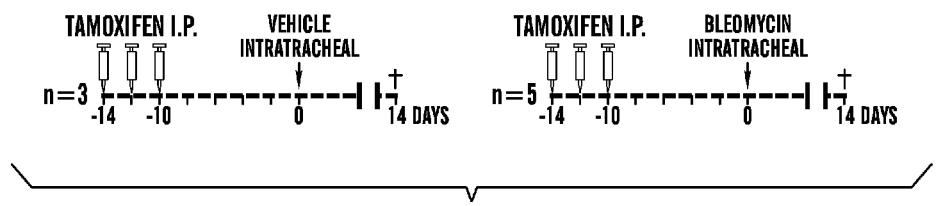
FIG. 18B
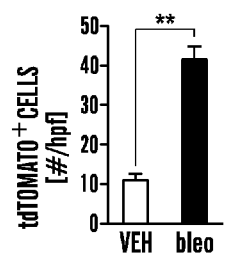 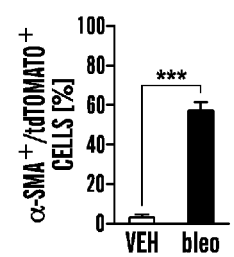
FIG. 18C     FIG. 18D

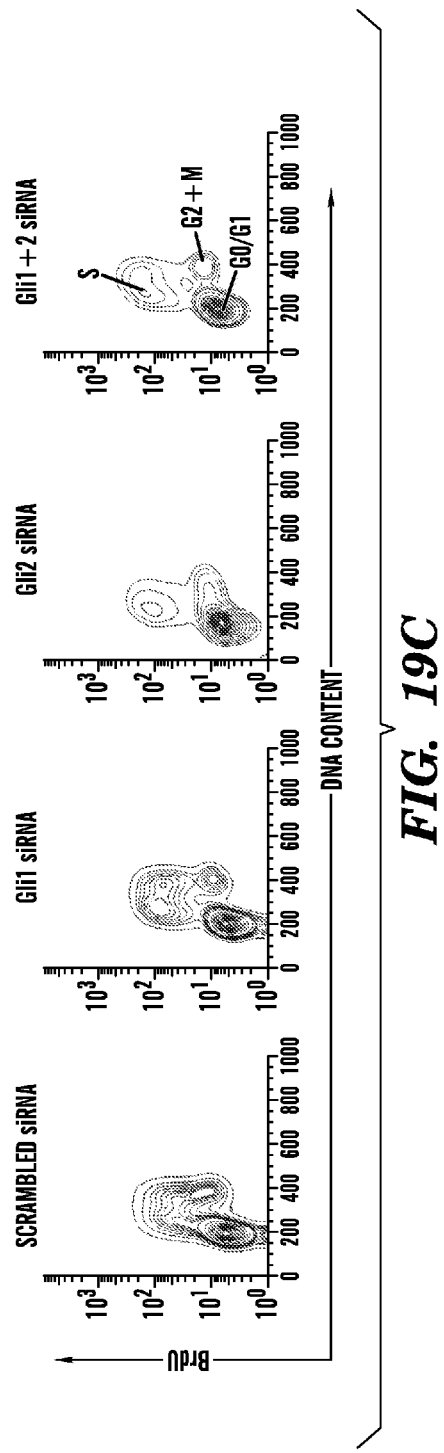
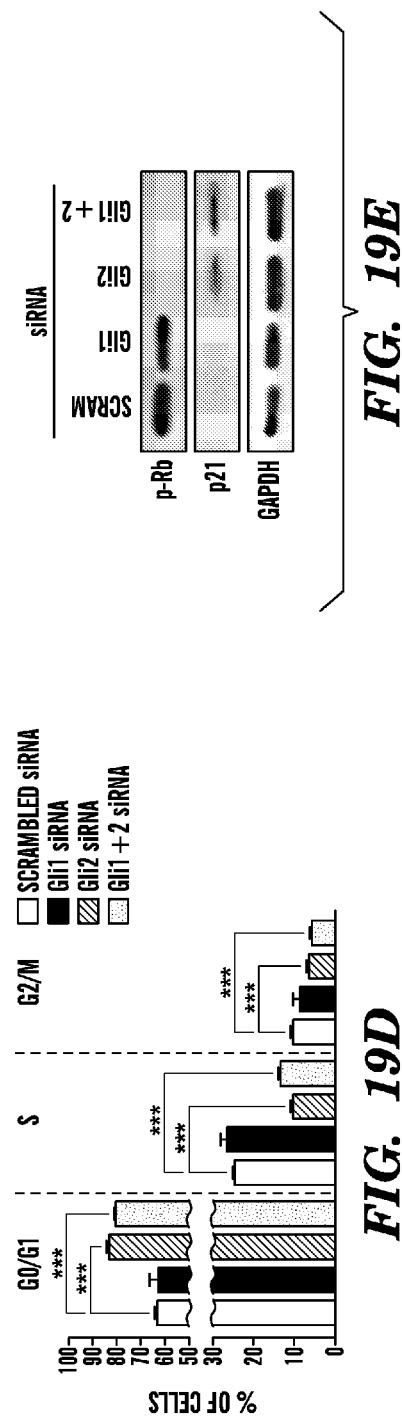
FIG. 19C
FIG. 19D
FIG. 19E

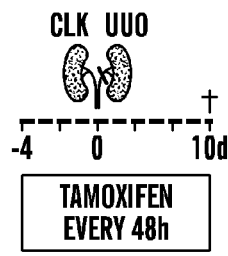
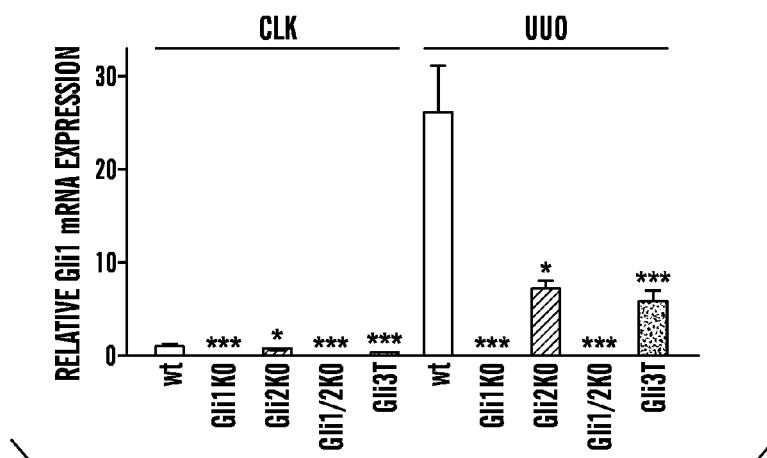
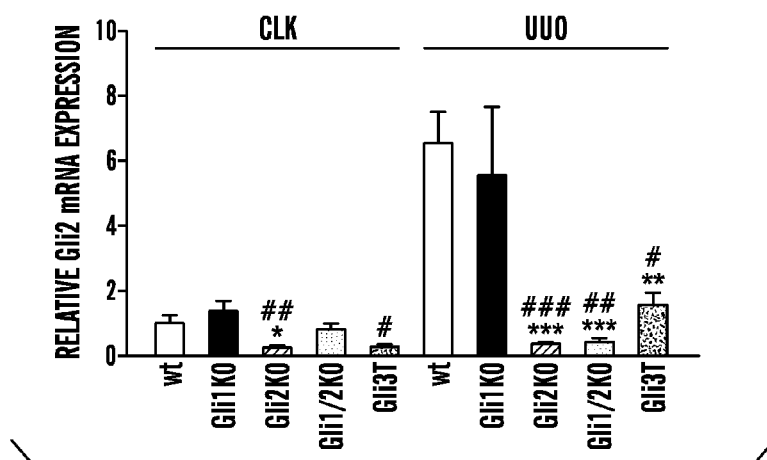
FIG. 20A
FIG. 20B
FIG. 20C

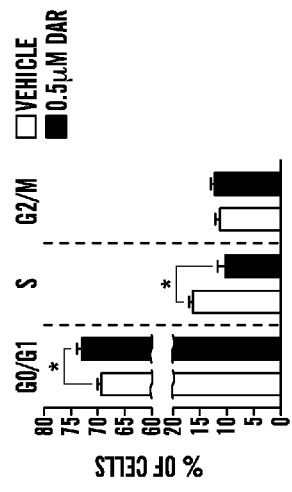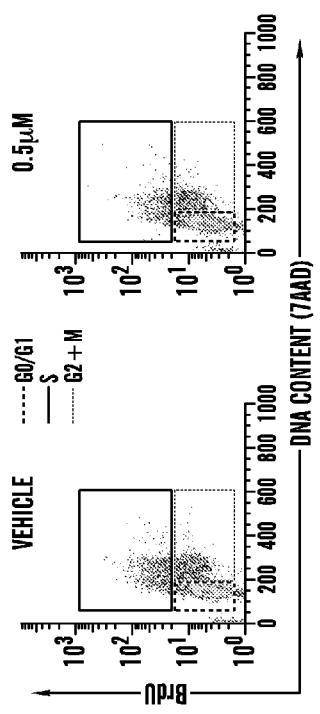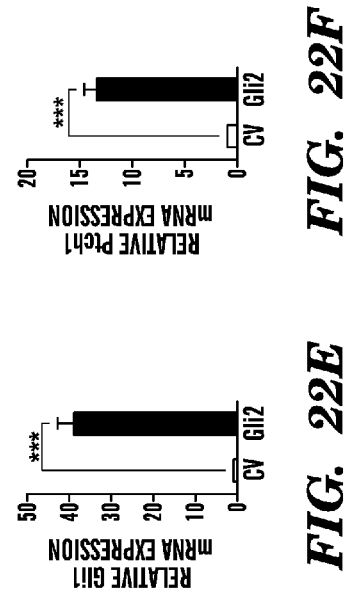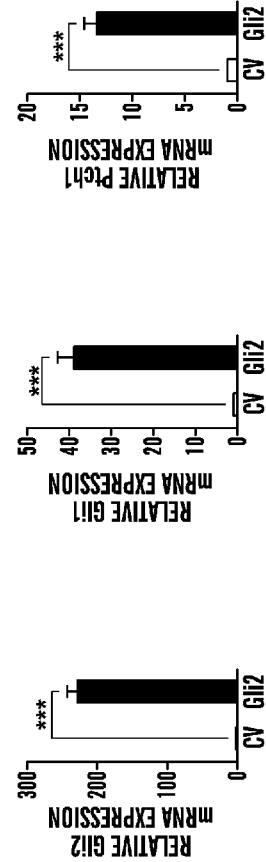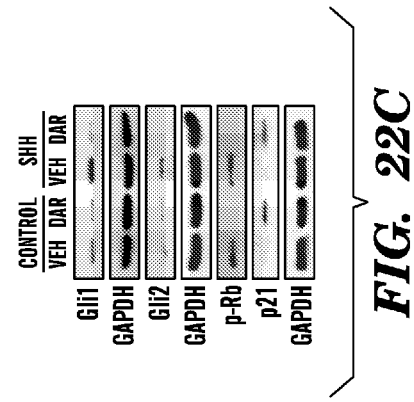
FIG. 22A  FIG. 22B  FIG. 22C  FIG. 22D  FIG. 22E  FIG. 22F

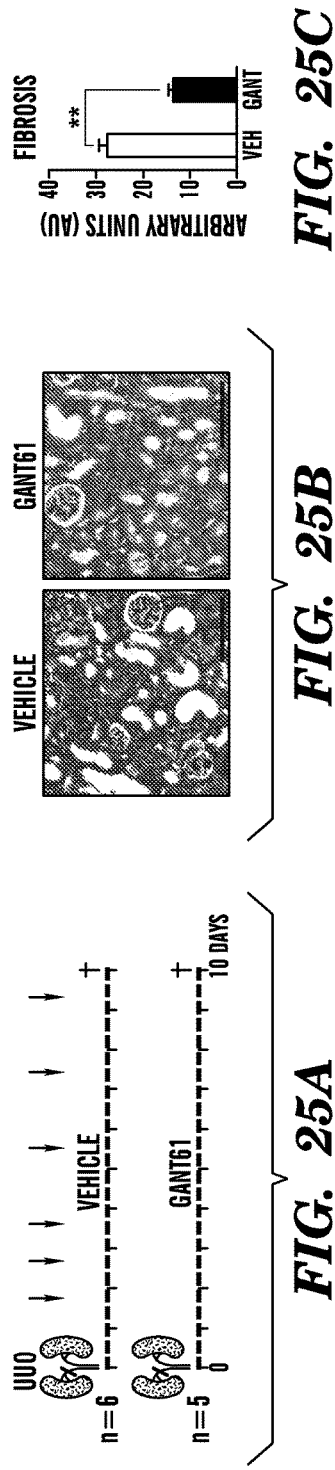
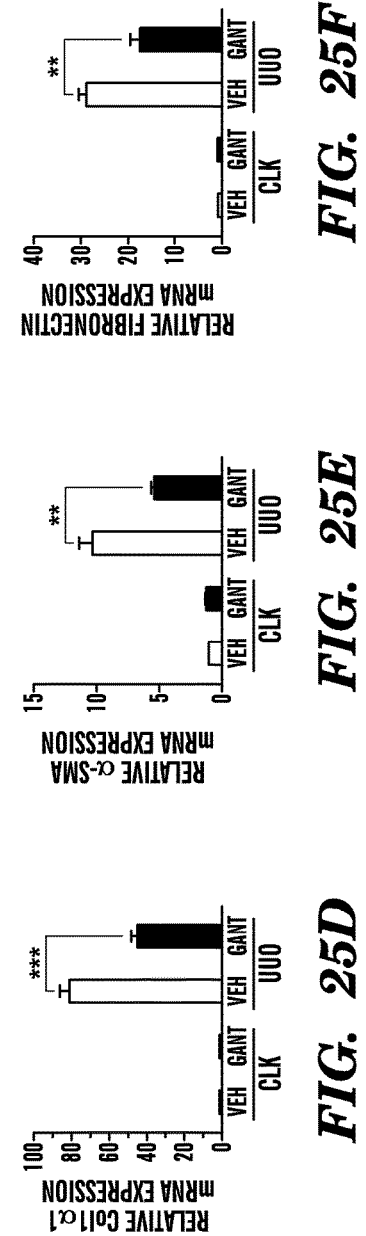
FIG. 25A FIG. 25B FIG. 25C FIG. 25D FIG. 25E FIG. 25F

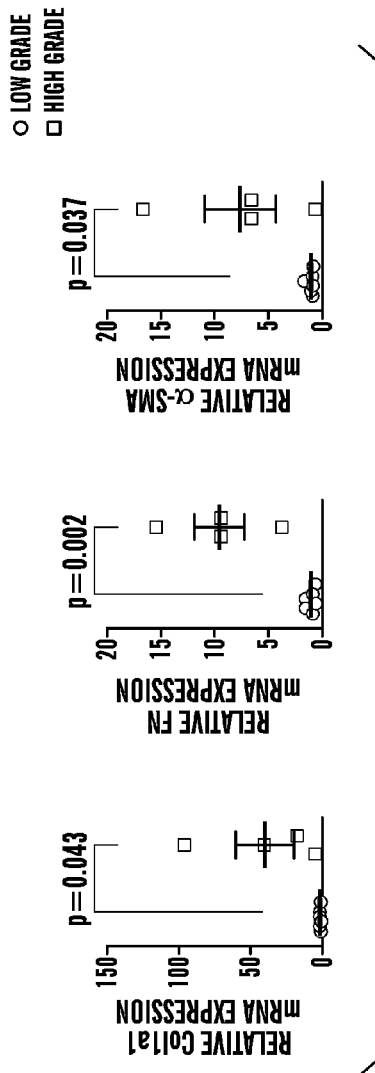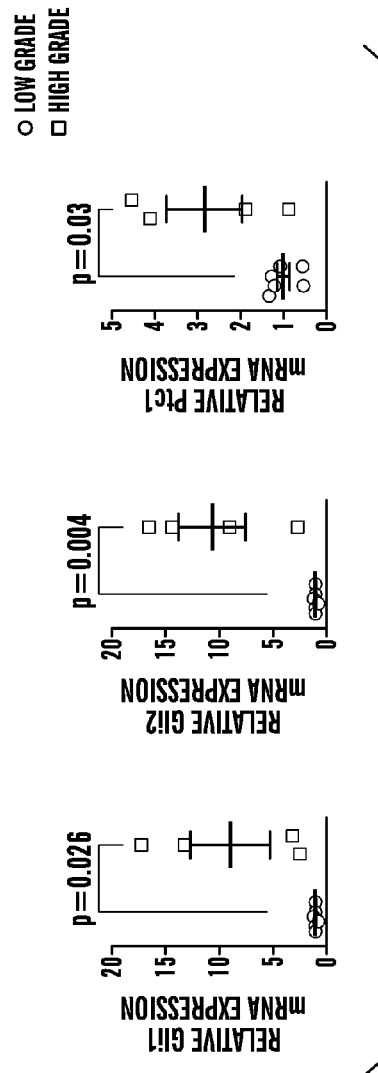

USES OF GLI1 IN DETECTING TISSUE FIBROSIS

CROSS-REFERENCE TO RELATED APPLICATIONS

This application is a 35 U.S.C. § 371 National Phase Entry Application of International Application No. PCT/US2015/014796 filed Feb. 6, 2015, which designates the U.S. and which claims benefit under 35 U.S.C. § 119(e) of U.S. Provisional Application Nos. 61/936,783 filed Feb. 6, 2014 and 62/011,259 filed Jun. 12, 2014, the contents of each of which are incorporated herein by reference in their entirety.

GOVERNMENT SUPPORT

This invention was made with Government support under Grant No.: DK088923 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Apr. 6, 2015, is named 043214-078702-PCT SL.txt and is 3,884 bytes in size.

FIELD OF THE DISCLOSURE

The field of the disclosure relates to mesenchymal stem cells (MSCs), myofibroblast progenitor cells and to fibrosis.

BACKGROUND

Fibrosis is the formation of excess fibrous connective tissue in an organ or tissue in a reparative or reactive process. Fibrosis forms part of the normal wound healing process to facilitate tissue remodeling and scarring. However, upon repeated injury and insult, such as that which occurs in chronic disease, fibrosis can lead to persistent and excessive scarring and, ultimately, organ failure, a common occurrence in all forms of chronic fibrosis. The cells that drive fibrosis are myofibroblasts.

There is currently no unique marker used for identification of MSC and myofibroblasts in fibrotic disease. Identification of MSC and myofibroblasts is typically done with a combination of markers or with markers that are nonspecific, i.e., they have concomitant expression in non-myofibroblasts cell types within the same tissue sample. The ability to identify MSC and myofibroblasts in vivo can facilitate scientific studies for regulating, treatment and management of chronic fibrosis.

SUMMARY

Embodiments of the present disclosure are based on the identification of a novel marker for mesenchymal stem cells (MSCs), myofibroblast expansion, and interstitial fibrosis. This marker is Gli1, a transcription factor in the hedgehog pathway. The inventors found a stromal cell population in kidney that expresses Gli1. These Gli1-positive cells also express the entire typical MSC signature: CD44+, CD29+, Sca1+, CD105+, CD45−, CD34− and CD31−. They can differentiate in bone, cartilage or fat in vitro, defining these Gli1-positive cells as MSC. In addition, the inventors found that this Gli1+ MSC population contributes to interstitial homeostasis during aging and also differentiates into myofibroblasts after injury resulting in myofibroblast expansion, and interstitial fibrosis where there can be an increase in the number of Gli1+ expressing cells. Therefore, the Gli1 marker is useful for the isolation, purification and identification of MSCs, for the detection of myofibroblast expansion and interstitial fibrosis, for the surveillance for myofibroblast expansion and interstitial fibrosis during injury, and also for drug and small molecule screening for therapeutics that can modulate myofibroblast expansion and interstitial fibrosis. Accordingly, it is the objective of this disclosure to provide a method of isolation, purification and identification of MSCs and myofibroblast progenitors using the Gli1 marker.

It is also the objective of this disclosure to provide a method of detecting myofibroblast expansion and interstitial fibrosis using the Gli1 marker and the increase in the number of Gli1+ expressing cells present in tissues.

Similarly, it is the objective of this disclosure to provide a method of surveillance for myofibroblast expansion and interstitial fibrosis using the Gli1 marker and the increase in the number of Gli1+ expressing cells present in tissues.

It is also the objective of this disclosure to provide a method of drug screening for therapeutics that could modulate myofibroblast expansion and interstitial fibrosis using the Gli1 marker and changes in the expression of Gli1.

Accordingly, in one embodiment, provided herein is a method of isolating, detecting or identifying nascent mesenchymal stem cells (MSCs) in an adult tissue, the method comprising contacting a tissue or a population of cells derived from a tissue with an agent that specifically binds to Gli1.

In another embodiment, provided herein is a method of isolating nascent mesenchymal stem cells (MSCs) in an adult tissue comprising isolating Gli1 expressing positive cells.

In one embodiment, provided herein is a method of detecting myofibroblast and/or myofibroblast expansion in an adult tissue, the method comprising contacting a tissue or a population of cells derived from the adult tissue with a first agent that specifically binds to Gli1 and a second agent that specifically binds to alpha-smooth muscle actin.

In one embodiment, provided herein is a method of detecting myofibroblast and/or myofibroblast expansion in an adult tissue comprising detecting an increase in Gli1 expression and/or an increase in Gli1 and alpha-smooth muscle actin expressions in the tissue.

In one embodiment, provided herein is a method of detecting myofibroblast and/or myofibroblast expansion in an adult tissue comprising detecting an expansion of or an increase in Gli1+ cells or Gli+αα-SMA+ in the tissue.

In one embodiment, provided herein is a method of detecting myofibroblast and/or myofibroblast expansion in an adult tissue comprising detecting Gli1positive and/or alpha-smooth muscle actin positive expressing cells.

In one embodiment, provided herein is a method of detecting or monitoring for the induction of tissue fibrosis in an organ, the method comprising: providing a sample of tissue from an organ that is suspected of having tissue fibrosis, detecting myofibroblasts or Gli1positive and/or alpha-smooth muscle actin positive expressing cells in the organ; and identifying a presence of fibrosis in the organ when there is a detectable amount of myofibroblasts.

In one embodiment, provided herein is a method of detecting or monitoring for the induction of tissue fibrosis in an organ, the method comprising providing a sample of tissue from an organ that is suspected of having tissue fibrosis; contacting the tissue or a population of cells derived from the tissue with an agent that specifically binds to Gli1; measuring a level of Gli1 expression in the tissue or a population of cells derived from the tissue; comparing the measured level of Gli1 expression with a reference; and identifying a presence of fibrosis in the organ when there is an increase in Gli1 expression over the reference or identifying an absence of fibrosis in the organ when there is a decrease or no difference in Gli1 expression compared to the reference. The patient identified as having fibrosis by any method described herein can further be treated.

In one embodiment, provided herein is a method of monitoring the progression of tissue fibrosis in an organ from an individual, the method comprising: providing a first sample of tissue at a first time point from the organ that is having tissue fibrosis; determining the level of Gli1 expression in the first sample; providing a second sample of tissue at a second time point from the same organ that is having tissue fibrosis, the first time point being before the second time point; determining the level of Gli1 expression in a second sample; comparing the levels of Gli1 from the time points with a reference Gli1 level; and assessing that tissue fibrosis in an organ is regressing where the levels of Gli1 at the second time point is lower than the reference Gli1 level, or assessing that tissue fibrosis in an organ is progressing where the levels of Gli1 at the second time point is higher than the reference Gli1 level.

In one embodiment, provided herein is a method for monitoring treatment efficacy of a subject with pathogenic fibrosis or chronic fibrosis, the method comprising: (a) determining, from a biological sample obtained from a subject at a first time-point, a level of Gli1; (b) administering treatment to the subject; (c) determining a level of Gli1 in a sample obtained from said subject at a second time-point; and (d) comparing the level Gli1 at the second time-point with the level of Gli1 at the first time-point.

In one embodiment of any method, the method further comprises determining the level of α-SMA in the first and second points, and also comparing the time level of α-SMA from the second time point with that of the first time point.

In one embodiment of any method, wherein a decrease in the level of Gli1 and/or a-SMA at the second time-point indicates the treatment is efficacious for the subject, and wherein an increase in the level of Gli1 and/or a-SMA at the second time-point indicates the treatment is not efficacious for the subject.

In one embodiment of any one method described herein, the adult tissue is in an organ.

In one embodiment of any one method described herein, the organ is solid organ.

In one embodiment of any one method described herein, the organ is selected from heart, liver, lung, kidney, skin and bone marrow.

In one embodiment of any one method described herein, the detecting comprises contacting a tissue or a population of cells derived from a tissue with an agent that specifically binds to Gli1. For example, the agent is an antibody against Gli1.

In one embodiment of any one method described herein, the agent that specifically binds Gli1 is an anti-Gli1 antibody.

In one embodiment of any one method described herein, the method comprises an immune assay.

In one embodiment of any one method described herein, the detecting comprises an immune assay.

In one embodiment of any one method described herein, the method further comprises selecting an organ that is suspected of having tissue fibrosis, eg. from tissue injury.

In one embodiment of any one method described herein, the method further comprises selecting a subject or individual suspected of having tissue fibrosis. The subject may have had an injury to the organ that is known to initiate fibrosis.

In one embodiment of any one method described herein, the method further comprises identifying a presence of fibrosis in the organ when there is an increase in Gli1positive and alpha-smooth muscle actin positive expressing cells over the reference or identifying an absence of fibrosis in the organ when there is a decrease or no difference in Gli1positive and alpha-smooth muscle actin positive expressing cells compared to the reference.

In one embodiment of any one method described herein, the method further comprises treating or inhibiting the fibrosis by administering at least an anti-fibrosis treatment when the presence of fibrosis in the organ is identified.

In one embodiment of any one method described herein, the method further comprises measuring the level of alpha-smooth muscle actin in the same tissue or a population of cells derived from the tissue and comparing with the measured level of alpha-smooth muscle actin with a reference.

In one embodiment of any one method described herein, the method further comprises selecting an individual suspected of developing or at risk of developing fibrosis.

In one embodiment of any one method described herein, the method further comprises treating or inhibiting the fibrosis by administering at least an anti-fibrosis treatment when the presence of fibrosis in the organ is identified.

In one embodiment of any one method described herein, the method further comprises measuring the level of alpha-smooth muscle actin in the same first and second samples and comparing with the measured level of alpha-smooth muscle actin with a reference.

In one embodiment of any one method described herein, the method further comprises selecting an individual who is diagnosed with fibrosis and measuring organ fibrosis by Masson's Trichrome staining, collagen staining or by picrosirius red staining.

In one embodiment of any one method described herein, the method further comprises continuing treating or inhibiting the fibrosis by administering at least an anti-fibrosis treatment when the presence of fibrosis in the organ is identified.

In one embodiment, provided herein is a method of screening for an inhibitor or modulator of fibrosis comprising providing a Gli1 expressing positive cell, contacting the Gli1 expressing positive cell with at least one candidate compound or agent; and measuring the level of expression of Gli1 in the cell in contact with candidate compound or agent.

In one embodiment of any one method described herein, the method further comprises comparing the measured level of Gli1 expression with a reference wherein the measured level of Gli1 expression is reduced compared to the reference indicate that the candidate compound or agent is a likely inhibitor of tissue fibrosis.

In some embodiments of any method described, cells of the organ under study can be dissociated and purified with a purification protocol such as FACS to isolate the cells, eg, kidney cells for studying kidney fibrosis. This involves mincing of kidney followed by dispase digestion. FACS offers the advantage of quantitative measurement of cell number in the tissue, as well as the ability to rigorously define cell surface profiles. FACS will also be used to isolate the Gli1+ cells for transplantation under the kidney capsule.

In one embodiment of any method described, the method further comprises selecting a subject who has exhibited tissue fibrosis is an organ or a subject who is at risk of developing tissue fibrosis is an organ. For example, a subject who has suffered a traumatic injury in an organ, or one with chronic organ failure.

In one embodiment of the method described, the method further comprises selecting a subject who has exhibited tissue fibrosis previously in another organ or tissue.

In one embodiment of the method described, the method further comprises administering at least one treatment for tissue fibrosis. Any treatment methods for fibrosis and compositions for the treatment of tissue fibrosis known in the art can be administered, for example, those described in US Patent Application Publication No: 2005/017665, entitled "Polymer compositions and method for their uses" in paragraphs 77-338, such as angiogenesis inhibitors and cathepsin inhibitors.

In one embodiment of any method described, the organ or tissue being tested for tissue fibrosis is kidney.

In one embodiment of any method described, kidney fibrosis is assessed by performing a serum BUN and creatinine analyses as well as assessing the glomerular filtration rate via 24 h urine collection using assays standard.

BRIEF DESCRIPTION OF THE DRAWINGS

FIGS. 3A-3F show that genetic ablation of Gli1+ MSC ameliorates fibrosis in the UUO, proving that these are the critical fibrogenic cells in this kidney fibrosis model. FIG. 3A. Breeding scheme. FIG. 3B. Tamoxifen and DTX administration scheme. FIGS. 3C-E. Ablation of Gli1+ cells reduces fibrotic endpoints. FIG. 3F. There is a strong reduction in human DTR mRNA, serving as an internal control for successful ablation of Gli1+ cells. There is a strong reduction in αSMA+ myofibroblasts after DTX. CLK, contralateral kidney. UUO—fibrotic kidney (data not shown).

FIG. 8A. Genetic labeling of Gli1 expressing cells in non-injured mice using the Gli1Cre-ERt2 driver crossed to the Rosa26-tdTomato reporter line enables cell specific expression of the bright red fluorochrome tdTomato following tamoxifen (3×0.1 mg/kgBW 2 days prior to analysis) induced recombination (BM, bone marrow). Gli1-tdTomato+ cells reside in a perivascular niche with direct contact to CD31+ endothelial cells across different organs and tissues (data not shown). In addition to this microvascular niche, Gli1-tdTomato+ cells localize to the adventitia of arteries, around biliary ducts and pulmonary bronchi and bronchioles (data not shown). Gli1-tdTomato+ cells express the pericyte marker PDGFR-β (data not shown). FIG. 8B. Fluorescence activated cell sorted (FACS) Gli1-tdTomato+ cells from different organs and tissues possess in vitro three-lineage differentiation capacity towards osteoblasts (Alizarin Red staining), adipocytes (Oil-red O staining) and chrondrocytes (Alcian Blue staining). FIG. 8C. Flow cytometry from whole digested organs demonstrates that Gli1-tdTomato+ cells express a typical MSC surface pattern in situ with high expression of CD29, Sca1, CD44, CD105, low expression of CD34 and are negative for endothelial and hematopoietic lineage markers (CD31 and CD45 respectively). (scale bars in FIG. 8C, data is presented as mean±SEM)

FIGS. 9A-9H show genetic fate tracing of mesenchymal stem cells in heart and kidney fibrosis. FIG. 9A. Bigenic Gli1; CreERt2,tdTomato mice were injected with tamoxifen and subjected to unilateral ureteral obstruction (UUO, n=4, CLK contralateral non-injured kidney) surgery 10 days after the last tamoxifen dose allowing genetic fate tracing of tdTomato+ MSC and their descendants. Following UUO, MSC expand and gain alpha smooth muscle actin (α-SMA) expression. FIGS. 9B-9D. Myocardial fibrosis was induced by implantation of angiotensin 2 (AT2, n=4) containing osmotic minipumps 10 days after the last tamoxifen injection (PBS pumps in controls, n=3). Gli1+-MSC expand and transdifferentiate into α-SMA+ myofibroblasts due to the hypertension induced, predominantly perivascular, fibrosis around myocardial arteries. FIGS. 9E-9H. As a model of more pronounced interstitial myocardial fibrosis with cardiac hypertrophy and chronic heart failure, Gli1; CreERt2, tdTomato mice underwent ascending aortic constriction (AAC, n=4) or sham surgery (n=3) as indicated. Following AAC Gli1+-MSC expand dramatically in the myocardial interstitium and gain α-SMA expression (Scale bars 500 μm left panel in FIG. 9A and both left panels in FIG. 9B, all others 50 μm in FIG. 9A and FIG. 9B; =$p<0.01$, *=$p<0.001$ by t-test, data is presented as mean±SEM, hpf-high power field 400×).

FIGS. 10A-10L show cell-specific ablation of mesenchymal stem cells via the human diptheria toxin receptor ameliorates kidney fibrosis. FIG. 10A. To specifically ablate Gli1+ MSC in the kidney, Gli1CreERt2 mice were crossed with a Cre-inducible diphtheria toxin receptor (iDTR) transgenic mouse. Injection of tamoxifen therefore induces heritable expression of the human iDTR in Gli1+-MSC and all descendant cells, allowing ablation of these cells via diphteria toxin (DTX) injection. FIG. 10B. Bigenic Gli1CreERt2+; iDTR+ mice were subjected to UUO or sham surgery, injected with vehicle (VEH, PBS) or DTX following surgery as indicated (n=5 sham+VEH, n=7 sham+DTX, n=7 UUO+VEH, n=8 UUO+DTX). FIGS. 10C-10G. Ablation of Gli1+-MSC reduced kidney fibrosis following UUO as demonstrated by trichrome staining, immunostaining for alpha smooth muscle actin (α-SMA), collagen1α1 and fibronectin and their quantification. FIGS. 10H-10I. Quantitative realtime PCR shows a ~30 fold upregulation of iDTR in UUO kidneys reflecting the expansion of Gli1+-MSC, whereas DTX injection significantly reduced iDTR expression in UUO kidneys with subsequently reduced expression of the fibrotic readouts α-SMA, collagen1α1 and fibronectin. FIG. 10L. Representative western blot for alpha smooth muscle actin. (Scale bars middle panel 500 µm all others 50 µm; ***=p<0.001 by t-test, data is presented as mean±SEM; hpf-high power field 400×).

FIGS. 11A-11N show selective ablation of perivascular mesenchymal stem cells after ascending aortic constriction reduces myocardial fibrosis and rescues left ventricular function. FIGS. 11A-11C. Bigenic Gli1CreERt2+; iDTR+ mice underwent ascending aortic constriction (AAC) 10 days after the last tamoxifen injection and were randomized to receive either diphteria-toxin (DTX) or vehicle (VEH, PBS) injections in order to ablate Gli1+-MSC and descendant myofibroblasts. Ablation of MSC ameliorated cardiac hypertrophy as indicated by reduced heart weight and cardiomyocyte (CM) cross-sectional area. FIG. 11D. Representative trichrome stained images and quantification revealed significantly reduced myocardial fibrosis following cell-ablation. FIGS. 11E-11J. MSC ablation resulted in significantly reduced expression of iDTR, α-SMA, collagen1α1 and fibronectin. FIGS. 11M-11N. As expected the vehicle injected mice developed a progressive heart failure (representative echocardiographic M-mode pictures in FIG. 11M) with significantly reduced left ventricular ejection fraction (EF) at 8 weeks whereas ablation of MSC rescued this progressive heart failure following AAC. (Scale bars 50 µm; *=p<0.05 =p<0.01, *=p<0.001 by t-test, data is presented as mean±SEM)

FIGS. 13A-13D show representative gating and plots of whole organ flow cytometry from kidney, liver and lung. FIG. 13A. Representative gating on a cell population regarding cell-size (forward scatter FSC) and granularity (sideward scatter SSC) followed by gating on single cells and pacific blue (DAPI negative) viable cells. A similar gating was performed for all organs. FIG. 13B. Representative plots of a digested Gli1-tdTomato+ kidney without addition of antibodies. Similar negative organ-specific samples were used for defining the gates in the flow cytometric analysis of other tissues. FIGS. 13C-13D. Representative flow cytometric plots of whole digested liver and lung.

FIGS. 15A-15D show mesenchymal stem cells from heart and bone chips gain αSMA expression upon TGF beta treatment. Gli1-tdTomato+ cells are positioned surrounding endothelial cells of bone-marrow sinusoides and are distributed along the endosteum (data not shown). Images of Gli1-tdTomato+ MSC migrating out of compact bone chips in the culture dish are not shown. FIG. 15A. Representative flow cytometric plots of BM-MSC isolated from compact bone chips. FIG. 15B. Representative flow cytometric analysis of cultured (after FACSort) Gli1-tdTomato+ cells from the myocardium. FIGS. 15C-15D. Both MSC isolated from compact bone or heart muscle gain alpha smooth muscle actin (α-SMA) expression upon treatment with transforming growth factor beta (TGF-β) (Scale bars 50 µm in FIG. 15C and FIG. 15D, *=p<0.05, ***=p<0.001 by t-test, data is presented as mean±SEM).

FIGS. 16A-16D show fate tracing of Gli1+ mesenchymal stem cells in kidney fibrosis following unilateral ischemia reperfusion injury. FIG. 16A-16B. Bigenic Gli1,tdTomato+ mice were injected with tamoxifen, underwent unilateral ischemia reperfusion injury (IRI) of the kidney 10 days after the last injection of tamoxifen and were euthanized 4 weeks after the surgery (CLK contralateral non-injured kidney). FIG. 16C-16D. Following severe IRI the Gli1-tdTomato+ MSC dramatically expand and gain alpha smooth muscle actin expression during progression of kidney fibrosis. (Scale bars left panel 500 µm, all others 50 µm, =p<0.01, *=p<0.001 by t-test, data is presented as mean±SEM, hpf-high power field 400×).

FIGS. 17A-17D show fate tracing of Gli1+ mesenchymal stem cells in carbon tetrachloride ($CCl_4$) induces liver fibrosis. FIGS. 17A-17B. Bigenic Gli1-tdTomato+ mice were injected with tamoxifen, received carbon tetrachloride injections ($CCl_4$) or vehicle (corn oil) twice per week (intraperitoneally) starting 10 days after the last tamoxifen injection and were euthanized at 4 weeks after the first $CCl_4$/vehicle injection. FIGS. 17B-17D. $CCl_4$ injection resulted in liver injury with hepatocyte necrosis (asterisk) and fibrosis with expansion of Gli1-tdTomato+ cells in fibrotic streets (arrowheads). Gli1-tdTomato+ cells acquire alpha smooth muscle actin expression (arrows). (Scale bars left panel 500 µm, all others 50 µm, =p<0.01, *=p<0.001 by t-test, data is presented as mean±SEM, hpf-high power field 400×).

FIGS. 18A-18D show fate tracing of Gli1+ mesenchymal stem cells in bleomycin induced lung fibrosis. FIGS. 18A-18B. Bigenic Gli1,tdTomato+ mice were injected with tamoxifen, received a single dose of bleomycin or vehicle (normal saline) intratracheally 10 days after the last tamoxifen injection and were euthanized 14 days after the bleomycin/vehicle administration. Bleomycin injection induced a severe pulmonary fibrosis as indicated by trichrome staining (data not shown). FIG. 18C. Gli1-tdTomato+ cells line the peri-bronchial smooth muscle cell layer of a healthy non-injured lung of a control mouse which only received normal saline (vehicle) intratracheally (data not shown). Following intratracheal bleomycin instillation the Gli1-tdTomato+ cells expand into the lung interstitium and gain alpha smooth muscle actin (α-SMA) expression (arrows)

indicating their transdifferentiation to myofibroblasts. (Scale bars as indicated, =p<0.01, *=p<0.001 by t-test, data is presented as mean±SEM, hpf-high power field 400x).

Figure 19A:
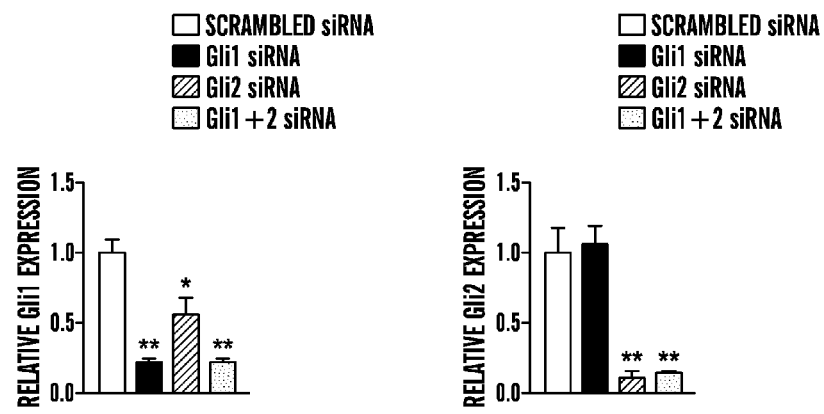
Figure 19B:
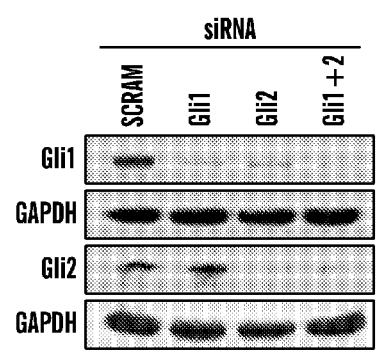

FIGS. 19A-19E show data indicating that lowering Gli2, but not solely Gli1, by RNAi induces a cell-cycle arrest of MSC-like cells in vitro. FIGS. 19A-19B. mRNA and protein levels of Gli1 and Gli2 in 10T1/2 cells treated with siRNA as indicated. Shh was added to the medium to increase Gli protein levels for better detection. FIGS. 19C-19D. Representative flow cytometric cell-cycle plots and quantification of 10T1/2 cells after siRNA mediated knockdown of Gli1, Gli2 or both Gli1/Gli2 compared to scrambled siRNA. FIG. 19E. Representative western blot of the cell-cycle regulators at the G1 restriction point phosphorylated retinoblastoma (pRb) and p21 following knockdown of Gli1, Gli2 or Gli1/2. *p<0.05, p<0.01, *p<0.001, A by t-test, D by one way ANOVA with posthoc Bonferroni, data presented as mean±SEM.

Figure 20D:
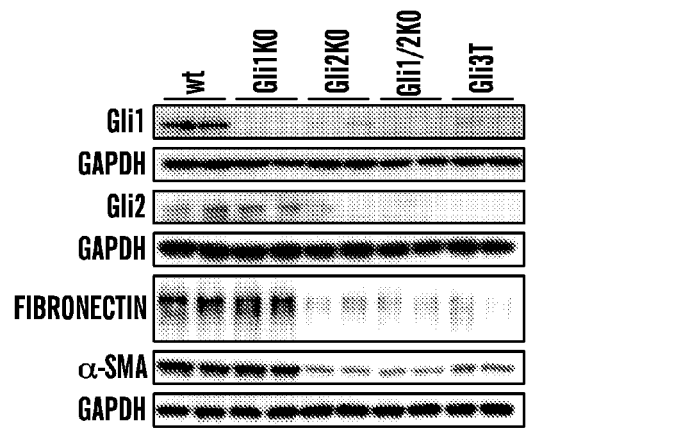
Figure 20E:
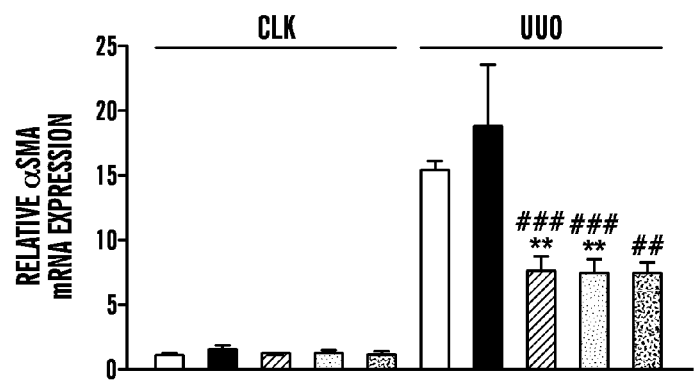
Figure 20E:
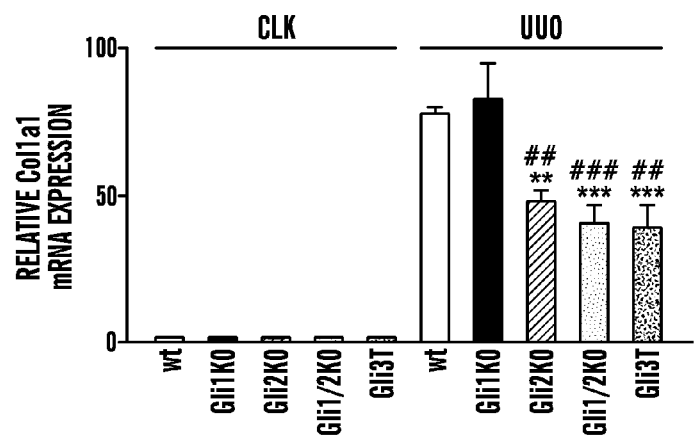
Figure 20F:
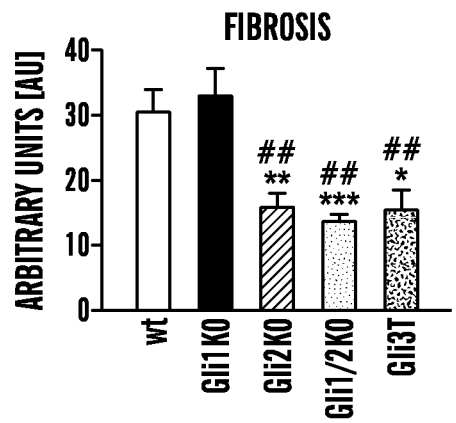
Figure 20G:
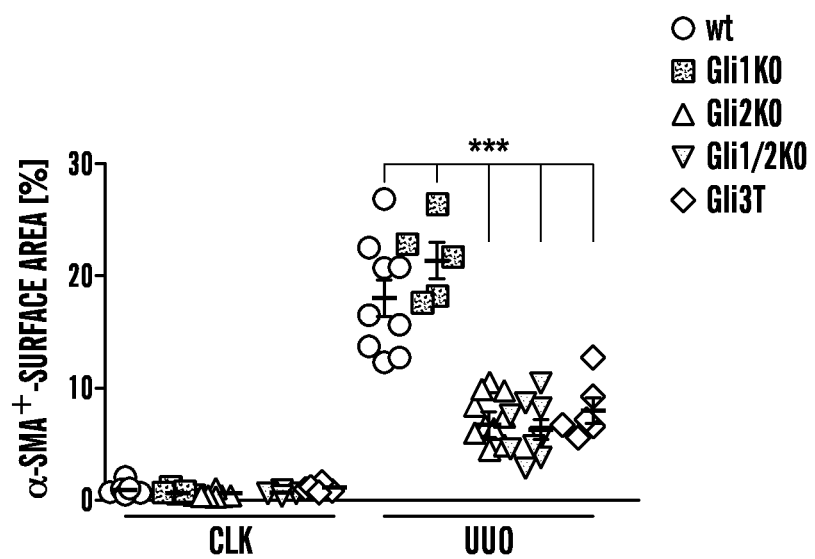

FIGS. 20A-20G show data indicating that conditional knockout of Gli2 or overexpression of the Gli3 repressor in Gli1+ cells ameliorates kidney fibrosis following unilateral ureteral obstruction (UUO). FIG. 20A. Wildtype littermates (wt, n=9), Gli1KO (Gli1CreER$^{t2+/+}$;Gli2flox$^{-/-}$ n=5), conditional Gli2 KO (Gli1CreER$^{t2+/+}$;Gli2flox$^{+/+}$, n=12), Gli1/2 KO (Gli1CreER$^{t2+/+}$;Gli2flox$^{+/+}$, n=9), or Gli3T mice (Gli1CreER$^{t2+/-}$;Gli3T$^{+/-}$, n=6) were injected with tamoxifen, underwent UUO surgery as indicated and were sacrificed at 10 days after UUO. FIGS. 20B-20F. Representative mRNA expression and western blots for Gli effector proteins Gli1 and Gli2 and fibrotic readouts, fibronectin, collagen1a1 and alpha smooth muscle actin (α-SMA). FIG. 20G. Representative images of trichrome or α-SMA stained UUO kidneys at 10 days after surgery. FIGS. 20H-20I. Quantification of interstitial fibrosis and α-SMA+ surface area. *p<0.05, p<0.01, *p<0.001 versus wt, #p<0.05, ##p<0.01, ###p<0.001 versus Gli1 KO, by one way ANOVA with posthoc Bonferroni, data presented as mean±SEM.

Figure 21A:
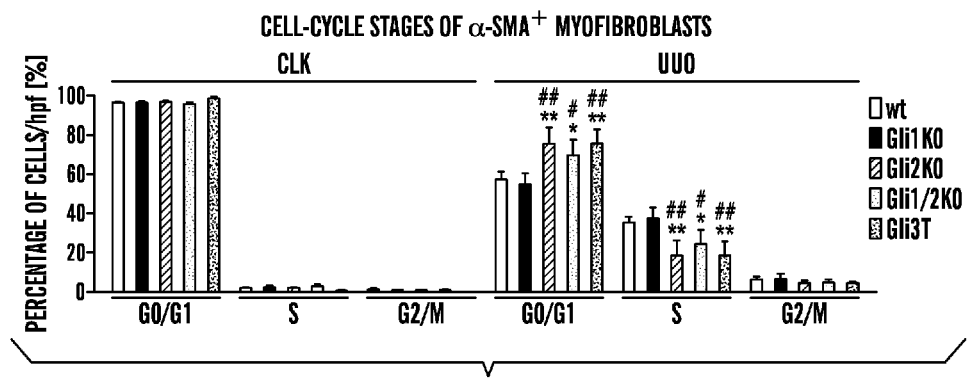
Figure 21B:
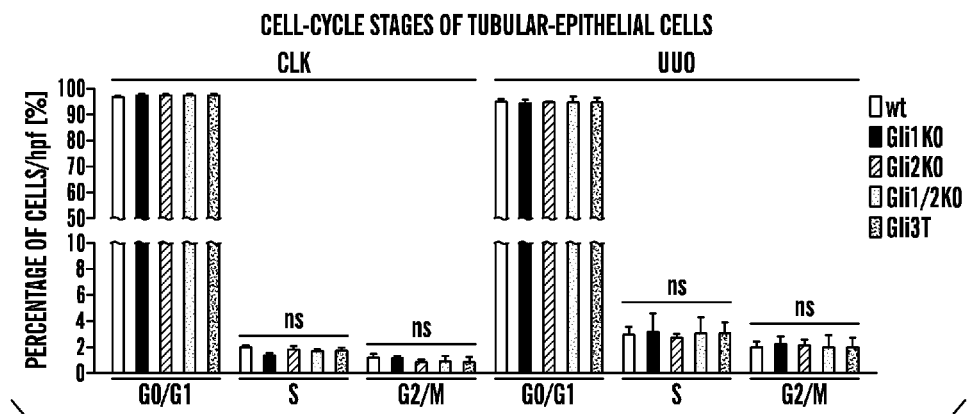
Figure 21C:
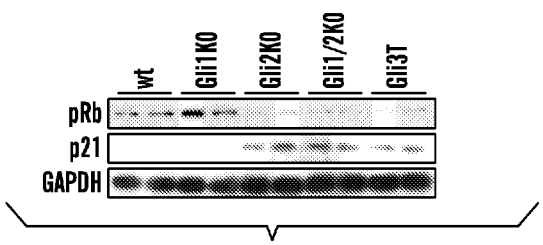

FIGS. 21A-21C show conditional knockout of Gli2 or overexpression of the Gli3 repressor in Gli1 cells induces a myofibroblast specific cell-cycle arrest. Wildtype littermates, Gli1 KO, Gli2KO, Gli1/2KO and Gli3T mice (n=5 each) received tamoxifen, underwent UUO surgery and were euthanized at day 3 following surgery. BrdU was administered 3 hours before sacrifice. Data of UUO kidneys after co-staining for BrdU (S-Phase), phospho-histone H3 (p-H3, G2/M Phase) and alpha smooth muscle actin (α-SMA/myofibroblasts) is not shown. FIG. 21A Cell counting and quantification of myofibroblasts cell cycle (S-phase=α-SMA+/BrdU+; G2/M phase=α-SMA+/p-H3+; G0/G1phase=αSMA+-SMA+/BrdU+-α-SMA+p-H3+). FIG. 21B. Cell counting and quantification of tubular epithelial cell-cycle (S-phase=tubule epithelial cells-TE/BrdU+; G2/M phase=TE/p-H3+; G0/G1phase=TE-TE/BrdU+-TE/p-H3+). FIG. 21C Western blot of whole kidney lysates for phosphorylated retinoblastoma (pRb) and p21. *p<0.05, **p<0.001 versus wt, #p<0.05, ##p<0.001 versus Gli1KO, by one way ANOVA with posthoc Bonferroni, data presented as mean±SEM, all scale bars 50 μm, inserts 25 μm.

Figure 22G:
Figure 22H:
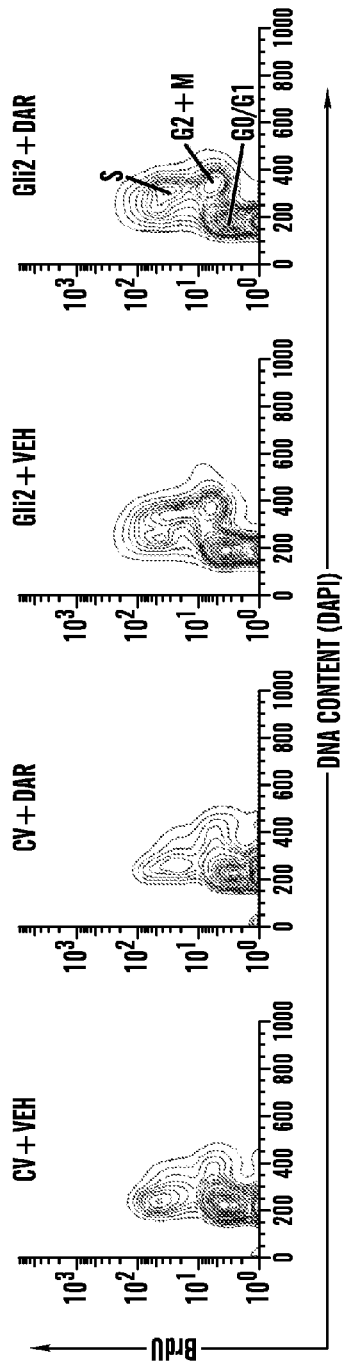
Figure 22I:
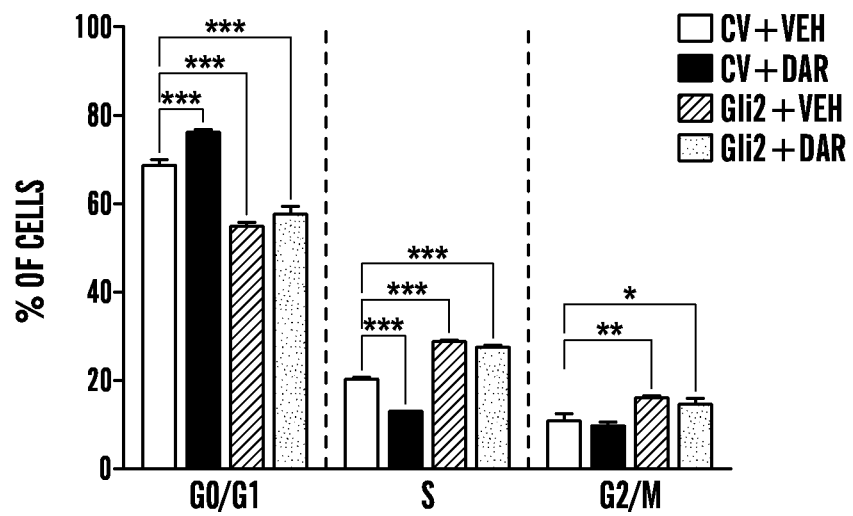
Figure 22J:
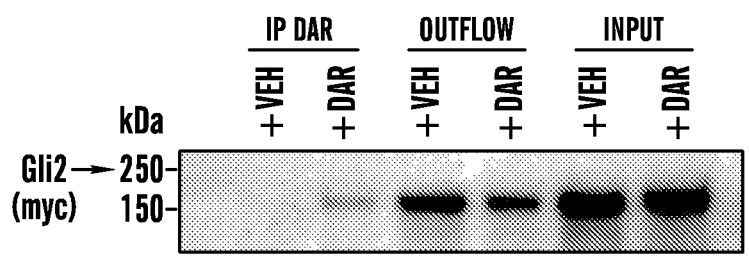

FIGS. 22A-22J. The novel organic darinaparsin acts via binding to Gli2 with subsequent reduced Gli protein levels and induction of a cell-cycle arrest in MSC-like cells. FIGS. 22A-22B Darinaparsin (DAR) induces a G0/G1 cell cycle arrest in mouse 10T1/2 cells (BrDU, Bromdesoxyuridin, S-Phase; 7AAD,7-aminoactinomycin, DNA content). FIG. 22C. Representative western blots of whole cell-lysate from 10T1/2 cells treated with DAR or vehicle (VEH) in presence or absence of sonic hedgehog (Shh). FIGS. 22D-22G Overexpression of full-length Gli2 (HA-tag) by retroviral delivery resulted in a significant upregulation of Gli2 and increased downstream readouts of the hedgehog pathway Gli1 and patched 1 (Ptch1) when compare to control virus (CV) transduced cells. FIGS. 22H-22I. Retroviral expression of Gli2 rescues the cell cycle effect of darinaparsin and drives proliferation of 10T1/2 cells. (CV-control virus; DAPI 4',6-diamidino-2-phenylindole, DNA content, data of n=3 biological replicates). FIG. 22J 293T cells were transfected with full length Gli2-myc and treated with darinaparsin (DAR) or vehicle (VEH). Glutathione-S-transferase (GST) agarose beads were added to the cell lysate to bind the glutathione moiety of DAR and were able to pull down Gli2 (myc) indicating DAR binding to Gli2 (IP-DAR). *p<0.05, p<0.01, *p<0.001, A by t-test, B-F by t-test, I by two way ANOVA with posthoc Bonferroni, data presented as mean±SEM.

Figure 23B:
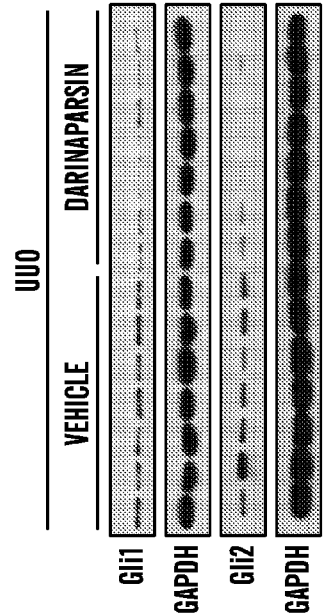
Figure 23E:
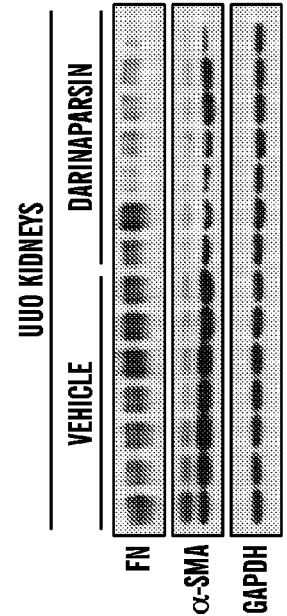
Figure 23A:
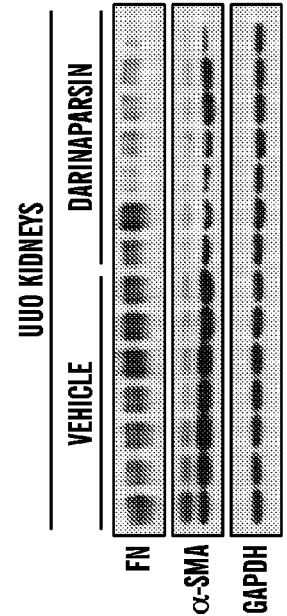
Figure 23D:
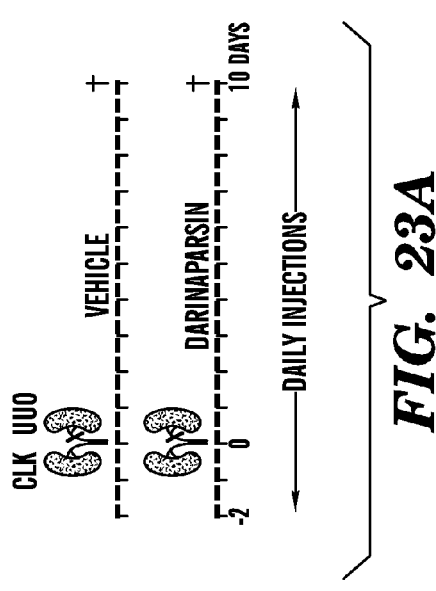
Figure 23C:
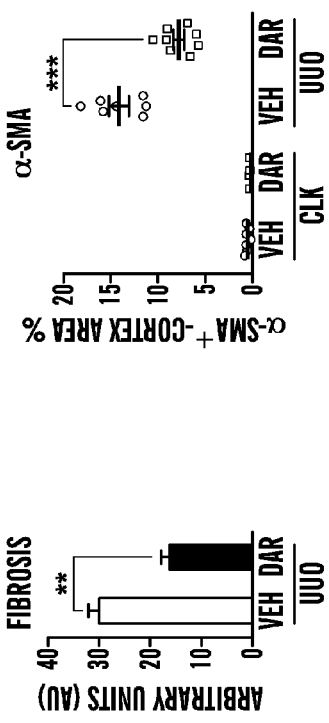
Figure 23F:
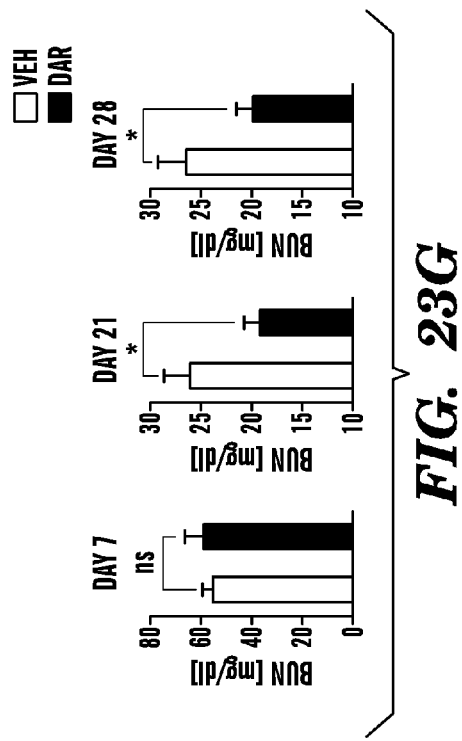
Figure 23G:
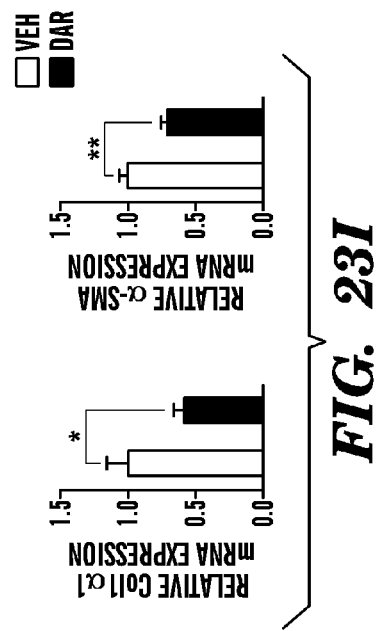
Figure 23H:
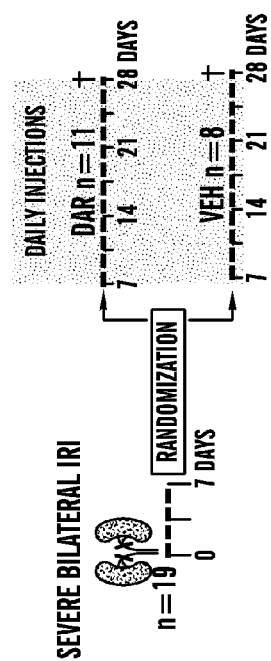
Figure 23I:
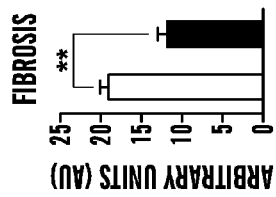

FIGS. 23A-23I show data indicating that darinaparsin treatment ameliorates renal interstitial fibrosis after unilateral ureteral obstruction and AKI to CKD progression after severe ischemia reperfusion injury. FIG. 23A shows data from wildtype mice were treated with darinaparsin (50 mg/kg, n=9) or vehicle (normal saline, n=7) as indicated, and underwent unilateral ureteral obstruction (UUO) surgery and were sacrificed at day 10 after surgery. FIG. 23B. Representative western blots of whole UUO kidney lysates for Gli1 and Gli2. FIG. 23C. Representative trichrome stained and alpha smooth muscle actin (α-SMA) immunostained UUO kidneys. FIGS. 23C-23D. Quantification of interstitial fibrosis and α-SMA+ surface area. FIG. 23E. Representative western blot of whole UUO kidney lysates for fibronectin and α-SMA. FIG. 23F. Wildtype mice underwent severe bilateral ischemia reperfusion injury (IRI) and were randomized based on their day 1 and 7 blood urea nitrogen (BUN) to darinaparsin (DAR) or vehicle treatment (VEH). FIG. 23G. BUN measurement at randomization (day 7) and after 14 or 21 days of treatment. FIG. 23H. Quantification of interstitial fibrosis. FIG. 23I. Relative mRNA expression for Collagen IαI, and α-SMA. *p<0.05, p<0.01, *p<0.0 01 vs vehicle treated mice, by t-test, data is presented as mean±SEM, all scale bars 50 μm.

Figure 24A:
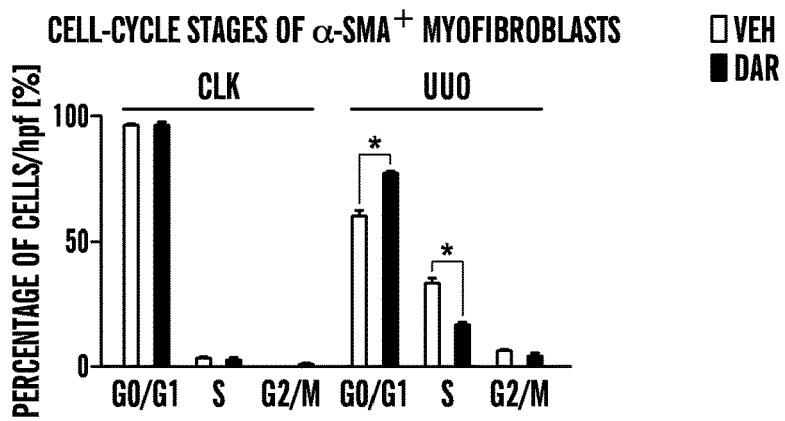
Figure 24B:
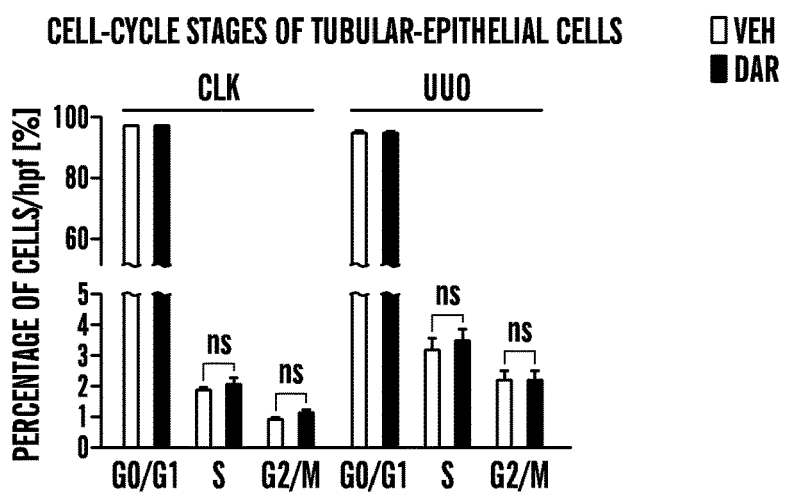
Figure 24C:
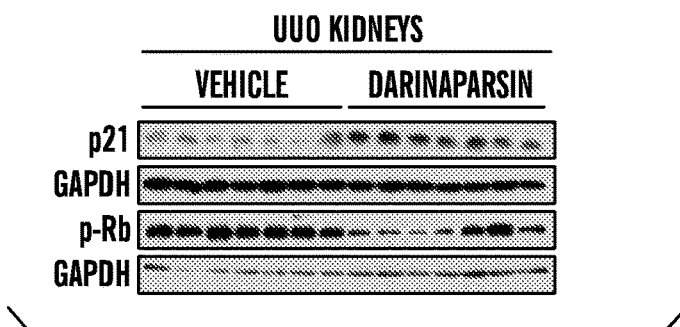

FIGS. 24A-24C shows that darinaparsin induces a myofibroblast specific cell-cycle arrest while it does not affect the cell-cycle of tubular-epithelial cells. FIG. 24A-24B C57Bl/6J mice were treated with darinaparsin (50 mg/kg, n=6) or vehicle (n=6) starting 2 days prior to unilatereal ureteral obstruction surgery and sacrified at day 3 after surgery. Bromdesoxyuridin (BrDU) was injected (100 mg/kg) 3 hours prior to sacrification. Co-staining of sections from the UUO and contralatereal kidney (CLK) for BrDU (cells in S-Phase), phospho histone H3 (p-H3, G2/M Phase) and alpha-smooth muscle actin (α-SMA) allowed quantification of cell-cycle stages for interstitial myofibroblasts (α-SMA) and tubular epithelial cells. Darinaparsin treatment resulted in a specific G0/G1 cell-cycle arrest of interstitial myofibroblasts in UUO kidneys (FIG. 24A), whereas the cell-cycle distribution of tubulo-epithelial cells was not affected (FIG. 24B). FIG. 24C Representative Western blot of whole UUO kidney lysates for the cyclin dependent kinase inhibitor p21/Cip1 and phosphorylated retinoblastoma (p-Rb), (CLK kidneys are shown in Supplementary Figure S4). ***p<0.001 by t-test data is presented as mean±SEM, all scale bars 60 μm).

Figure 25H:
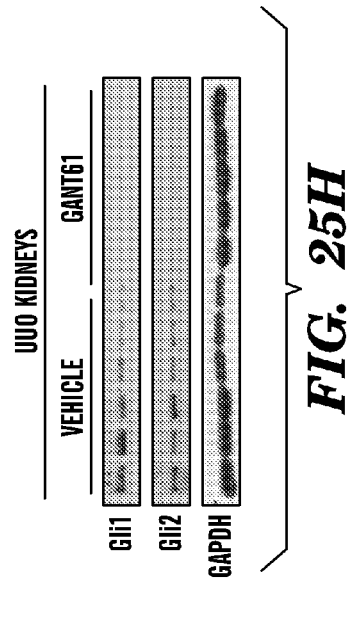
Figure 25G:
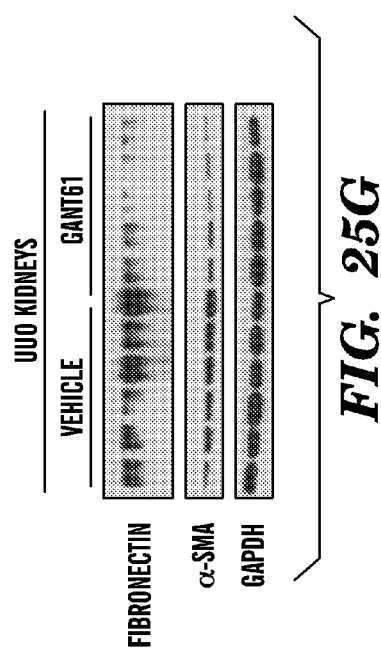
Figure 25J:
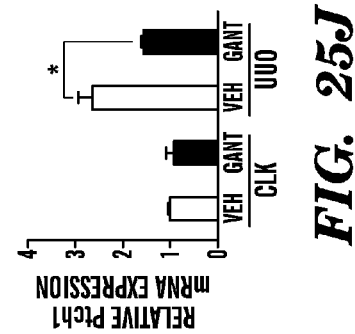
Figure 25I:
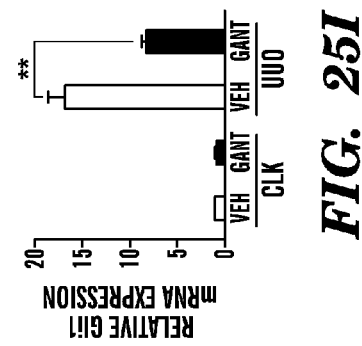

FIGS. 25A-25J show targeting of Gli proteins by GANT61 ameliorates renal fibrosis following unilateral ureteral obstruction. FIG. 25A To test whether specific inhibition of Gli ameliorates renal fibrosis mice were subjected to unilateral ureteral obstruction (UUO) surgery and treated on indicated days (arrows) with either GANT61 or vehicle (ethanol/corn oil 1/4). FIGS. 25B-25C Trichrome staining and scoring for interstital fibrosis in UUO kidneys revealed significantly less fibrosis in GANT61 treated mice. FIGS. 25D-25F Determination of mRNA expression demonstrated a significant lower expression of the fibrotic readouts (FIG. 25D) collagen-1-alpha-1 (Col1α1), (FIG. 25E) alpha smooth muscle actin (α-SMA) and (FIG. 25F) fibronectin in the unilateral ureteral obstruction (UUO) kidneys of GANT61 (GANT) treated animals when compared to vehicle (VEH) treated animals. FIGS. 25G-25H. Representative western blots from whole UUO kidney lysate for fibronectin, α-SMA, Gli1 and Gli1. FIGS. 25I-25J. Gant61 treatment resulted in significant reduction of the increased mRNA expression of hedgehog pathway readouts Gli1 and Ptch1 following UUO. $*p<0.05$, $p<0.01$, $*p<0.001$, by t-test, data presented as mean±SEM, Scale bars 100 μm.

Figures 26A, 26B:
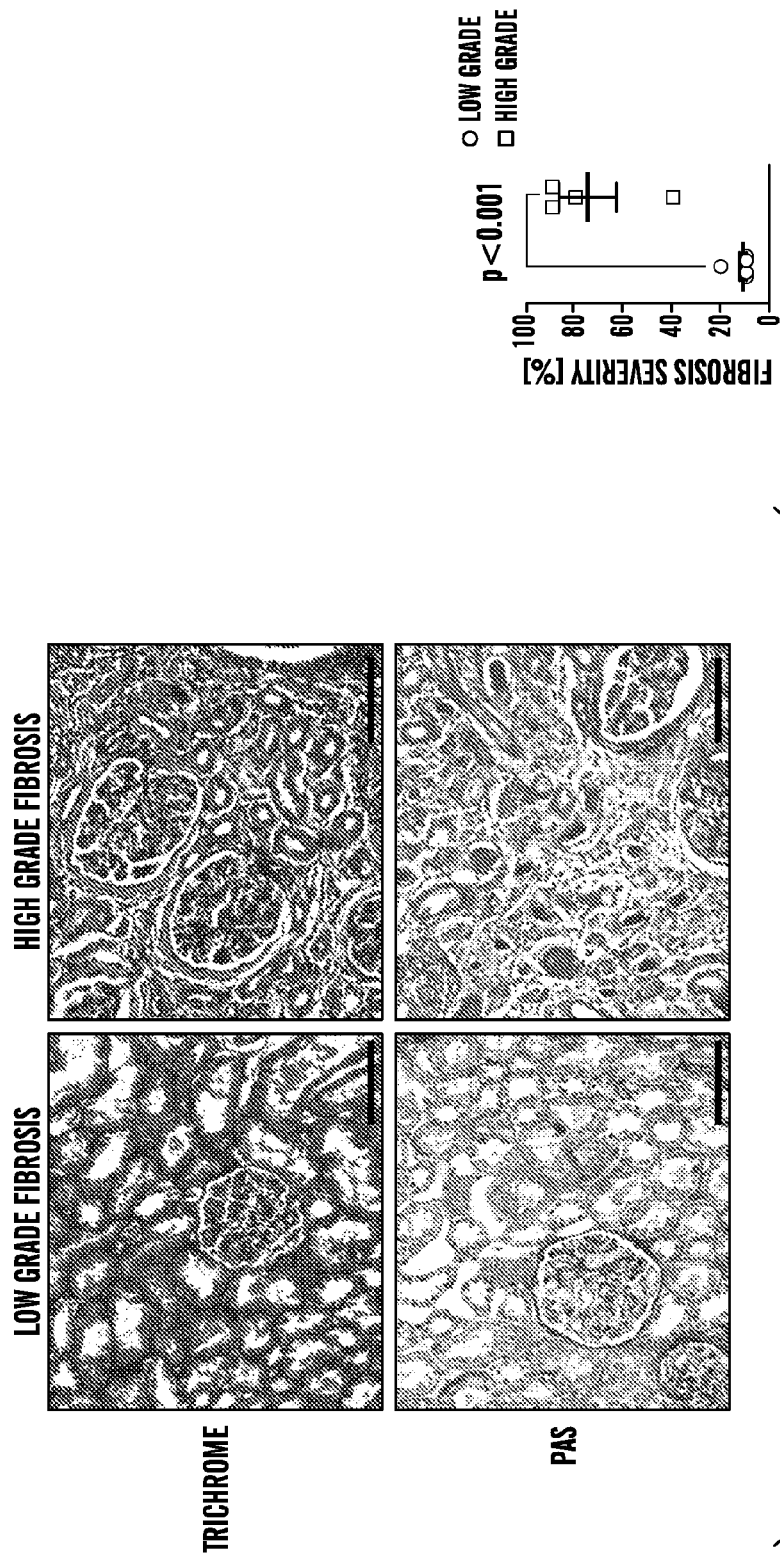

FIGS. 26A-26D show expression of Gli in human kidney fibrosis. FIGS. 26A-26B. Representative images and scoring of human kidney specimen for the degree of interstitial fibrosis. (PAS, Periodic acid-Schiff). FIG. 26C. Relative mRNA expression of fibrotic readouts collagen1α1 (Col1a1), fibronectin (FN) and alpha smooth muscle actin (α-SMA). FIG. 26D. Relative mNRA expression of Gli1, Gli2 and patched1 (Ptch1). p-value as indicated by t-test, data presented as mean±SEM, Scale bars 100 μm.

DETAILED DESCRIPTION

The methods provided herein are based, in part, on the discovery that mesenchymal stem cells and myofibroblast progenitor cells each express the marker Gli-1. Accordingly, methods are provided herein for the use of Gli-1 as a specific marker for myofibroblast progenitor cells, thereby permitting the diagnosis of early stages of fibrosis prior to the onset of organ failure. Also provided herein are methods of isolating Gli-1+ cells for e.g., use in high-throughput screening of compounds for the treatment or prevention of fibrosis. In another aspect, provided herein are methods of treating or preventing fibrosis (e.g., kidney fibrosis) in a subject by administering a Gli inhibitor, particularly a Gli-2 inhibitor or a Gli-1/Gli-2 inhibitor.

Definitions

As used herein, the term "comprising" means that other elements can also be present in addition to the defined elements presented. The use of "comprising" indicates inclusion rather than limitation. For example, in the context of the present application, a metagene comprising a set of markers means a metagene wherein at least the set of indicated markers are included.

As used herein the term "consisting essentially of" refers to those elements required for a given embodiment. The term permits the presence of additional elements that do not materially affect the basic and novel or functional characteristic(s) of that embodiment of the invention. For example, in the context of the present application, a metagene consisting essentially of a set of markers means that the marker set includes the set of markers that have been determined to form the metagene but can include one or more markers that are not used in the calculations for the metagene value but are rather used as controls for background, or positive or negative expression or otherwise added to increase the accuracy of the assay but without including additional markers to the calculation of the metagene value.

The term "consisting of" refers to compositions, methods, and respective components thereof as described herein, which are exclusive of any element not recited in that description of the embodiment. For example, in the context of the present application, the metagene consisting of markers would mean that only the named markers are included in the metagene. The assay may still comprise other markers that may be needed for calculating the metagene value, such as markers for determining the background or markers that are used to control function of the assay or as positive or negative controls or to determine the normalizing expression background.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Michael R. Green and Joseph Sambrook, Molecular Cloning: A Laboratory Manual (4th ed.), Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the Invention

Embodiments of the present disclosure are based on the identification of a novel marker for mesenchymal stem cells (MSCs), myofibroblast expansion, and interstitial fibrosis. This marker is Gli1, a transcription factor in the hedgehog pathway. The inventors found a stromal cell population in kidney that expresses Gli1, together with the other markers typical for an MSC signature: CD44+, CD29+, Sca1+, CD105+, CD45−, CD34− and CD31−. In addition, the inventors found that this Gli1+MSC population contributes to interstitial homeostasis during aging and the population also differentiates into myofibroblasts after injury resulting in myofibroblast expansion and interstitial fibrosis where there is an increase in the number of Gli1+ expressing cells. Therefore, the Gli1 marker is useful for isolation, purification and identification of MSCs, for the detection of myofibroblast expansion and interstitial fibrosis, for the surveillance for myofibroblast expansion and interstitial fibrosis during injury, for monitoring progression or remission of fibrosis during a treatment regiment, and also for drug and small molecule screening for therapeutics that can modulate myofibroblast expansion and interstitial fibrosis, wherein the modulation can be inhibitory or stimulatory.

Accordingly, in one embodiment, provided herein is a method of isolating or detecting or identifying nascent mesenchymal stem cells (MSCs) in an adult tissue, the method comprising contacting a tissue or a population of cells derived from a tissue with an agent that specifically binds to Gli1.

In another embodiment, provided herein is a method of isolating nascent mesenchymal stem cells (MSCs) in an adult tissue comprising isolating Gli1 expressing positive cells.

In one embodiment, provided herein is a method of detecting myofibroblast and/or myofibroblast expansion in an adult tissue, the method comprising contacting a tissue or a population of cells derived from the adult tissue with a first agent that specifically binds to Gli1 and a second agent that specifically binds to alpha-smooth muscle actin.

In one embodiment, provided herein is a method of detecting myofibroblast and/or myofibroblast expansion in an adult tissue comprising detecting for an increase in Gli1 expression and/or an increase in Gli1 and alpha-smooth muscle actin expressions in the tissue.

In one embodiment, provided herein is a method of detecting myofibroblast and/or myofibroblast expansion in an adult tissue comprising detecting for an expansion of or an increase in Gli1+ cells or Gli+/α-SMA+ in the tissue.

In one embodiment, provided herein is a method of detecting myofibroblast and/or myofibroblast expansion in an adult tissue comprising detecting Gli1positive and alpha-smooth muscle actin positive expressing cells.

In one embodiment, provided herein is a method of detecting or monitoring for the induction of tissue fibrosis in an organ, the method comprising: providing a sample of tissue from an organ that is suspected of having tissue fibrosis, detecting for myofibroblasts or Gli1positive and alpha-smooth muscle actin positive expressing cells in the organ; and identifying a presence of fibrosis in the organ when there is a detectable amount of myofibroblasts compared to a reference.

In one embodiment, provided herein is a method of detecting or monitoring for the induction of tissue fibrosis in an organ, the method comprising providing a sample of tissue from an organ that is suspected of having tissue fibrosis; contacting the tissue or a population of cells derived from the tissue with an agent that specifically binds to Gli1; measuring a level of Gli1 expression in the tissue or a population of cells derived from the tissue; comparing the measured level of Gli1 expression with a reference; and identifying a presence of fibrosis in the organ when there is an increase in Gli1 expression over the reference or identifying an absence of fibrosis in the organ when there is a decrease or no difference in Gli1 expression compared to the reference.

In one embodiment, provided herein is a method of monitoring the progression of tissue fibrosis in an organ from an individual, the method comprising: providing a first sample of tissue at a first time point from the organ that is having tissue fibrosis; determining the level of Gli1 expression in the first sample; providing a second sample of tissue at a second time point from the same organ that is having tissue fibrosis, the first time point being before the second time point; determining the level of Gli1 expression in a second sample; comparing the levels of Gli1 from the time points with a reference Gli1 level; and assessing that tissue fibrosis in an organ is regressing where the levels of Gli1 at the second time point is lower than the reference Gli1 level, or assessing that tissue fibrosis in an organ is progressing where the levels of Gli1 at the second time point is higher than the reference Gli1 level.

In one embodiment, provided herein is a method of screening for at inhibitor or modulator of fibrosis comprising providing a Gli1 expressing positive cell, contacting the Gli1 expressing positive cell with at least one candidate compound or agent; and measuring the level of expression of Gli1 in the cell in contact with candidate compound or agent.

In one embodiment, provided herein is a method for monitoring treatment efficacy of a subject with pathogenic fibrosis or chronic fibrosis, the method comprising: (a) determining, from a biological sample obtained from a subject at a first time-point, a level of Gli1; (b) administering treatment to the subject; (c) determining a level of Gli1 in a sample obtained from said subject at a second time-point; and (d) comparing the level Gli1 at the second time-point with the level of Gli1 at the first time-point.

In one embodiment of any method, the method further comprises determining the level of α-SMA in the first and second points, and also comparing the time level of α-SMA from the second time point with that of the first time point.

In one embodiment of any method, wherein a decrease in the level of Gli1 and/or a-SMA at the second time-point indicates the treatment is efficacious for the subject, and wherein an increase in the level of Gli1 and/or a-SMA at the second time-point indicates the treatment is not efficacious for the subject.

In one embodiment, provided herein is a use of a Gli inhibitor for the treatment or prevention of fibrosis.

In one embodiment, provided herein is a use of darinapasin and/or GANT61 for the treatment or prevention of fibrosis.

In one embodiment, provided herein is a pharmaceutical composition comprising darinapasin and/or GANT61 and a pharmaceutically acceptable carrier for the treatment or prevention of fibrosis.

In another embodiment, provided herein is a use of a Gli inhibitor for the manufacture of medicament for the treatment or prevention of fibrosis. In another embodiment, provided herein is a use of darinapasin and/or GANT61 for the manufacture of medicament for the treatment or prevention of fibrosis.

In one embodiment, the Gli inhibitor is a Gli1 specific or a Gli 2 specific inhibitor. In another embodiment, the Gli inhibitor targets both Gli 1 and Gli 2. In some embodiments, the Gli inhibitor is darinapasin or GANT61.

Gli-1 Expression in Cells

Gli1 was discovered as a unique marker to isolate solid organ resident stem cells and bone marrow derived mesenchymal stem cells, and also myofibroblasts in fibrotic or diseased tissue. Therefore, Gli1 is a specific marker of mesenchymal stem cells in all tissue types as well as myofibroblasts in fibrotic disease. The inventors show that Gli1 labels mesenchymal stem cells in vivo from multiple different solid organs such as heart, liver, kidney, and from the bone marrow. The inventors also successfully isolated and cultured these Gli1+ expressing cells and show that they have the capacity to differentiate into multiple lineages including, e.g., adipocytes, osteocytes and chondrocytes, indicating that these Gli1+ cells are mesenchymal stem cells resident in solid organs and the bone marrow. In normal tissue, the Gli1 marker is found in quiescent perivascular cells.

Additionally, Gli1+ is expressed in a resident adult multipotent stem cell population that gives rise to myofibroblasts across different organs. During induction of tissue fibrosis in multiple organs (kidney, heart, and lung) these Gli1+ cells transform into pathogenic myofibroblast cell types. There are currently no specific markers for the identification of myofibroblasts in fibrotic disease. The myofibroblasts are the cells that contribute to the fibrosis process. Identification of myofibroblasts is typically performed with a combination of markers or with markers that are nonspecific, i.e., they have concomitant expression in non-myofibroblasts cell types within the same tissue sample. Using Gli1 as a marker allows simple identification and isolation of myofibroblasts. This discovery will permit investigators of chronic or pathogenic fibrosis to specifically label and isolate these stem cells (pre-disease state) as well as the differentiated and pathogenic myofibroblasts. This, in turn, represents a very useful method advancing the understanding of myofibroblasts in order to develop new treatments for fibrotic disease in multiple organ types. Currently there are no approved treatments for fibrotic disease in the United States, and identifying novel targets directly on the pathological cell type (myofibroblasts) is essential in advancing drug development.

The inventors also identified Gli1 expression specifically in traditional mesenchymal stem cells (MSCs) located in bone marrow. As with myofibroblasts there is no known unique and specific marker for bone marrow MSCs. These cells are also identified by probing for a panel of markers that are expressed at varying percentages in MSC. The specificity of these markers for MSCs is also still debated. Interestingly, bone marrow MSCs have been theorized as the cells that cause myelofibrosis. Without wishing to be bound by theory, Gli1 marks cells in solid organ and marrow that contribute to the fibrotic disease state of each tissue type. Bone marrow MSC are also of current interest because these cells have therapeutic properties and have been shown to resolve inflammation when injected into humans.

The inventors also identified Gli1 is a specific marker for mesenchymal stem (stromal) cells (MSC) in every tissue in the non-disease state; that is healthy tissue. Furthermore in fibrotic disease, such as kidney fibrosis, myocardial fibrosis, liver fibrosis, lung fibrosis, muscle fibrosis, potentially myelofibrosis and vascular sclerosis, Gli1 expression specifically identifies the fibrosis driving cells called myofibroblasts.

In one embodiment of any one method described herein, the adult tissue is in an organ. In one embodiment of any one method described herein, the organ is solid organ. In one embodiment of any one method described herein, the organ is selected from heart, liver, lung, kidney, skin and bone marrow. For example, when the Gli1+ MSCs are to be isolated or purified, a tissue sample can be isolated the selected organ, eg., heart, liver, lung, kidney, skin and bone marrow, from an individual, single cells are separated from the connective tissue, and the single cells can be differentiated on the basis of the expression of Gli1+.

Measuring Gli1 Expression

In one embodiment of any one method described herein, the step of detecting comprises contacting a tissue or a population of cells derived from a tissue with an agent that specifically binds to Gli1. For example, the agent is an antibody against Gli1. Exemplary Gli1 antibodies are available commercially from e.g., SANTA CRUZ BIOTECHNOLOGY (Cat. No. sc-20687), ABCAM (Cat No. ab-49314), and R&D SYSTEMS (Cat. No. BAF-3455).

In one embodiment of any one method described herein, the agent that specifically binds Gli1 is an anti-Gli1 antibody or a fragment thereof.

In one embodiment, the anti-Gli1 antibody is labeled with a selectable and/or detectable marker or label, such as an enzyme, a fluorescent label, a luminescent label, a DNA probe or a bioluminescent label. In one embodiment, the label is via conjugation, that is, the anti-Gli1 antibody is conjugated to a label. Such selectable and/or detectable marker or label facilitates detection, visualization, isolation, and/or purification of Gli+ cells. For example, isolation and purification by fluorescence-activated cell sorting (FACS). By "conjugated" is meant the covalent linkage of at least two molecules.

In one embodiment, the selectable and/or detectable marker or label is for generating a detectable signal include, but are not limited to, a phosphorescent dye, a tandem dye and a particle. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label also includes a "tag" or hapten that can bind selectively to a conjugated molecule such that the conjugated molecule, when added subsequently along with a substrate, is used to generate a detectable signal. For example, one can use biotin as a label and subsequently use an avidin or streptavidin conjugate of horseradish peroxidase (HRP) to bind to the biotin label, and then use a colorimetric substrate (e.g., tetramethylbenzidine (TMB)) or a fluorogenic substrate such as AMPLEX Red reagent (MOLECULAR PROBES, Inc.) to detect the presence of HRP. Numerous labels are known by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS (9th edition, CD-ROM, (September 2002), which is herein incorporated by reference.

In one embodiment of any one method described herein, the step of detecting Gli1 comprises an immune assay. For examples, enzyme-linked immunosorbent assays (ELISAs), enzyme immunoassays (EIAs), radioimmunoassay (RIA), real-time immunoquantitative PCR (iqPCR) and surface plasmon resonance.

For example, the single cells separated from the sample of tissue isolated from the organ of interest can be permeated with detergent, e.g., Triton X-100, and then contacted with the agent that specifically binds Gli1, such as an anti-Gli1 antibody or fragment thereof. FACS can then be used to isolate the Gli1+ cells from the Gli1− cells. The pooled or enriched Gli1+ cells can be a useful research tool for further studies in MSCs and myofibroblasts.

In one embodiment of any one method described herein, the method comprises providing a sample of tissue for detecting Gli1 or contacting with a Gli1 binding protein, such as a Gli1 antibody or fragment thereof.

In one embodiment of any one method described herein, the method comprises dissolution or dissociation of the sample of tissue to provide single cells for detecting or contacting as described herein. In one embodiment, by "dissolution or dissociation" means separating the single cells from the connective tissues in the sample of tissue.

In one embodiment of any one method described herein, the method comprises fixation of the sample of tissue for detecting or contacting.

In one embodiment of any one method described herein, the method comprises permeabilization of the sample of tissue or dissociated single cells for detecting or contacting.

Tissue Dissolution or dissociation, fixation, or permabilization of sample tissues and cells can be performed by any method known in the art, such as digesting with trypsin, collagenase, treating with formaldehyde or detergent such as Triton X-100 or SDS.

Diagnosis of Fibrotic Disease

In one embodiment of any one method described herein, the method further comprises selecting a subject or individual suspected of having tissue fibrosis. The subject may have had an injury to the organ that is known to initiate fibrosis that is known in the art or diseases described herein.

Fibrotic disease can essentially affect any organ. Some of the most common forms of fibrotic disease include (i) idiopathic pulmonary fibrosis, (ii) kidney fibrosis, (iii) myocardial fibrosis, (iv) chronic kidney disease, and (v) end stage renal disease. Each of these forms of fibrotic disease is discussed in more detail below.

Idiopathic Pulmonary Fibrosis (IPF):

IPF affects approximately 200,000-250,000 patients in the US and Europe and carries an extremely poor prognosis: median survival ranges between 2 and 3 years after diagnosis. There is currently only one approved drug to treat IPF, in Europe and Asia, which functions with very modest efficacy. The diagnosis of IPF has continued to increase and more efficacious treatments for this disease are desperately needed; particularly treatments that directly target the cells primarily responsible for driving the formation of scar tissue, the myofibroblasts.

Kidney Fibrosis:

Kidney fibrosis is the common final path of virtually all, progressive kidney diseases leading to chronic kidney disease (CKD) and end-stage renal disease (ESRD). In 2010 over 500,000 people in the US suffered from ESRD and this relatively small group (i.e., <0.2% of the population) accounted for over 29 billion USD of Medicare spending (i.e., 6.7% of total Medicare spending). The prevalence of chronic kidney disease (CKD) in the US increased 20-25% over the past decade and this represents a major ongoing public health issue. Again, therapies are urgently needed, as there are currently no approved medicines that directly target the myofibroblasts that drive the production of fibrotic matrix formation.

Myocardial Fibrosis:

Myocardial fibrosis is the consequence of extracellular cardiac matrix remodeling resulting from pathological processes including ischemia, inflammation, hypertension, diabetes mellitus and end-stage renal disease. In the United States heart failure accounts for approximately $33 billion in yearly healthcare costs, and is the leading hospital discharge diagnosis. Extracellular matrix remodeling due to myocardial fibrosis is involved in many pathophysiologic processes leading to chronic heart failure as dilated or ischemic cardiomyopathy and hypertensive heart failure. Moreover myocardial fibrosis also has an impact on electrical properties of the heart and triggers electric instability. Thus targeting myocardial fibrosis might also effect both incidence and prevalence of arrhythmias as a major health care burden. Similar to fibrosis of the kidney and lung, there are no specific drugs approved to target myofibroblasts in myocardial fibrosis.

Chronic Kidney Disease and End Stage Renal Disease.

Chronic kidney disease (CKD), defined by reduced glomerular filtration rate (GFR), proteinuria or structural kidney disease, is a major medical challenge whose incidence is growing and for which better treatments are needed. The rates of CKD are increasing fastest in persons older than 75-years-old [1]. In 2010 over 500,000 people in the US suffered from end stage renal disease (ESRD) and this group (<0.2% of the population) accounted for a disproportionate share of the 29 billion dollar Medicare budget (6.7% of total Medicare spending) [2].

The connection of myofibroblast expansion and interstitial fibrosis are as follows. CKD is accompanied by substantial changes in renal structure, notably within the kidney interstitial compartment. Interstitium consists primarily of endothelium, pericytes [3] (vascular supportive cells, also called renal fibroblasts in the literature [4]) and macrophages. Structural changes in the interstitium correlate better with loss of function than glomerular changes, in many cases, highlighting the functional importance of this kidney compartment to the parenchyma [5-7]. During chronic injury, the interstitium becomes expanded with increased myofibroblasts. Myofibroblasts are matrix producing interstitial cells that cause fibrosis. They are reactive cells that occur after acute or chronic injury or in pathologic conditions such as cancer [8]. These cells are highly synthetically active and characterized by dense rough endoplasmic reticulum and collagen secretion granules [9]. Myofibroblasts are contractile and express alpha-smooth muscle actin (ct-SMA), which forms bundles of myofilaments, called stress fibers, promoting strong contractile force generation [10, 11]. In addition to ct-SMA, plasma membrane fibronectin and vimentin are also myofibroblast markers. In kidney, myofibroblasts are defined by Collagen-1ct1 expression, consistent with the matrix-secretory function of these cells [12].

There is a relationship of myofibroblasts to vascular loss in CKD. The renal vasculature plays a critical role in CKD, which is characterized by peritubular capillary loss causing chronic hypoxia, inflammation and fibrosis. Peritubular capillary loss is seen in chronic allograft nephropathy [13] as well as chronic glomerulopathies [14], and it has been proposed to be the final common pathway for fibrotic renal disease [15, 16]. Although the kidney does possess an angiogenic response, the peritubular capillary network is particularly susceptible to damage, and it is unable to regenerate capillary density after injury [17, 18]. Myofibroblast proliferation in CKD promotes peritubular capillary destabilization through depletion of pericytes, and loss of vasculotrophic factors. The resulting chronic low-grade hypoxia sets up a feedback loop of hypoxia-parenchymal damage-capillary loss and increased fibrosis.

Myofibroblast Progenitors and Controversy.

There is intense interest in understanding exactly where myofibroblasts derive, because this knowledge will guide attempts to ablate these cells and forms the logical basis for anti-fibrotic therapeutic strategies. Eradication of pathological myofibroblasts will not only halt scar secretion directly, but will also prevent loss of microvasculature, reducing hypoxia and promoting parenchymal health. For some time, myofibroblasts had been thought to arise from epithelial cells, through epithelial to mesenchymal transition (EMT) [19, 20]. However, the inventors and others in more recent publications provide strong evidence against EMT as a source of myofibroblasts in liver [21], kidney [22] and lung [23]. By contrast, the inventors previously provided evidence that myofibroblasts derive solely from resident kidney pericytes and perivascular fibroblasts using lineage tracing methods [22]. These results did not distinguish between the possibility that all kidney pericytes and perivascular fibroblasts have the capacity to differentiate into myofibroblasts, or whether a subset represents the true progenitor population.

Despite these findings, the possibility that bone marrow might serve as an additional pool for circulating myofibroblast progenitors remains unresolved. Although bone marrow transplantation studies of collagen-1α1 driven GFP suggest that bone marrow-derived cells contribute only a very small fraction of myofibroblasts in kidney fibrosis originate from the bone marrow [12], other studies have drawn the opposite conclusion. LeBleu et al. recently reported that up to 35% of kidney myofibroblasts derive from bone marrow using bone marrow transplantation of ctSMA-RFP transgenic donor cells. The authors further propose that these bone-marrow derived myofibroblast progenitors are mesenchymal stem cells (MSC) with trilineage differentiation capacity, and that they are non-dividing [24]. Although the authors failed to prove that transplanted ctSMA-RFP marrow-derived MSC engrafted or that kidney-homed ctSMA-RFP+ cells expressed other myofibroblast markers, this result has thrown the field into uncertainty regarding the true role of bone marrow derived cells in kidney fibrosis.

In the search for the origins of the myofibroblast, the inventors noted that the Gli1+ resident kidney stromal cells expand by 20-fold during unilateral ureteral obstruction-induced renal fibrosis (UUO), whereupon they acquire α-SMA expression during myofibroblastic differentiation. Therefore, the Gli1+ MSCs are the source of myofibroblast and fibrosis. Accordingly, the increase in Gli1+ marker is an indication of myofibroblastic expansion and induction, which is an indication of the presence of the fibrosis process.

In one embodiment of any one method described herein, the method further comprises identifying a presence of fibrosis in the organ when there is an increase in Gli1positive expressing cells over the reference or identifying an absence of fibrosis in the organ when there is a decrease or no difference in Gli1positive expressing cells compared to the reference.

In one embodiment of any one method described herein, the method further comprises measuring the level of alpha-smooth muscle actin in the same tissue or a population of cells derived from the tissue and comparing with the measured level of alpha-smooth muscle actin with a reference. Exemplary alpha-smooth muscle actin antibodies are available commercially from e.g., SIGMA-ALDRICH (Cat. No. A2547), ABCAM (Cat No. ab-56914), and PIERCE ANTIBODIES (Cat. No. PA5-19465).

In one embodiment of any one method described herein, the method further comprises identifying a presence of fibrosis in the organ when there is an increase in Gli1positive and alpha-smooth muscle actin positive expressing cells over the reference or identifying an absence of fibrosis in the organ when there is a decrease or no difference in Gli1positive and alpha-smooth muscle actin positive expressing cells compared to the reference.

In one embodiment of any one method described herein, the method further comprises measuring the level of alpha-smooth muscle actin in the same first and second samples and comparing with the measured level of alpha-smooth muscle actin with a reference.

In one embodiment of any one method described herein, the reference is the level of Gli1+ expression or the average level of alpha-smooth muscle actin expression in normal tissues of the same organ or tissue type. In one embodiment, the reference is the average level of Gli1+ expression or the average level of alpha-smooth muscle actin expression in normal tissue of the same organ or tissue type. For example, a population of healthy individuals with no ongoing chronic fibrosis such as those known in the art and those described herein are selected. Samples of select organs and/or tissues are taken and analyzed for the presence and level of Gli1+ expression or alpha-smooth muscle actin expression. The average and standard deviation of the levels obtained are computed by known statistical methods.

In one embodiment of any one method described herein, the increase is an increase of at least 2-fold over that of the reference level for the respective marker, i.e., Gli1+ or α-SMA, from the respective tissue or organ. In other embodiments, the increase is at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least one standard deviation, at least two standard deviations over that of the reference level for the respective marker, i.e., Gli1+ or α-SMA, from the respective tissue or organ.

In another embodiment of any one method described herein, the increase is an increase of the level of the respective marker, i.e., Gli1+ or α-SMA, from the second time point of at least 5% over that of the level for the respective marker from the first time point obtained from the respective tissue or organ. In other embodiments, the increase is at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or more over that of the level for the respective marker from the first time point obtained from the respective tissue or organ.

In one embodiment of any one method described herein, the decrease is a decrease of the level of the respective marker, i.e., Gli1+ or α-SMA, from the second time point of at least 5% over that of the level for the respective marker from the first time point obtained from the respective tissue or organ. In other embodiments, the increase is at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or more over that of the level for the respective marker from the first time point obtained from the respective tissue or organ.

In one embodiment of any one method described herein, the comparison of the Gli1+ or α-SMA expression in the sample of tissue taken at the first and second time point gives an indication of the progression or remission of fibrosis in that tissue type or the organ from which the tissue sample were obtained from.

For example, the individual has been previously diagnosed as having chronic fibrosis. The Gli1+ or α-SMA expression level for the first time point is increased over that of a reference. The individual is being treated for the fibrosis. In one embodiment, the reference is that of healthy individuals who do not have chronic fibrosis in the respective organ or tissue. When the Gli1+ or α-SMA expression level is analyzed at a later second time point, if there is continued progression of the fibrosis without any reduction, the level of expression would be increased over that of the first time point, and would also be increased over that of the reference.

In one embodiment, when the Gli1+ or α-SMA expression in the second time point is increased or higher than the first time point or higher or increased over the reference, this indicates that fibrosis is currently present and/or progressing, that is there is no reduction in the fibrotic condition in the individual.

On the other hand, when the Gli1+ or α-SMA expression level is analyzed at a later second time point, if there is maintenance of the fibrosis status without any reduction, the level of expression would be approximately the same of that of the first time point, and would also be increased over that of the reference. If the individual is being treated, then, the increased expression indicates that the treatment is not effective. Re-evaluation of the treatment regime should be performed.

On the other hand, when the Gli1+ or α-SMA expression level is analyzed at a later second time point, if there is a reduction of the fibrosis status, the level of expression would be decreased or less than that of the first time point. The levels can also still be increased over that of the reference. This indicates that there is still some fibrosis in the individual but there is a decrease and the treatment is effective.

Alternatively, the level of expression would be decreased or less than that of the first time point and is more or less the same of that of the reference or is closer towards that of the reference. This indicates that the fibrosis is in remission in the individual and the treatment is effective. For such an individual, periodic monitoring for the re-emergence of fibrosis should be performed.

Accordingly, in one embodiment, provided herein is a method for monitoring treatment efficacy of a subject with pathogenic fibrosis or chronic fibrosis, the method comprising: (a) determining, from a biological sample obtained from a subject at a first time-point, a level of Gli1; (b) administering treatment to the subject; (c) determining a level of Gli1 in a sample obtained from said subject at a second time-point; and (d) comparing the level Gli1 at the second time-point with the level of Gli1 at the first time-point.

In one embodiment of any method, the method further comprises determining the level of α-SMA in the first and second points, and also comparing the time level of α-SMA from the second time point with that of the first time point.

In one embodiment of any method, wherein a decrease in the level of Gli1 and/or α-SMA at the second time-point indicates the treatment is efficacious for the subject, and wherein an increase in the level of Gli1 and/or α-SMA at the second time-point indicates the treatment is not efficacious for the subject.

In one embodiment of any method, the first and second time points are 1 month apart. In other embodiments of any method, the first and second time points are 2, 3, 4, 5, 6 months or 1 year apart.

As used herein "pathogenic fibrosis or chronic fibrosis" refers to undesired prolonged or excessive fibrosis that results in organ or tissue failure. Examples include but are not limited to pulmonary fibrosis, hepatic fibrosis, kidney fibrosis, myocardial fibrosis (including uremic cardiomyopathy, congestive heart failure, left ventricular hypertrophy and diastolic heart failure) and myelofibrosis.

In one embodiment, provided herein is a method of monitoring the re-emergence of tissue fibrosis in an organ from an individual, the method comprising: providing a first sample of tissue at a first time point from the organ that is having tissue fibrosis; determining the level of Gli1 and/or α-SMA expression in the first sample; providing a second sample of tissue at a second time point from the same organ that is having tissue fibrosis, the first time point being before the second time point; determining the level of Gli1 and/or α-SMA expression in a second sample; comparing the levels of Gli1 and/or α-SMA from the two time points; and assessing that tissue fibrosis in an organ is re-emerging where the levels of Gli1 and/or α-SMA at the second time point is increase over that of the first time point, or assessing that tissue fibrosis in an organ is re-emerging where the levels of Gli1 and/or α-SMA at the second time point is higher than the reference of the respective marker for the respective organ or tissue. In one embodiment, this individual has recovered from fibrosis and has had normal Gli1 and/or α-SMA levels that are comparable to the respective reference level. Any increase of these markers over the respective reference levels would indicate re-emergence of fibrosis in the individual.

In one embodiment of any one method described herein, the method further comprises treating or inhibiting the fibrosis by administering at least an anti-fibrosis treatment when the presence of fibrosis in the organ is identified.

In one embodiment of any one method described herein, the method further comprises selecting an individual suspected of developing or at risk of developing fibrosis.

In one embodiment of any one method described herein, the method further comprises selecting an individual who is having fibrosis.

In one embodiment of any one method described herein, the method further comprises continuing treating or inhibiting the fibrosis by administering at least an anti-fibrosis treatment when the presence of fibrosis in the organ is identified.

In one embodiment of any one method described herein, the method further comprises comparing the measured level of Gli1 expression with a reference wherein the measured level of Gli1 expression is reduced compared to the reference indicate that the candidate compound or agent is a likely inhibitor of tissue fibrosis.

In some embodiments of any method described, the cells of the organ under study can be dissociated and FACS purification protocol can be used to isolate the cells, e.g., kidney cells for studying kidney fibrosis. This involves mincing of kidney followed by disperse digestion. FACS offers the advantage of quantitative measurement of cell number in the tissue, as well as the ability to rigorously define cell surface profiles. FACS will also be used to isolate the Gli1+ cells for transplantation under the kidney capsule.

In one embodiment of any method described, the method further comprises selecting a subject who has exhibited tissue fibrosis is an organ or a subject who is at risk of developing tissue fibrosis is an organ. For example, a subject who has suffered a traumatic injury in an organ, or one with chronic organ failure.

In one embodiment of the method described, the method further comprises selecting a subject who has exhibited tissue fibrosis previously in another organ or tissue.

In one embodiment of the method described, the method further comprises administering at least one treatment for tissue fibrosis. Any treatment methods for fibrosis and compositions for the treatment of tissue fibrosis known in the art can be administered, for example, those described in US Patent Application Publication No: 2005/017665, entitled "Polymer compositions and method for their uses" in paragraphs 77-338, such as angiogenesis inhibitors and cathepsin inhibitors.

In one embodiment of any method described, the organ or tissue being tested for tissue fibrosis is kidney.

In one embodiment of any method described, kidney fibrosis is assessed by performing a serum BUN and creatinine analyses as well as assessing the glomerular filtration rate via 24 h urine collection using assays standard.

In one embodiment, provided herein is a method for treatment of a subject with pathogenic fibrosis or chronic fibrosis, the method comprising: determining a level of Gli1 from a biological sample obtained from an organ or tissue of a subject; and administering treatment to the subject when the level of Gli1 is over or increased the level of a reference Gli1 in the respective organ or tissue.

In one embodiment, the method further comprises determining a level of Gli1 in a sample obtained from the subject after the start of treatment and comparing the level Gli1 with the level of Gli1 obtained prior to the start of treatment to determine the efficacy of the treatment.

In one embodiment of any method, the method further comprises determining the level of α-SMA prior to and after the start of treatment, and also comparing the time level of α-SMA from prior to and after the start of treatment to determine the efficacy of the treatment.

In one embodiment of any method, wherein a decrease in the level of Gli1 and/or α-SMA after the start of treatment indicates the treatment is efficacious for the subject, and wherein an increase in the level of Gli1 and/or α-SMA after the start of treatment indicates the treatment is not efficacious for the subject.

In one embodiment of any method, the method further comprises determining the level of α-SMA in the contacted cells.

Screening Assays

In one embodiment, provided herein is a method of screening a candidate agent for activity as an inhibitor or modulator of fibrosis comprising: (i) providing a Gli1 expressing positive cell, contacting the Gli1 expressing positive cell with at least one candidate compound or agent; and (ii) measuring the level of expression of Gli1 in the cell in contact with the candidate compound or agent. A candidate compound or agent that can be screened according to the methods described herein include, but are not limited to, natural extracts of plants, animals or microorganisms, proteins, antibodies or small molecules. These compounds are screened either in a pure form or in mixtures with other compounds.

In one embodiment of the screening method, compound libraries can be screened.

Commercially available combinatorial small molecule drug libraries can be screened for such inhibitors using assay methods well known in the art and/or as described herein. For example, libraries from Vitas-M Lab and Biomol International, Inc. A comprehensive list of compound libraries can be found at Broad Institute at Harvard University. Other chemical compound libraries such as those from of 10,000 compounds and 86,000 compounds from NIH Roadmap, Molecular Libraries Screening Centers Network (MLSCN) can be screened successfully with the developed HTS assay.

In one embodiment, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. Methods for high-throughput screening are well known to one skilled in the art or are described, for example, in U.S. Pat. Nos. 5,976,813, 6,472,144, 6,692,856, 6,824,982, and 7,091,048, the disclosure of which are hereby incorporated by reference in their entirety.

The compound or group of compounds being selected by the method according to the invention are then used in the development of drugs to be used in the treatment of pathogenic fibrosis and chronic fibrosis.

Treatment of Kidney Fibrosis with Gli2 Inhibitors

The rising incidence of diabetes and hypertension in the aging population have led to increased rates of both chronic kidney disease (CKD) and end-stage renal disease (ESRD) (1-3) Estimates of CKD prevalence approach 10% in the United States, with more than 600,000 patients living with ESRD(3). These patients suffer substantial morbidity and mortality while on dialysis, and kidney transplant list wait times number in years because there are not enough kidneys available. The cost to care for patients with ESRD also consumes a disproportionate fraction of healthcare budgets (3, 4). For these reasons, novel therapeutic strategies to slow down CKD progression and reduce the incidence of ESRD incidence are urgently needed.

Kidney fibrosis is the common final pathway for nearly all progressive kidney diseases. Inhibiting kidney fibrosis therefore represents a logical strategy to slow down the progression of CKD to ESRD. However, there are currently no approved drugs available to treat kidney fibrosis (5). Myofibroblasts are widely accepted as the cell type responsible for the secretion of matrix proteins that drive kidney fibrosis (5, 6) and it has recently been shown that Gli1 expression identifies a perivascular mesenchymal stem cell (MSC)-like progenitor population that gives rise to myofibroblasts in solid organ injury (7). Genetic ablation of these cells ameliorates heart and kidney fibrosis, providing proof-of-principle that these cells represent a therapeutic target (7). The specificity of Gli1 expression in these myofibroblast progenitors prompted the inventors to investigate the functional role of hedgehog-Gli pathway in these cells during fibrosis as shown herein in the working Examples.

In vertebrates three members of the Gli transcription factor family exist—Gli1, Gli2 and Gli3, likely derived from duplications of a single ancestral Gli gene (8). All Gli proteins contain a C-terminal activator domain, whereas only Gli2 and Gli3 possess an N-terminal repressor domain (9). Data from mouse mutants indicate that Gli2 is important for the activator function in response to Hh signaling while Gli3 is the major repressor; Gli1 primarily amplifies the transcriptional response (9-13). The Hh receptor Patched (Ptc) is localized in and around the primary cilium. Upon binding of a Hh ligand (sonic, desert or indian Hh), Ptc releases tonic inhibition of the transmembrane protein smoothened (Smo) and leaves the cilium. Smo activation results in accumulation of suppressor of fused (SUFU)-Gli2 and SUFU-Gli3 complexes in the cilium, which otherwise would have been ubiquitinated and degraded (9, 10, 14). Following dissociation from SUFU, Gli2 (and Gli3) translocate into the nucleus where they activate the expression of Hh target genes, including Gli1 and Ptc1 (9, 10, 14).

In mammals, Gli1 is not required for Shh signaling and Gli1-knockout mice develop normally, unless one copy of Gli2 is defective (13, 15), whereas Gli2-knockout mice die at birth with severe skeletal and neural defects (16, 17). Studies in mutant mice where the zinc finger encoding exons have been removed from either Gli1 or Gli2 genes suggest that Gli2 can rescue most Gli1 functions whereas Gli1 cannot rescue Gli2 function (13). Interestingly, when Gli1 is expressed from the endogenous Gli2 locus it can rescue the in vivo function of Gli2 suggesting that only the activator form of Gli2 is required for development (18).

The Hh pathway regulates mesenchyme cell fates during kidney and ureteric development and growing evidence implicates a critical role of Hh in solid organ fibrosis and cancer (5, 6, 9, 19, 20). The inventors and others have reported a role of the Hh pathway in renal fibrosis (21-23). While some evidence suggests upregulation of Hh ligands during kidney fibrosis, accumulating data indicates that Gli proteins can also be activated in a ligand-independent fashion by transforming growth factor beta (TGF-β)(24, 25), platelet derived growth factor (PDGF) signaling (26, 27), epidermal growth factor receptor, RAS and AKT/PI3K pathways (28-33), all of which have also been reported to contribute to progression of fibrosis.

Given the specific expression Gli1 and Gli2 in myofibroblasts and their precursors (7, 21), the important role of Hh signaling in cell proliferation (27, 34, 35) and the possibility of direct activation of Gli proteins by known pro-fibrotic pathways, the inventors investigated the role of Gli1 and Gli2 in myofibroblast function in kidney fibrosis. The inventors demonstrate that conditional knockout of Gli2 or inhibition of Gli proteins by overexpression of the Gli3 repressor in Gli1 haploinsufficient mice, but not knockout of Gli1 alone, induces a specific myofibroblast cell-cycle arrest with reduced fibrosis. Furthermore, direct targeting of Gli proteins with darinaparsin, a novel organic arsenical with optimized pharmacokinetic properties that is currently undergoing clinical studies in hematologic malignancies and solid tumors (36, 37), inhibits hedgehog effectors Gli1 and Gli2 during kidney fibrosis and prevents myofibroblast proliferation. Darinaparsin acts by directly binding to Gli2 and inducing a Gli-dependent cell cycle arrest in kidney myofibroblasts. GANT61, a small molecule inhibitior of Gli, also ameliorates renal fibrosis in mice even when administered after injury. Furthermore, the inventors demonstrate that Gli1 and Gli2 expression is also increased in fibrotic human kidneys indicating that a similar mechanism is involved in humans kidney fibrosis progression.

Data provided herein in Example 3 indicates that Gli2 is upstream of Gli1 in the hedgehog signaling pathway of myofibroblast progenitors and/or mesenchymal stem cells. Thus, as described in more detail in Example 3, inhibition of Gli1 alone fails to prevent fibrosis. Without wishing to be bound by theory, the inventors have postulated that Gli2, being upstream of Gli1, can compensate for the loss of Gli1 function by signaling through the Hedgehog signaling pathway. The inventors have also shown that administration of an inhibitor of Gli2 (or Gli1/Gli2) can prevent fibrosis.

Accordingly, provided herein are methods for preventing and/or treating fibrosis, such as kidney fibrosis, by inhibiting Gli2. As used herein, the term "inhibiting Gli2" refers to the inhibition of activity of Gli2 in the Hedgehog signaling pathway, as determined by measuring activity or expression of a downstream target of Gli2, for example, patched Drosophila homolog (PTCH). In one embodiment, "inhibiting Gli2" as used herein refers to the inhibition of Gli2 at a minimum. In another embodiment, "inhibiting Gli2" can also refer to inhibition of Gli1/Gli2, Gli2/Gli3 or Gli1/Gli2/Gli3. As used herein, the term "specific inhibition of Gli2" refers to inhibition of Gli2 without concomitant inhibition of the activities of Gli1 and/or Gli3.

In one embodiment, the Gli2 inhibitor is darinaparsin. Darinaparsin is a small-molecule organic arsenical with potential antineoplastic activity. Although the exact mechanism of action is unclear, the inventors have shown herein that darinaparsin comprises activity as a Gli2 inhibitor. Darinaparsin may also generate volatile cytotoxic arsenic compounds when glutathione (GSH) concentrations are low. The arsenic compounds generated from darinaparsin disrupt mitochondrial bioenergetics, producing reactive oxygen species (ROS) and inducing ROS-mediated tumor cell apoptosis; in addition, this agent or its byproducts may initiate cell death by interrupting the G2/M phase of the cell cycle and may exhibit antiangiogenic effects. Compared to inorganic arsenic compounds such as arsenic trioxide (As2O3), darinaparsin appears to exhibit a wide therapeutic window.

In another embodiment, the Gli2 inhibitor is GANT61.

Pharmaceutically Acceptable Carriers

Therapeutic compositions of the agents disclosed herein contain a physiologically tolerable carrier together with a Gli2 inhibitor as described herein, dissolved or dispersed therein as an active ingredient. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without toxicity or the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein.

Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. Therapeutic compositions used herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

In some embodiments, it can be advantageous to formulate the aforementioned pharmaceutical compositions in dosage unit form for ease of administration and uniformity of dosage. Dosage unit or unitary form refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Dosage and Administration

In a treatment method as described herein, an effective amount of a Gli2 inhibitor is administered to a patient suffering from or diagnosed as having fibrosis (e.g., kidney fibrosis). In one aspect, the methods described herein provide a method for treating fibrosis in a subject. In one embodiment, the subject can be a mammal (e.g., a primate or a non-primate mammal). In another embodiment, the mammal can be a human, although the approach is effective with respect to all mammals. An "effective amount" means an amount or dose generally sufficient to bring about the desired therapeutic or prophylactic benefit in subjects undergoing treatment.

Effective amounts or doses of a Gli2 inhibitor for treatment as described herein can be ascertained by routine methods such as modeling, dose escalation studies or clinical trials, and by taking into consideration routine factors, e.g., the mode or route of administration of delivery, the pharmacokinetics of the composition, the severity and course of the disorder or condition, the subject's previous or ongoing therapy, the subject's health status and response to drugs, and the judgment of the treating physician. An exemplary dose for a human is in the range of from about 0.001 to about 8 mg per kg of subject's body weight per day, about 0.05 to 300 mg/day, or about 50 to 400 mg/day, in single or divided dosage units (e.g., BID, TID, QID).

While the dosage range for the composition comprising a Gli2 inhibitor depends upon the potency of the composition, and includes amounts large enough to produce the desired effect (e.g., inhibition of Hedgehog signaling in a cell), the dosage should not be so large as to cause unacceptable adverse side effects. Generally, the dosage will vary with the formulation (e.g., oral, i.v. or subcutaneous formulations), and with the age, condition, and sex of the patient. The dosage can be determined by one of skill in the art and can also be adjusted by the individual physician in the event of any complication. Typically, the dosage will range from 0.001 mg/day to 400 mg/day. In some embodiments, the dosage range is from 0.001 mg/day to 400 mg/day, from 0.001 mg/day to 300 mg/day, from 0.001 mg/day to 200 mg/day, from 0.001 mg/day to 100 mg/day, from 0.001 mg/day to 50 mg/day, from 0.001 mg/day to 25 mg/day, from 0.001 mg/day to 10 mg/day, from 0.001 mg/day to 5 mg/day, from 0.001 mg/day to 1 mg/day, from 0.001 mg/day to 0.1 mg/day, from 0.001 mg/day to 0.005 mg/day. Alternatively, the dose range will be titrated to maintain serum levels between 0.1 µg/mL and 30 µg/mL.

Administration of the doses recited above can be repeated for a limited period of time or as necessary. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

Agents useful in the methods and compositions described herein depend on the site of fibrosis and can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. For the treatment of certain fibrotic diseases, the agent can be administered systemically.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

Efficacy Measurement

The efficacy of a treatment comprising a Gli2 inhibitor for fibrosis (e.g., kidney fibrosis) can be determined by the skilled clinician. However, a treatment is considered "effective treatment," as the term is used herein, if any one or all of the signs or symptoms of, as but one example, kidney fibrosis are altered in a beneficial manner, other clinically accepted symptoms or markers of disease are improved or ameliorated, e.g., by at least 10% following treatment with an inhibitor. Efficacy can also be measured by failure of an individual to worsen as assessed by hospitalization or need for medical interventions (e.g., progression of the disease is halted or at least slowed). Efficacy in a population of patients can also be determined by measuring mortality rates due to advance fibrotic disease. Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of fibrotic disease; or (2) relieving the disease, e.g., causing regression of symptoms; and (3) preventing or reducing the likelihood of the development of fibrosis, including renal fibrosis.

Biomarkers for assessing efficacy of Gli2 inhibition in e.g., kidney fibrosis include blood urea nitrogen (BUN), creatinine clearance, Cystatin-C, circulating uric acid, urine angiotensinogen, urinary albumin, urinary TGF-β1, urinary connective tissue growth factor, urinary plasminogen activator inhibitor (PAI-1), and urinary collagen IV, among others. Such markers can be measured before and after treatment, e.g., where a decrease in urinary excretion of biomarkers of kidney damage are indicative of a response to treatment.

Various methods are provided herein for determining a subject's response to treatment with a a Gli2 inhibitor. In one embodiment, the subject's response is determined by measuring levels of a biomarker in urine. In another embodiment, the subject's response is determined by measuring levels of a biomarker in blood, or a fraction thereof, for example, whole blood; plasma (e.g., separated by centrifugation); serum from plasma (e.g., obtained by clotting or serum separator tubes); or total cells or isolated subsets (e.g., fibroblasts etc.).

References or Reference Samples

The terms "reference level," "reference sample," and "reference" are used interchangeably herein and refer to the level of expression of a biomarker in a known sample against which another sample is compared (i.e., obtained from a subject having or suspected of having fibrosis). A standard is useful for determining the amount of the biomarker or the relative increase/decrease of the biomarker in a biological sample. A standard serves as a reference level for comparison, such that samples can be normalized to an appropriate standard in order to infer the presence, absence or extent of fibrosis in a subject or in an organ.

In one embodiment, a biological standard is obtained at an earlier time point (presumably prior to the onset of detectable fibrosis) from the same individual that is to be tested or treated as described herein. Alternatively, a standard can be from the same individual having been taken at a time after the onset or diagnosis of fibrosis. In such instances, the standard can provide a measure of the efficacy of treatment.

A standard level can be obtained, for example, from a known biological sample from a different individual (e.g., not the individual being tested) that is substantially free of fibrosis. A known sample can also be obtained by pooling samples from a plurality of individuals to produce a standard over an averaged population, wherein a standard represents an average level of the biomarker among a population of individuals (e.g., a population of individuals having fibrosis). Thus, the level of the biomarker in a standard obtained in this manner is representative of an average level of this marker in a general population of individuals having fibrosis, or a population of individuals having fibrosis. An individual sample is compared to this population standard by comparing expression of the biomarker from a sample relative to the population standard. Generally, an increase in the amount of the biomarker over the standard (e.g., a reference obtained from subjects lacking fibrosis) will indicate the presence of fibrosis, while a decrease in the amount of the biomarker will indicate that the individual does not have fibrosis. The converse is contemplated in cases where a standard is obtained from a population of subjects having fibrosis. It should be noted that there is often variability among individuals in a population, such that some individuals will have higher levels of biomarker expression, while other individuals have lower levels of expression. However, one skilled in the art can make logical inferences on an individual basis regarding the detection and treatment of fibrosis as described herein.

A standard or series of standards can also be synthesized. A known amount of the biomarker (or a series of known amounts) can be prepared within the typical expression range for the biomarker that is observed in a general fibrotic population. This method has an advantage of being able to compare the extent of disease in one or more individuals in a mixed population. This method can also be useful for subjects who lack a prior sample to act as a standard or for routine follow-up post-diagnosis. This type of method can also allow standardized tests to be performed among several clinics, institutions, or countries etc.

The present invention may be as defined in any one of the following numbered paragraphs.

[1] A method of isolating, detecting or identifying nascent mesenchymal stem cells (MSCs) in an adult tissue, the method comprising contacting a tissue or a population of cells derived from a tissue with an agent that specifically binds to Gli1.

[2] A method of isolating nascent mesenchymal stem cells (MSCs) in an adult tissue comprising isolating Gli1 expressing positive cells.

[3] The method of paragraph 1 or 2, wherein the adult tissue is in an organ.

[4] The method of paragraph 1, 2 or 3, wherein the organ is a solid organ

[5] The method of paragraph 4, wherein the solid organ is selected from heart, liver, lung, kidney, skin and bone marrow.

[6] The method of any one of paragraphs 1, or 3-5, wherein the agent is an anti-Gli1 antibody.

[7] The method of any one of paragraphs 1-6, wherein the method comprises an immune assay.

[8] A method of detecting myofibroblasts in an adult tissue, the method comprising contacting a tissue or a population of cells derived from the adult tissue with a first agent that specifically binds to Gli1 and a second agent that specifically binds to alpha-smooth muscle actin.

[9] A method of detecting myofibroblasts in an adult tissue comprising detecting Gli1positive and alpha-smooth muscle actin positive expressing cells.

[10] A method of detecting or monitoring for the induction of tissue fibrosis in an organ, the method comprising:
  a) providing a sample of tissue from an organ,
  b) detecting myofibroblasts or Gli1positive and alpha-smooth muscle actin positive expressing cells in the organ; and
  c) identifying a presence of fibrosis in the organ when there is a detectable amount of myofibroblasts compared to a reference.

[11] The method of paragraph 10, wherein the detecting comprises contacting a tissue or a population of cells derived from a tissue with an agent that specifically binds to Gli1.

[12] The method of paragraph 10 or 11, wherein the detecting comprises an immune assay.

[13] The method of paragraph 10, 11, or 12, further comprising selecting a subject suspected of having tissue fibrosis.

[14] The method of any one of paragraphs 10-13, further comprising identifying a presence of fibrosis in the organ when there is an increase in Gli1positive and alpha-smooth muscle actin positive expressing cells over the reference or identifying an absence of fibrosis in the organ when there is a decrease or no difference in Gli1positive and alpha-smooth muscle actin positive expressing cells compared to the reference.

[15] The method of any one of paragraphs 10-14, further comprising treating or inhibiting the fibrosis by administering at least an anti-fibrosis treatment when the presence of fibrosis in the organ is identified.

[16] A method of detecting or monitoring for the induction of tissue fibrosis in an organ, the method comprising
  a) providing a sample of tissue from an organ;
  b) contacting the tissue or a population of cells derived from the tissue with an agent that specifically binds to Gli1;
  c) measuring a level of Gli1 expression in the tissue or a population of cells derived from the tissue;
  d) comparing the measured level of Gli1 expression with a reference; and
  e) identifying a presence of fibrosis in the organ when there is an increase in Gli1 expression over the reference or identifying an absence of fibrosis in the organ when there is a decrease or no difference in Gli1 expression compared to the reference.

[17] A method of monitoring the progression of tissue fibrosis in an organ from an individual, the method comprising:
  a) providing a first sample of tissue at a first time point from the organ that is having tissue fibrosis;
  b) determining the level of Gli1 expression in the first sample;
  c) providing a second sample of tissue at a second time point from the same organ that is having tissue fibrosis, the first time point being before the second time point;
  d) determining the level of Gli1 expression in a second sample;
  e) comparing the levels of Gli1 from the time points with a reference Gli1 level; and
  f) assessing that tissue fibrosis in an organ is regressing where the levels of Gli1 at the second time point is lower than the reference Gli1 level, or assessing that tissue fibrosis in an organ is progressing where the levels of Gli1 at the second time point is higher than the reference Gli1 level.

[18] The method of paragraph 16 or 17 further comprising measuring the level of alpha-smooth muscle actin in the same tissue or a population of cells derived from the tissue and comparing with the measured level of alpha-smooth muscle actin with a reference.

[19] The method of paragraph 16, 17 or 18, further comprising selecting an individual suspected of developing or at risk of developing fibrosis.

[20] The method of any one of paragraphs 16-19 further comprising treating or inhibiting the fibrosis by administering at least an anti-fibrosis treatment when the presence of fibrosis in the organ is identified.

[21] The method of any one of paragraphs 16-20 further comprising measuring the level of alpha-smooth muscle actin in the same first and second samples and comparing with the measured level of alpha-smooth muscle actin with a reference.

[22] The method of any one of paragraphs 16-21 further comprising selecting an individual who has been determined to have fibrosis.

[23] The method of any one of paragraphs 16-22 further comprising continuing treatment of or inhibition of the fibrosis by administering at least an anti-fibrosis treatment when the presence of fibrosis in the organ is identified.

[24] A method of screening for inhibitors of fibrosis comprising
  a) providing a Gli1 expressing positive cell
  b) contacting the Gli1 expressing positive cell with at least one candidate compound or agent; and
  c) measuring the level of expression of Gli1 in the cell in contact with candidate compound or agent.

[25] The method of paragraph 24 further comparing the measured level of Gli1 expression with a reference wherein the measured level of Gli1 expression is reduced compared to the reference indicate that the candidate compound or agent is a likely inhibitor of tissue fibrosis.

[26] A method of treating or preventing fibrosis, the method comprising ablating Gli1+ cells in a tissue at risk of or undergoing fibrosis.

[27] A method of treating or preventing fibrosis, the method comprising: administering to a subject having or suspected of having fibrosis with an inhibitor of Gli2 activity.

[28] The method of paragraph 27, wherein the inhibitor of Gli2 activity also inhibits Gli1 and/or Gli3 activity.

[29] The method of paragraph 27 or 28, further comprising a step of diagnosing a subject as having fibrosis.

[30] The method of paragraph 27, 28, or 29, wherein the step of diagnosing is performed by detecting the presence of Gli1+ cells in a biological sample obtained from the subject.

[31] The method of any one of paragraphs 27-30, wherein detecting the presence of Gli1+ cells comprises contacting a biological sample obtained from the subject with an agent that specifically binds Gli1.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: Exemplary Experiments Designed for Identification of a Subset of Renal Stroma Defined by Gli1 Expression and Mesenchymal Stem Cell Characteristics The inventors have identified a novel stromal cell population in kidney defined by expression of Gli1, a transcription factor in the hedgehog pathway. These Gli1+ cells constitute only a fraction of the total PDGFRβ+ stromal population, and they are located directly adjacent to endothelial cells of the renal microvasculature and in the adventitia of arteries. In Gli1-CreERt2; R26tdTomato mice given tamoxifen, Gli1+ cells are adjacent to endothelial cells and in the perivascular position around arterioles (data not shown). These are PDGFRβ+, but only represent ~25% of the total PDGFRb+ pool (data not shown). The inventors have generated a genetic model to label these cells (Gli1-CreERt2; R26tdTomato), and analyzed their surface staining characteristics by FACS. These cells express a typical MSC signature: CD44+, CD29+, Sca1+, CD105+, CD45−, CD34− and CD31−[25].

Because these Gli1+ cells represent only a fraction of the total kidney stromal pool, it was sought to determine whether these cells might serve as a myofibroblast progenitor pool. The inventors showed by genetic lineage analysis that these Gli1+ resident stromal cells expand by 20-fold during unilateral ureteral obstruction-induced renal fibrosis (UUO), whereupon they acquire αSMA expression during myofibroblastic differentiation. There is dramatic expansion of labeled cells by day 10 after UUO, as shown by the low power (4×) fluorescence image before and after UUO (data not shown). Quantitation by FACS revealed a 19.7+/−3 fold increase in Gli1+ cell number after UUO (n=3, p=0.0005, t-test). Immunostaining for αSMA reveals colocalization between Gli1+ cells and aSMA after UUO, indicating myofibroblast identity of Gli1+ progenitors after UUO (data not shown). These findings indicate that Gli1+ kidney cells are the key myofibroblast progenitor pool, representing a distinct stromal subtype within the PDGFRβ+ stromal population.

The evidence that Gli1+ resident kidney cells are MSC consists of the FACS signature, which is characteristic of MSCs, and the fact that bone marrow Gli1+ cells show trilineage differentiation capacity. In fact, data exists to indicate that all MSCs are in fact pericytes, despite the fact that this has not been shown in kidney [26]. The inventors propose that Gli1+ resident stromal cells are a MSC population that contributes to interstitial homeostasis during aging but differentiates into myofibroblasts after injury. These resident kidney MSC are multipotent progenitors that contribute to interstitial homeostasis in health, but lose their multipotentiality in aging or after injury where they differentiate into myofibroblasts. The studies described herein validate the kidney resident MSC as a therapeutic target in aging and CKD.

Genetic Ablation of Gli1+ MSC

Figure 3C:
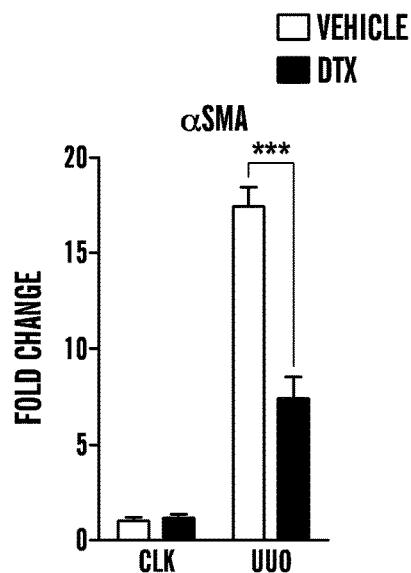
Figure 3D:
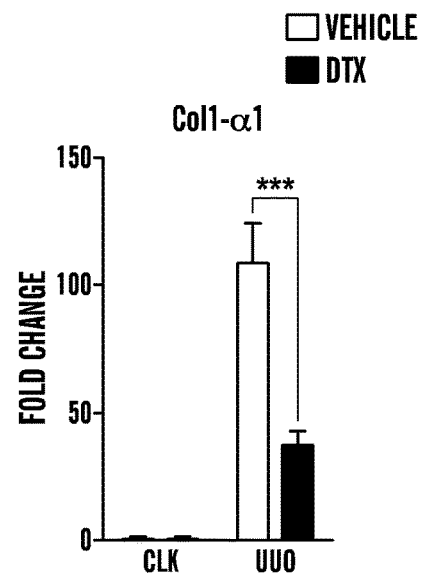
Figure 3E:
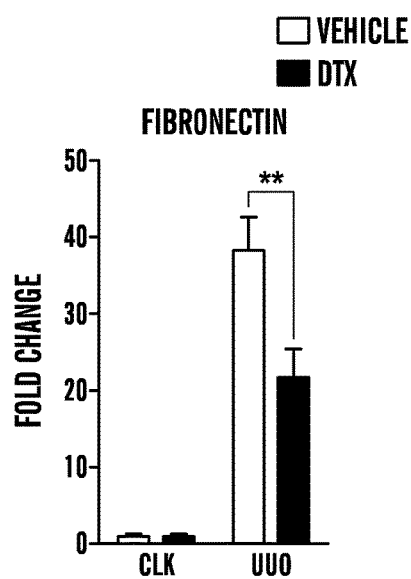
Figure 3F:
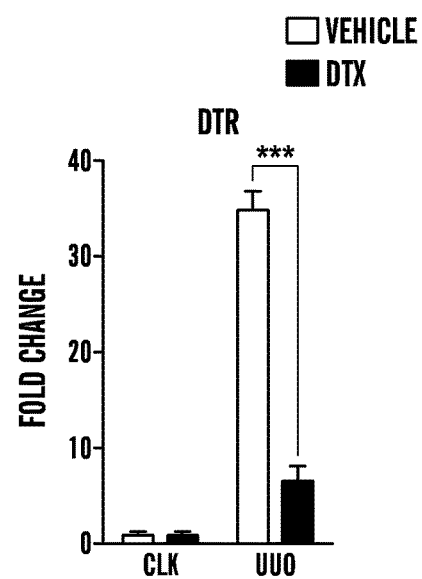
Figure 4:
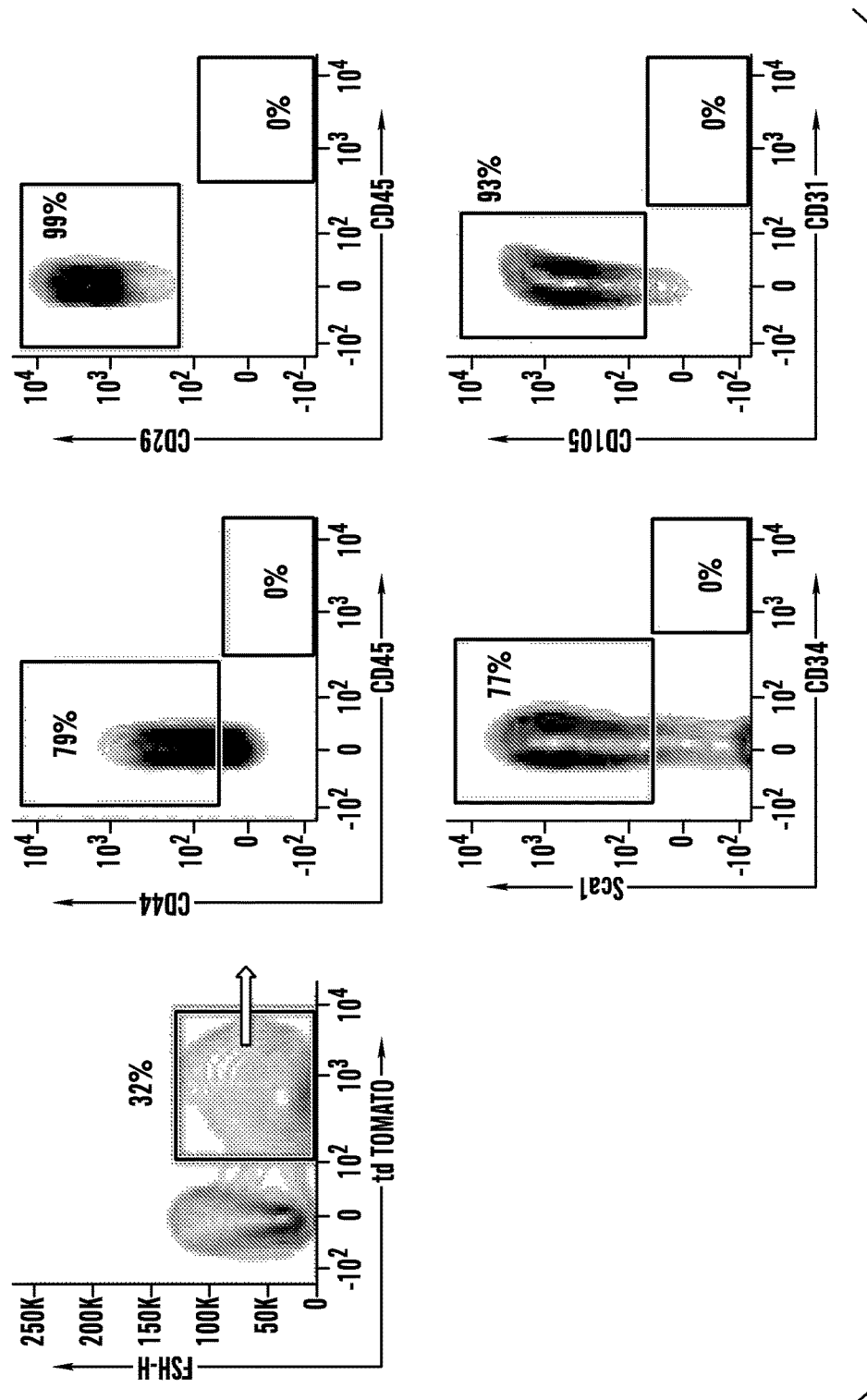
FIG. 4 shows data indicating that bone marrow also contains Gli1+ MSC. These MSC express the same surface markers as Gli1+ MSC isolated from kidney (CD44+, CD29+, Sca1+, CD105+ and CD31−, CD34−, CD45−). Data from immunofluorescence staining showed CD31+ endothelial cells of bone marrow sinusoids surrounded by Gli1-tdTomato MSC, in the typical pattern (data not shown). Bone chip from Gli1-CreERt2; R26tdTomato mouse allows ready culture of labeled Gli1+ MSC. Gli1+ MSC from bone marrow are multipotent and show trilineage differentiation capacity (data not shown).

The inventors have used Gli1-CreERt2;R26iDTR bigenic mice to genetically ablate Gli1+ cells during UUO. The R26iDTR mouse expresses the human diphtheria toxin receptor (DTR) after CreERt2-induced recombination of a floxed stop sequence [35]. Because human diphtheria toxin (DTX) does not bind to mouse DTR, administration of human DTX in this setting will ablate any Gli1+ cell because it expresses the human DTR. This genetic model (outlined in FIGS. 4A, 4B) was used to ablate Gli1+ cells during UUO. A >50% reduction in αSMA, Col1α1 and fibronectin expression (FIGS. 4C-4E) was observed as a result. A dramatic reduction in αSMA+ cells was also observed in kidneys from mice treated with DTX subjected to UUO (FIG. 3G). This experiment indicates that Gli1+ cells play a central role in renal fibrogenesis.

Bone Marrow MSC Express Gli1

A defining characteristic for bone marrow-derived MSC to date has been the absence of a single marker that distinguishes them from other cell types. Rather, MSC are defined functionally (adherence to plastic, trilineage differentiation capacity), and by a panel of markers [25, 39]. The inventors have discovered that Gli1+ sensitively and specifically marks bone marrow-derived MSC. These cells are located just adjacent to endothelium within bone marrow (data not shown), the expected location for bone marrow MSC [40, 41]. They readily adhere to plastic and can be cultured in quantity from bone chips by a published protocol for MSC isolation [42] (FIG. 4A). Critically, they express the same panel of markers that define them as MSC as the Gli+ cells isolated from kidney (FIG. 4B). Finally, they possess trilineage differentiation capacity (FIG. 4C). These results have two implications. First, the fact that bone marrow-derived Gli1+ cells show trilineage differentiation capacity indicates that Gli1+ cells within kidney are multipotent as well. Second, these Gli1+ cells are very likely to be the population of circulating myofibroblast progenitors identified recently [24].

Defining Bone Marrow Contribution of Gli1+ MSC to the Kidney Myofibroblast Pool During Fibrosis In parabiosis, two animals share one circulation. To define the bone marrow contribution of li1+ MSC, the inventors will genetically label Gli1+ cells using their standard approach, and then conjoin that animal to an animal which has no labeled cells. In order to allow rapid verification of a complete cross-circulation by flow cytometry Gli1-CreERt2,tdTomato mice which carry the regular CD45.2 isoform of the leukocyte common antigen will be conjoined with mice that carry the CD45.1 isoform (B6.SJL-Ptprca Pepcb/Boy, #2014 Jackson). The mice will be verified at 4 weeks after parabiosis, and then perform UUO surgery on the mouse that does not have labeled cells. The parabiotic pair are sacrificed at day 5 or day 10 (n=5 parabionts per time point). Confocal microscopy and flow-cytometry will be used to determine whether red-labeled cells from the Gli1,tdtomato+ parabiont home to the injured kidney of the other parabiont. As a second experiment full bone marrow transplantation (BMTX) of Gli1− tdtomato+ male donors in wildtype littermates is performed. Because it is controversial whether MSC engraft following BMTX [27, 28, 43] the inventors will first study their engraftment capability at 4 weeks after BMTX via confocal microscopy and flow cytometry. Chimerism is verified using FISH. When engrafted td-tomato+ MSC are found, a second cohort of mice will be subjected to UUO or sham surgery 4 weeks following the BMTX (n=5 each) to study whether the engrafted bone marrow MSC are able to home to the kidney following injury.

Ablation of Gli1+ Cells in Parabiotic Pairs

To a) elucidate whether bone marrow MSC are progenitors of resident kidney MSC/pericytes and b) determine in which extent circulating versus resident MSC contribute to kidney fibrosis the inventors will perform parabiosis with Gli1-CreERt2; tdtomato males conjoined to Gli1-CreERt2; iDTR females. Three weeks after the parabiosis DTX is injected in order to ablate resident Gli1+ MSC in the parabiont that harbors the simian diphteriatoxin receptor. Mice are sacrificed at different time-points following cell ablation in order to study homing of circulating MSC to the kidney via flow-cytometry and confocal microscopy. Cross-circulation is verified via FISH of spleen lymphocytes following sacrification. In a second set of experiments the inventors will perform UUO surgery in either the iDTR or the Gli1-tdtomato parabiont (n=5 each) four weeks after parabiosis surgery followed by cell-ablation via DTX injection (vs vehicle injection). Readouts of this experiment will be a) cell homing of tdtomato+MSC following cell-ablation and UUO using flow cytometry and confocal microscopy and b) standard fibrotic readouts to elucidate the severity of fibrosis. This experiment will define the capability of circulating MSC to replace resident MSC during kidney homeostasis and injury and determine the extent of circulating MSC.

Without wishing to be bound by theory, the inventors expect that MSC from the bone-marrow home to the kidney and transdifferentiate to myofibroblasts after injury, however it is expected that the majority of myofibroblasts arise from resident kidney MSC via proliferation. It is also expected that bone-marrow MSC are able to replace resident tissue MSC after ablation. Because it is controversial whether MSC engraft following bone-marrow transplantation and most MSC are stuck in lung capillaries following intravenous injection [44] the inventors will alternatively perform direct intra-femoral injection of whole bone marrow to improve the engraftment of Gli1+ MSC [45]. In the parabiosis cell-ablation experiments the inventors expect reduced severity of kidney-fibrosis following ablation of MSC in the bone marrow of the non-UUO parabiont because bone marrow MSC from both parabionts home equally to the injured kidney.

Figure 5:
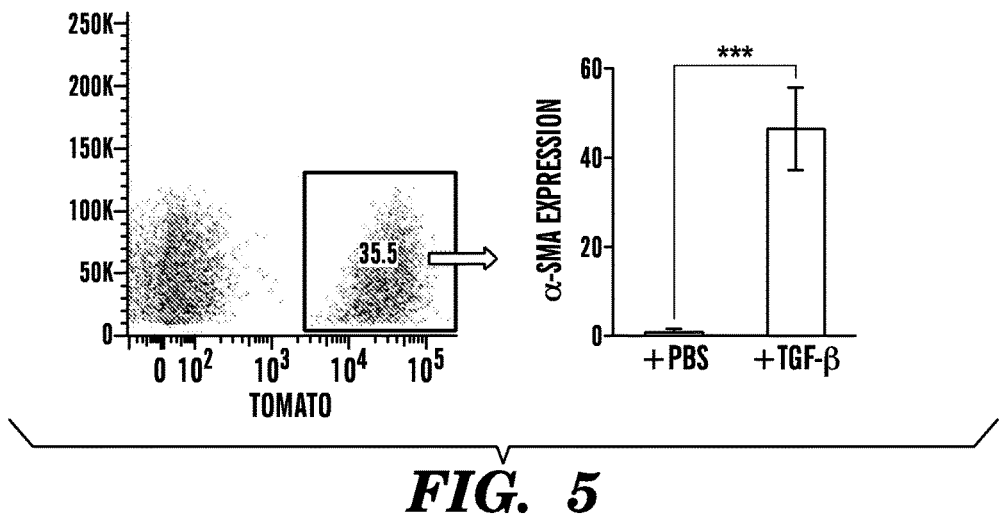
FIG. 5 shows myofibroblast differentiation of Gli1+ MSC in vitro. Bone marrow-derived Gli1+ MSC were isolated and purified to homogeneity by FACS. This pure culture was incubated with TGFb, resulting in 45× induction of αSMA, the myofibroblast marker. This serves as one model to use Gli1positive cells to screen for inhibitors of myofibroblast differentiation.

Role of Aging and TGFβ in Loss of Gli1+ MSC Multipotentiality and Vasculotropic Properties In order to test whether Gli1+ MSC undergo myofibroblast differentiation in response to TGFl3, these cells were isolated from bone marrow and purified by FACS. A pure population of Gli1-tdTomato+ cells were then incubated in the presence or absence of TGFl3. As shown in FIG. 5, there was robust upregulation of αSMA in response to TGFβ. These results were expected, since this is what was observed in vivo. However it also establishes a method for in vitro differentiation of these cells for further characterization. For example, the inventors have hypothesized that healthy Gli1+ MSC are pro-angiogenic and help maintain microvasculature through paracrine actions, consistent with known roles for pericytes (of which MSC are a subset). The inventors have developed a coculture assay in order to measure the angiogenic functions of Gli1+ MSC.

Figure 6:
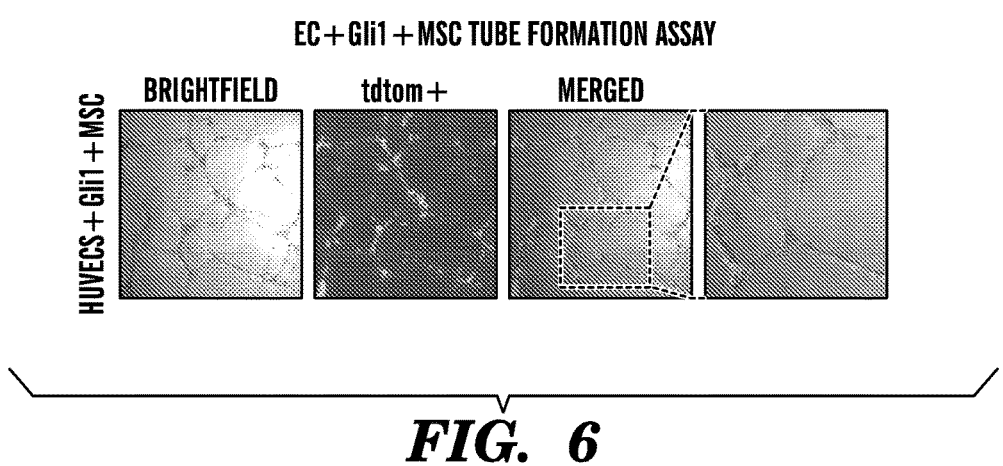
FIG. 6. Tube formation assay. When human umbilical vein endothelial cells (HUVEC) are cocultured with labeled Gli1+ MSC, tube formation rapidly ensues characterized by very close association between the MSC and HUVECs. This provides another model for screening Gli1positive cells for vascular stabilization.
Figure 7:
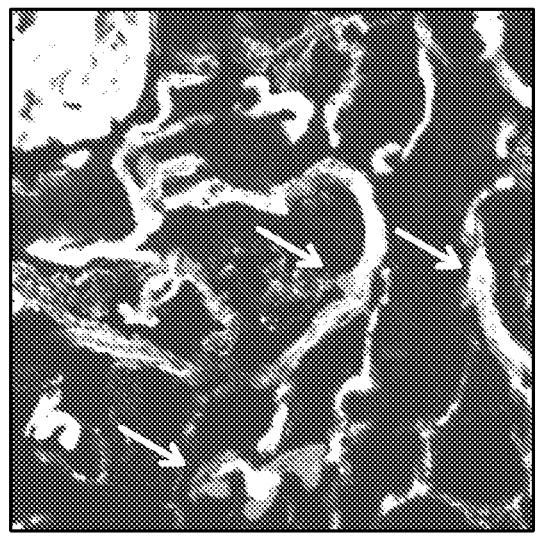
FIG. 7. Fluorescence microangiography reveals perivascular position of MSC in a Gli1-CreERt2; R26tdTomato mouse. The FITC signal fills the lumen of patent peritubular vessels (note glomerulus in upper left). Arrows indicate genetically labeled Gli1+ MSC. Not that they all occupy a position directly adjacent to/surrounding the capillary basement membrane.

This involves coculture of endothelial cells with labeled Gli1+ MSC in 3D gels (matrigel or collagen gel). What was observed is the very rapid formation of stabilized tubes, characterized by the close association of labeled Gli1+ MSC with the endothelium (FIG. 6). All MSC are closely associated with endothelial tubes. Using this assay, then, one can now assess the difference in tube formation in the presence or absence of Gli1+MSC, as well as to query the effect of aged MSC, or MSC exposed to TGFβ.

Tube Formation Assay

To determine the role of Gli1+ MSC/Pericytes on capillary rarefaction, which is one hallmark of chronic kidney disease progression, and uncover key factors driving this process the inventors will perform a three-dimensional tube formation assay with Gli1+ MSC (FACS sorted from kidney or bone marrow) and HUVECs. First, experiments with three-dimensional culture of HUVECs and MSC alone and together in matrigel and within a collagen I matrix with addition of TGFβ (10 ng/ml) or inhibition of TGFβ signaling using the TGFβI receptor kinase inhibitor LY2157299 will be performed. After incubation for 12 h (matrigel) and 120 hours (collagen gel) the gels will be fixed and the tube structures stained using calcein. Tube structures will be studies using fluorescence microscopy. After calcein staining living HUVECs will appear green and living pericytes/MSC will be yellow. Readouts will be number tubes/high power field (hpf/400x), number of loops/hpf, recruitment of pericytes to tubes (% of pericyte/tube association), average tube width, number of pericytes and HUVECs. Costaining for α-SMA will be performed using a Cy5 secondary antibody in order to determine the number of MSC that transdifferentiate into myofibroblasts. This experiment will be repeated under hypoxic conditions ($CO_2$ 10%, $O_2$ 3%,) using a tri-gas incubator with nitrogen. In a second set of experiments FACSorted Gli1+ MSC from fibrotic kidneys (day 10 UUO), from old mice (18 months) and from a late passage (P 8-9) will be used as it is expected that the Gli1+ myofibroblasts lose their capability to be recruited to EC tubes in vitro. The basement membrane matrix deposition will be determined via immunostaining for laminin and collagen IV as the inventors expect that TGFβ treatment as well as MSC from old mice or fibrotic kidneys have a reduced capability to produce basement membrane matrix leading to instability of EC tubes.

It is expected that age will reduce colony forming efficiency as well as trilineage potential in Gli1+ MSC, that old MSC will spontaneously differentiate into myofibroblasts upon transplantation whereas young MSC will maintain their undifferentiated state.

The inventors expect that TGFβ treatment will induce a myofibroblastic phenotype of MSC with a reduced recruitment of MSC to EC tubes. In addition, the inventors also expect that MSC from old mice or fibrotic kidneys will lose the capability to be recruited and to stabilize EC tubes by producing basement membrane matrix. It is expected that hypoxia leads to increased proliferation of MSC with reduced recruitment to tubes and reduced basement membrane matrix. The inventors may additionally assess endothelial cell apoptosis in this model, since they hypothesize that MSC will exert pro-survival effects on these cells. This may be measured by TUNEL assay.

REFERENCES FOR EXAMPLE 1

1. Anderson, S., et al., *Prediction, progression, and outcomes of chronic kidney disease in older adults*. J Am Soc Nephrol, 2009. 20(6): p. 1199-209.
2. *USRDS* 2010 *Annual Data Report: Atlas of Chronic Kidney Disease in the United States.* 2010, National Institutes of Health, National Institute of Diabetes and Digestive and Kidney Diseases, Bethesda, Md.
3. Armulik, A., A. Abramsson, and C. Betsholtz, *Endothelial/pericyte interactions*. Circ Res, 2005. 97(6): p. 512-23.
4. Lemley, K. V. and W. Kriz, *Anatomy of the renal interstitium*. Kidney Int, 1991. 39(3): p. 370-81.
5. Nath, K. A., *Tubulointerstitial changes as a major determinant in the progression of renal damage*. Am J Kidney Dis, 1992. 20(1): p. 1-17.
6. Striker, G. E., et al., *Structural-functional correlations in renal disease. I. A method for assaying and classifting histopathologic changes in renal disease*. Hum Pathol, 1970. 1(4): p. 615-30.
7. Risdon, R. A., J. C. Sloper, and H. E. De Wardener, *Relationship between renal function and histological changes found in renal-biopsy specimens from patients with persistent glomerular nephritis*. Lancet, 1968. 2(7564): p. 363-6.
8. Otranto, M., et al., *The role of the myofibroblast in tumor stroma remodeling*. Cell Adh Migr, 2012. 6(3): p. 203-19.
9. Eyden, B., *The myofibroblast: a study of normal, reactive and neoplastic tissues, with an emphasis on ultrastructure. part 2-tumours and tumour-like lesions*. J Submicrosc Cytol Pathol, 2005. 37(3-4): p. 231-96.
10. Hinz, B., *The myofibroblast: paradigm for a mechanically active cell*. J Biomech, 2010. 43(1): p. 146-55.
11. Follonier Castella, L., et al., *Regulation of myofibroblast activities: calcium pulls some strings behind the scene*. Exp Cell Res, 2010. 316(15): p. 2390-401.
12. Lin, S. L., et al., *Pericytes and perivascular fibroblasts are the primary source of collagen-producing cells in obstructive fibrosis of the kidney*. Am J Pathol, 2008. 173(6): p. 1617-27.
13. Ishii, Y., et al., *Injury and progressive loss of peritubular capillaries in the development of chronic allograft nephropathy*. Kidney Int, 2005. 67(1): p. 321-32.

14. Matsumoto, M., et al., *Hypoperfusion of peritubular capillaries induces chronic hypoxia before progression of tubulointerstitial injury in a progressive model of rat glomerulonephritis.* J Am Soc Nephrol, 2004. 15(6): p. 1574-81.
15. Kang, D. H., et al., *Role of the microvascular endothelium in progressive renal disease.* J Am Soc Nephrol, 2002. 13(3): p. 806-16.
16. Nangaku, M., *Chronic hypoxia and tubulointerstitial injury: a final common pathway to end-stage renal failure.* J Am Soc Nephrol, 2006. 17(1): p. 17-25.
17. Basile, D. P., et al., *Renal ischemic injury results in permanent damage to peritubular capillaries and influences long-term function.* Am J Physiol Renal Physiol, 2001. 281(5): p. F887-99.
18. Basile, D. P., *Rarefaction of peritubular capillaries following ischemic acute renal failure: a potential factor predisposing to progressive nephropathy.* Curr Opin Nephroi Hypertens, 2004. 13(1): p. 1-7.
19. Nakaya, Y. and G. Sheng, *EMT in developmental morphogenesis.* Cancer Lett, 2013.
20. Kalluri, R. and R. A. Weinberg, *The basics of epithelial-mesenchymal transition.* J Clin Invest, 2009. 119(6): p. 1420-8.
21. Chu, A. S., et al., *Lineage tracing demonstrates no evidence of cholangiocyte epithelial-to-mesenchymal transition in murine models of hepatic fibrosis.* Hepatology, 2011. 53(5): p. 1685-95.
22. Humphreys, B. D., et al., *Fate tracing reveals the pericyte and not epithelial origin of myofibroblasts in kidney fibrosis.* Am J Pathol, 2010. 176(1): p. 85-97.
23. Rock, J. R., et al., *Multiple stromal populations contribute to pulmonary fibrosis without evidence for epithelial to mesenchymal transition.* Proc Natl Acad Sci USA, 2011. 108(52): p. E1475-83.
24. Lebleu, V. S., et al., *Origin and function of myofibroblasts in kidney fibrosis.* Nat Med, 2013. 19(8): p. 1047-1053.
25. Dominici, M., et al., *Minimal criteria for defining multipotent mesenchymal stromal cells. The International Society for Cellular Therapy position statement.* Cytotherapy, 2006. 8(4): p. 315-7.
26. Crisan, M., et al., *A perivascular origin for mesenchymal stem cells in multiple human organs.* Cell Stem Cell, 2008. 3(3): p. 301-13.
27. Miura, Y., et al., *Chimerism of bone marrow mesenchymal stem/stromal cells in allogeneic hematopoietic cell transplantation: is it clinically relevant?* Chimerism, 2013. 4(3): p. 78-83.
28. Cilloni, D., et al., *Limited engraftment capacity of bone marrow-derived mesenchymal cells following T-cell-depleted hematopoietic stem cell transplantation.* Blood, 2000. 96(10): p. 3637-43.
29. Humphreys, B. D. and D. P. Dirocco, *Lineage-tracing methods and the kidney.* Kidney Int, 2013.
30. Dirocco, D. P., et al., *Wnt4/beta-Catenin Signaling in Medullary Kidney Myofibroblasts.* J Am Soc Nephroi, 2013. 24(9): p. 1399-412.
31. Kusaba, T., et al., *Differentiated kidney epithelial cells repair injured proximal tubule.* Proc Natl Acad Sci USA, 2013. in press.
32. Grgic, I., et al., *Targeted proximal tubule injury triggers interstitial fibrosis and glomerulosclerosis.* Kidney Int, 2012. 82(2): p. 172-83.
33. Kelley, R., et al., *A population of selected renal cells augments renal function and extends survival in the ZSF1 model of progressive diabetic nephropathy.* Cell Transplant, 2013. 22(6): p. 1023-39.
34. Kramann, R., M. Tanaka, and B. D. Humphreys, *Fluorescence Microangiography for Quantitative Assessment of Peritubular Capillary Changes after Acute Kidney Injury in Mouse.* Journal of the American Society of Nephrology, 2014. In Press.
35. Buch, T., et al., *A Cre-inducible diphtheria toxin receptor mediates cell lineage ablation after toxin administration.* Nat Methods, 2005. 2(6): p. 419-26.
36. Fabian, S. L., et al., *Hedgehog-Gli pathway activation during kidney fibrosis.* Am J Pathol, 2012. 180(4): p. 1441-53.
37. Asada, N., et al., *Dysfunction of fibroblasts of extrarenal origin underlies renal fibrosis and renal anemia in mice.* J Clin Invest, 2011. 121(10): p. 3981-90.
38. Dirocco, D., et al., *CDK4/6 Inhibition Induces Epithelial Cell Cycle Arrest and Ameliorates Acute Kidney Injury.* Am J Physiol Renal Physiol, 2013.
39. Horwitz, E. M., et al., *Clarification of the nomenclature for MSC: The International Society for Cellular Therapy position statement.* Cytotherapy, 2005. 7(5): p. 393-5.
40. Morrison, S. J. and D. T. Scadden, *The bone marrow niche for haematopoietic stem cells.* Nature, 2014. 505(7483): p. 327-34.
41. Mendez-Ferrer, S., et al., *Mesenchymal and haematopoietic stem cells form a unique bone marrow niche.* Nature, 2010. 466(7308): p. 829-34.
42. Zhu, H., et al., *A protocol for isolation and culture of mesenchymal stem cells from mouse compact bone.* Nat Protoc, 2010. 5(3): p. 550-60.
43. Horwitz, E. M., et al., *Isolated allogeneic bone marrow-derived mesenchymal cells engraft and stimulate growth in children with osteogenesis imperfecta: Implications for cell therapy of bone.* Proc Natl Acad Sci USA, 2002. 99(13): p. 8932-7.
44. Schrepfer, S., et al., *Stem cell transplantation: the lung barrier.* Transplant Proc, 2007. 39(2): p. 573-6.
45. Mohanty, S. T. and I. Bellantuono, *Intra-femoral injection of human mesenchymal stem cells.* Methods Mol Biol, 2013. 976: p. 131-41.
46. Brandi, A., et al., *Oxidative stress induces senescence in human mesenchymal stem cells.* Exp Cell Res, 2011. 317(11): p. 1541-7.
47. Lepperdinger, G., *Inflammation and mesenchymal stem cell aging.* Curr Opin Immunol, 2011. 23(4): p. 518-24.
48. Kasper, G., et al., *Insights into mesenchymal stem cell aging: involvement of antioxidant defense and actin cytoskeleton.* Stem Cells, 2009. 27(6): p. 1288-97.
49. Sharpless, N. E. and R. A. DePinho, *How stem cells age and why this makes us grow old.* Nat Rev Mol Cell Biol, 2007. 8(9): p. 703-13.
50. Popova, A. P., et al., *Autocrine production of TGF-beta1 promotes myofibroblastic differentiation of neonatal lung mesenchymal stem cells.* Am J Physiol Lung Cell Mol Physiol, 2010. 298(6): p. L735-43.
51. Crowder, S. W., et al., *Passage-dependent cancerous transformation of human mesenchymal stem cells under carcinogenic hypoxia.* Faseb J, 2013. 27(7): p. 2788-98.
52. Russell, K. C., et al., *In vitro high-capacity assay to quantify the clonal heterogeneity in trilineage potential of mesenchymal stem cells reveals a complex hierarchy of lineage commitment.* Stem Cells, 2010. 28(4): p. 788-98.

Example 2: Perivascular Mesenchymal Stem Cells Drive Solid Organ Fibrosis

The development of therapies to treat fibrotic disease is limited by controversy regarding the identity of the cellular progenitors of myofibroblasts, which are the cells that ultimately drive matrix deposition and contribute to loss of organ function. Here the inventors show that perivascular mesenchymal stem cells (MSC) are myofibroblast progenitors, as they differentiate into myofibroblasts during solid organ fibrosis. The inventors identified Gli1 as a specific marker of MSC across organs and they provide genetic lineage analysis evidence that MSC undergo proliferative expansion during kidney, lung, liver and heart fibrosis. Genetic ablation of Gli1+ perivascular MSC ameliorates kidney fibrosis and preserves ejection fraction in aortic-constriction-induced congestive heart failure. These findings implicate perivascular Gli1+ MSC as the cellular origin of organ fibrosis and a novel therapeutic target.

Organ fibrosis occurs in virtually all chronic diseases and represents a major clinical problem and unmet clinical need. Myofibroblasts are widely viewed as a critical cell type in organ fibrosis, since they secrete extracellular matrix and proliferate at sites of injury. Historical observations suggest that fibrosis emanates from blood vessels (1, 2). This notion has received support from lineage tracing studies that have implicated vascular pericytes as myofibroblast progenitors in the kidney (3), lung (4), spinal cord (5), dermis and skeletal muscle (6). Whether or not pericytes represent the sole myofibroblast progenitor is unclear (7), and in fact, whether or not pericytes contribute to fibrosis at all has recently been questioned (8). Mesenchymal stem cells (MSC) are pericytes and reside in the perivascular niche (9). The inventors therefore hypothesized that MSC represent a myofibroblast progenitor population. The absence of a single marker for MSC has challenged investigation of the functional contributions of these cells to fibrosis in vivo, however.

Figure 8A:
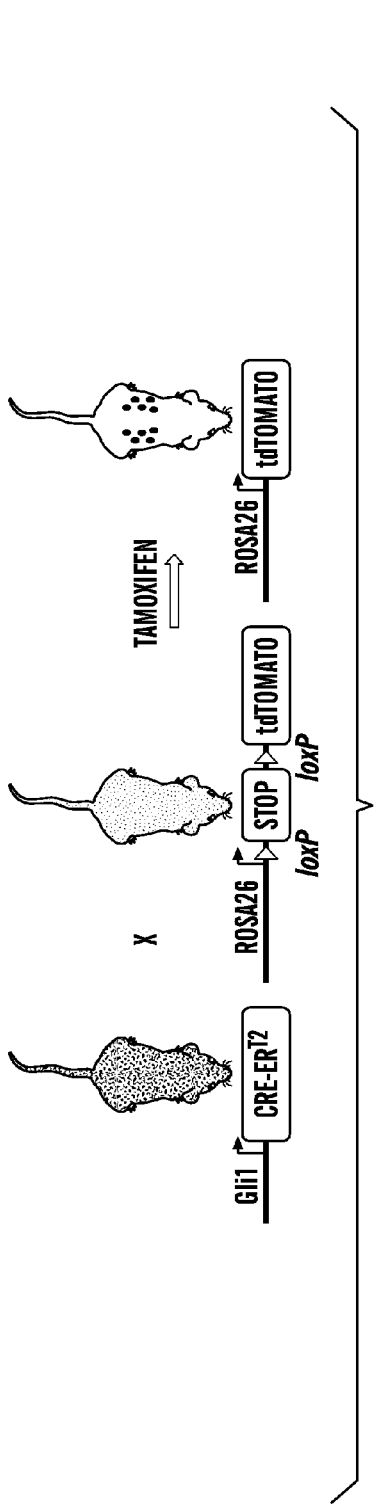
FIGS. 8A-8C show that Gli1 defines a specific perivascular mesenchymal stem cell population.
Figure 8B:
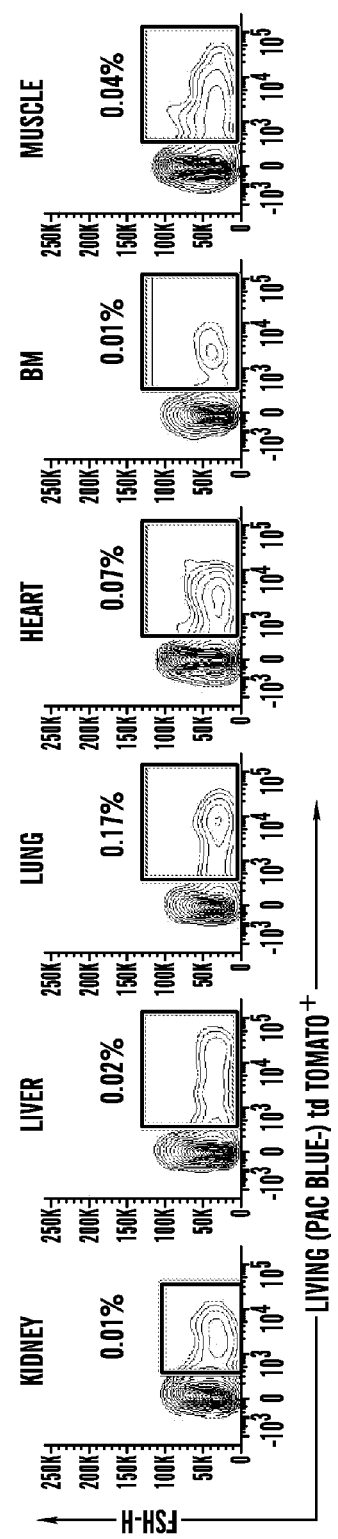
Figure 8B:
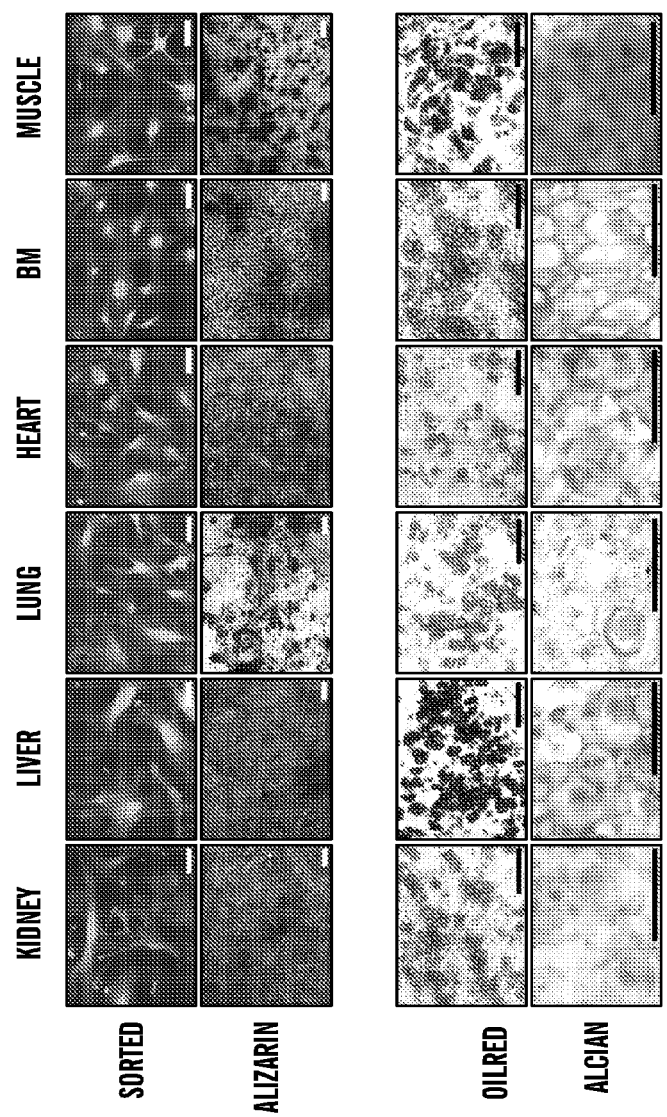
Figure 12:
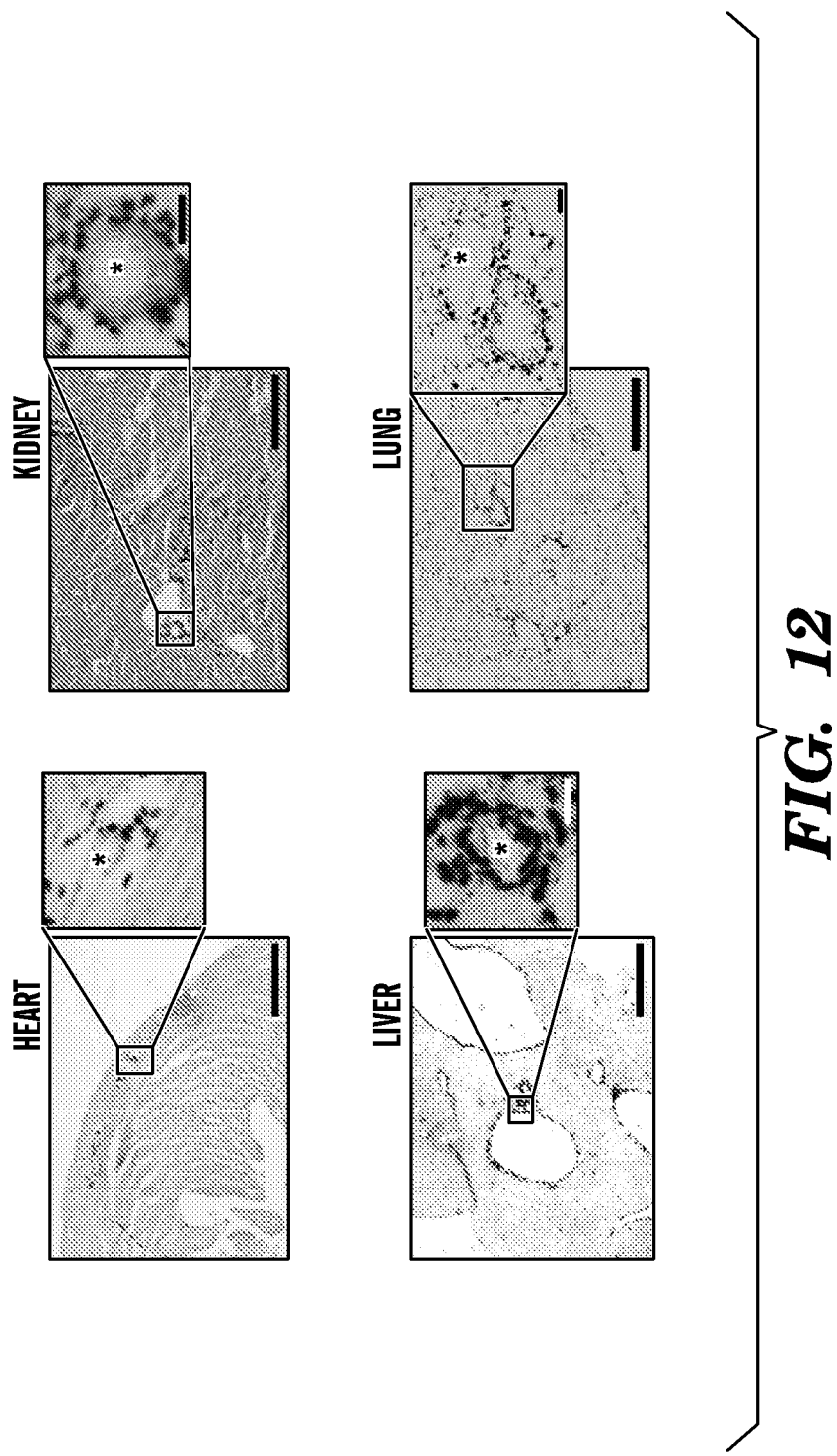
FIG. 12 shows representative X-gal stained tissue sections from the Gli1-nLacZ mouse indicating Gli1 expressing cells are specifically located around the vasculature (asterisks=arteries).

While examining expression patterns of Hedgehog pathway constituents in histological samples, the inventors observed that Gli1 is specifically expressed in cells surrounding vasculature, from microvascular capillaries to large arteries in various organs (FIG. 12). The perivascular localization and low frequency of these cells suggested a possible MSC identity. To comprehensively assess the distribution of these cells in solid organs and tissues, the inventors crossed Gli1-CreERt2 driver mice to a tdTomato a reporter mouse for genetic labeling. Gli1+ cells from bigenic Gli1-CreERt2; R26tdTomato mice were located in the perivascular niche across all major organs and tissues (FIGS. 8A-B). In kidney, liver, lung, heart, bone-marrow and skeletal muscle Gli1+ cells are either (1) intimately associated with microvasculature and in direct contact to CD31+ endothelial cells or (2) localized in the adventitia of arteries distant from endothelial cells (data not shown). Aside from their perivascular localization, Gli1+ cells were also positioned around biliary ducts of the liver and around larger airways of the lung (bronchi and bronchioles) (data not shown). Gli1+ cells consistently express the mesenchymal marker PDGFR-β. Fluorescence microangiography confirms the close apposition of the majority of Gli1+ cells to the capillary lumen of kidney and heart.

Figure 8C:
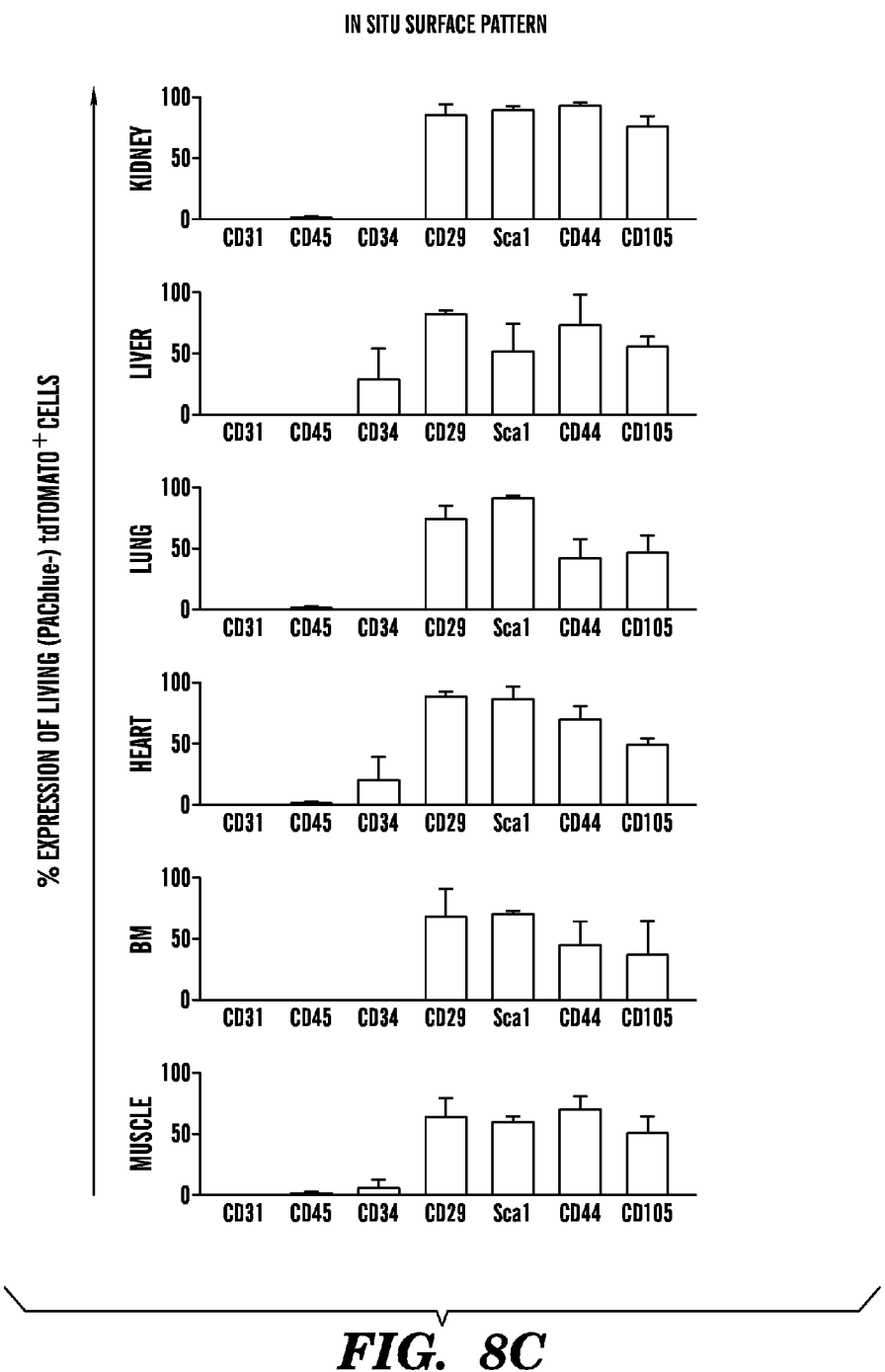
Figure 9A:
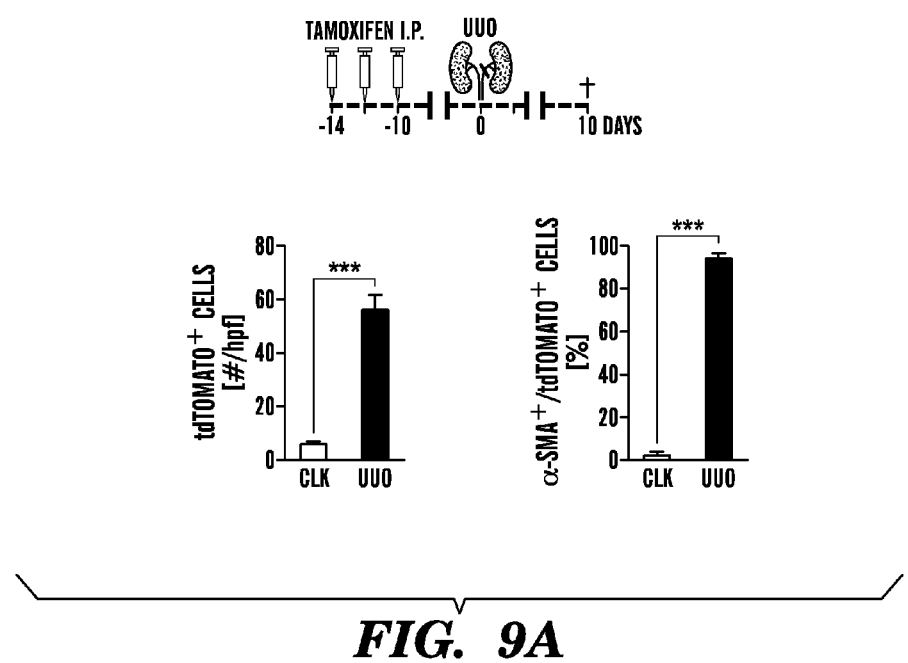
Figure 13A:
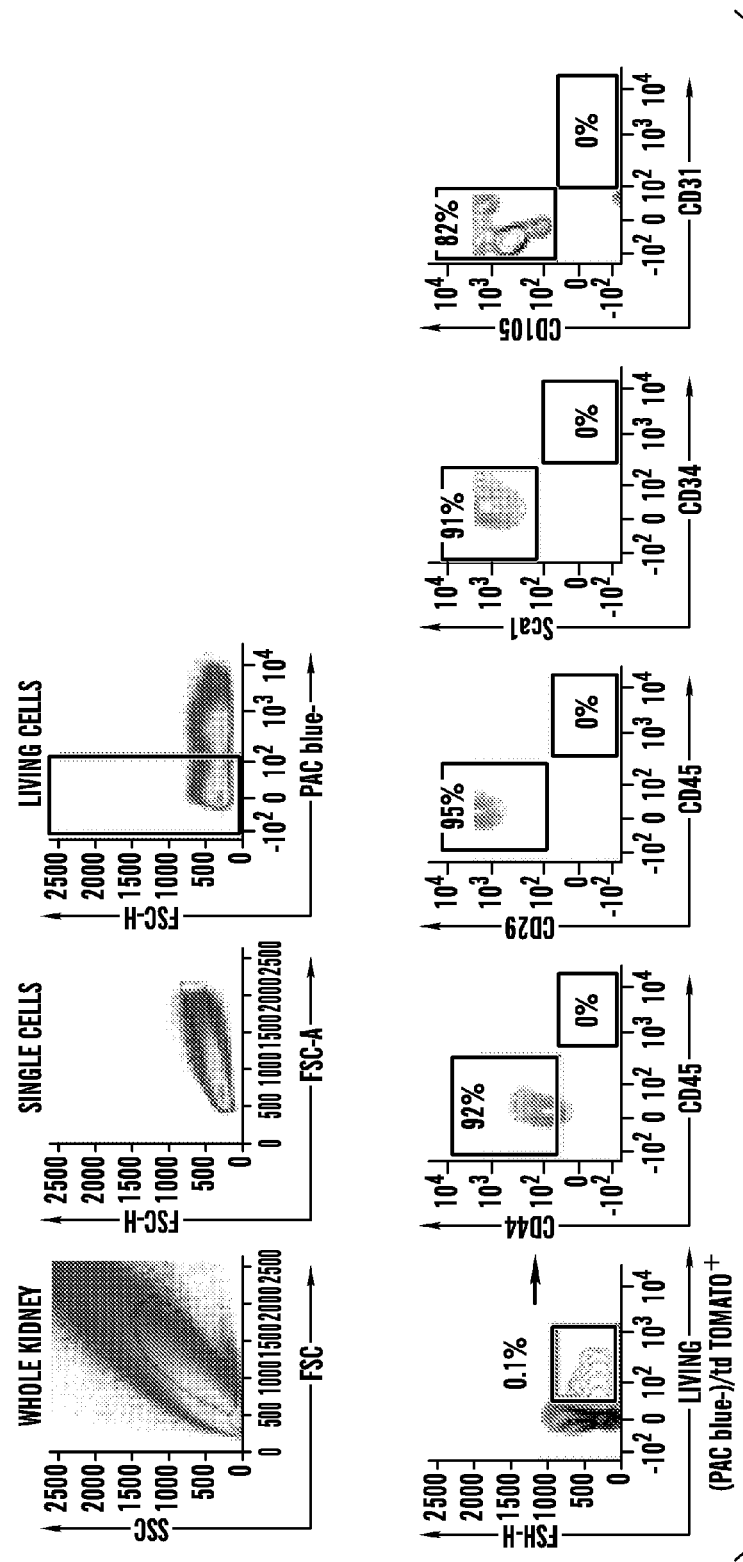
Figure 13D:
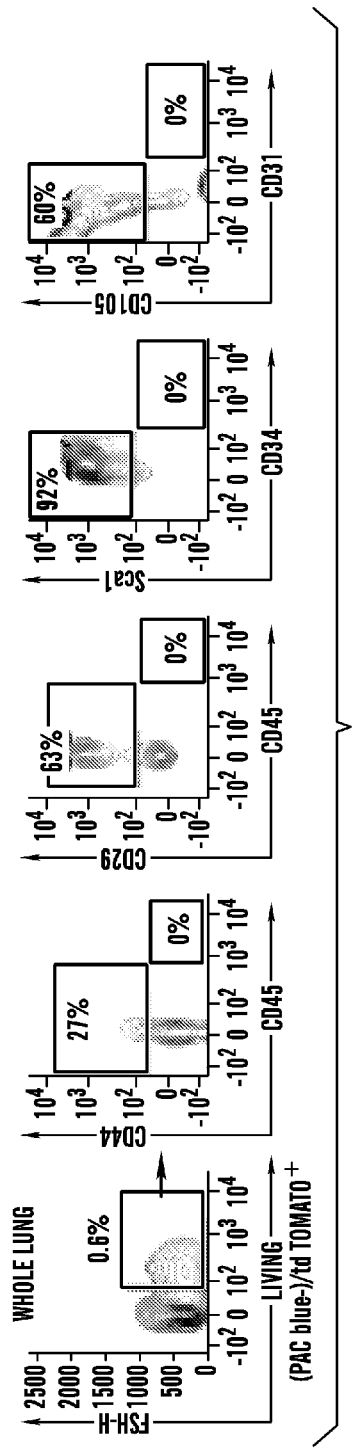
Figure 14A:
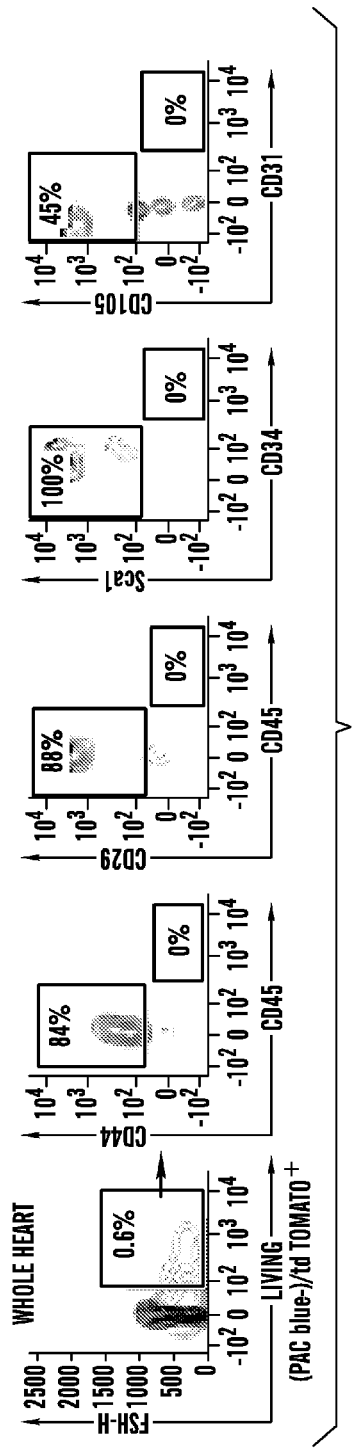
FIGS. 14A-14C show representative gating and plots of whole organ flow cytometry from heart, bone marrow and muscle. Representative flow cytometric plots for whole digested heart, whole bone marrow following crushing of the femoral bones, tibia and pelvis and whole digested skeletal muscle (musculus gastrocnemius).
Figure 14B:
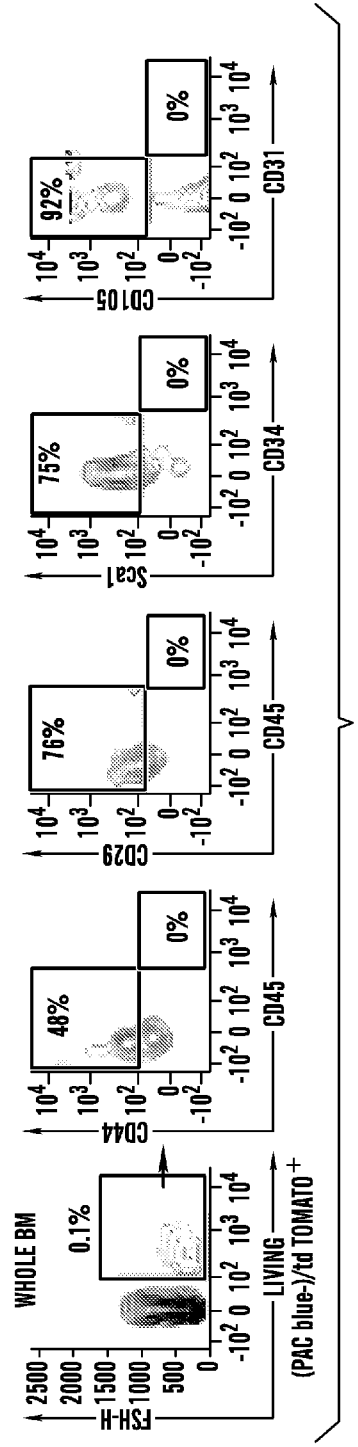
Figure 14C:
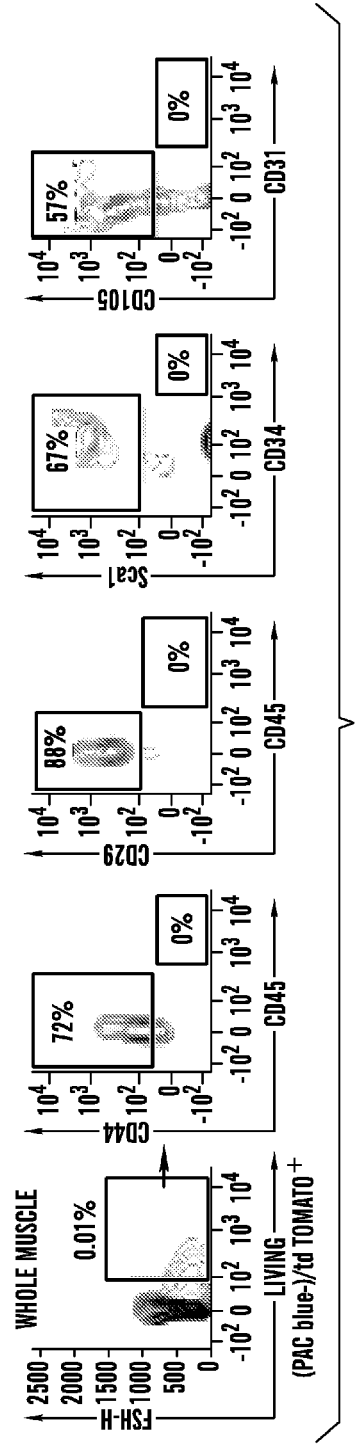

Fluorescence activated cell-sorting (FACS) of whole digested organs and tissues demonstrates similar frequencies of Gli1+ cells across different organs and tissues ranging from 0.01% of gated events in kidney and bone-marrow to 0.17% of gated events in the lung (FIG. 8B). To characterize Gli1+ cells by accepted criteria defined for MSC, the inventors cultured sorted Gli1+ cells and demonstrated their trilineage differentiation capacity toward chondrocytes, adipocytes and osteoblasts regardless of their tissue origin (FIG. 8B). Further, the inventors performed whole organ flow-cytometry and confirmed the expression of typical MSC markers including CD29, CD44, CD105 and Sca1 in the Gli1+ cell-population without pre-culture of the cells (FIG. 8C, representative plots and gating for each organ is shown in FIGS. 13-14).

Figure 15A:
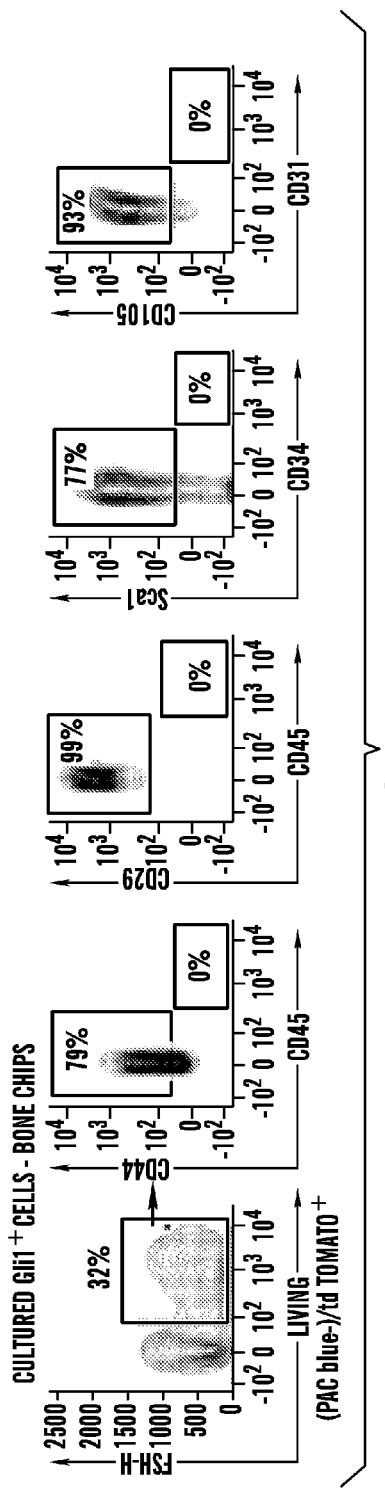
Figure 15B:
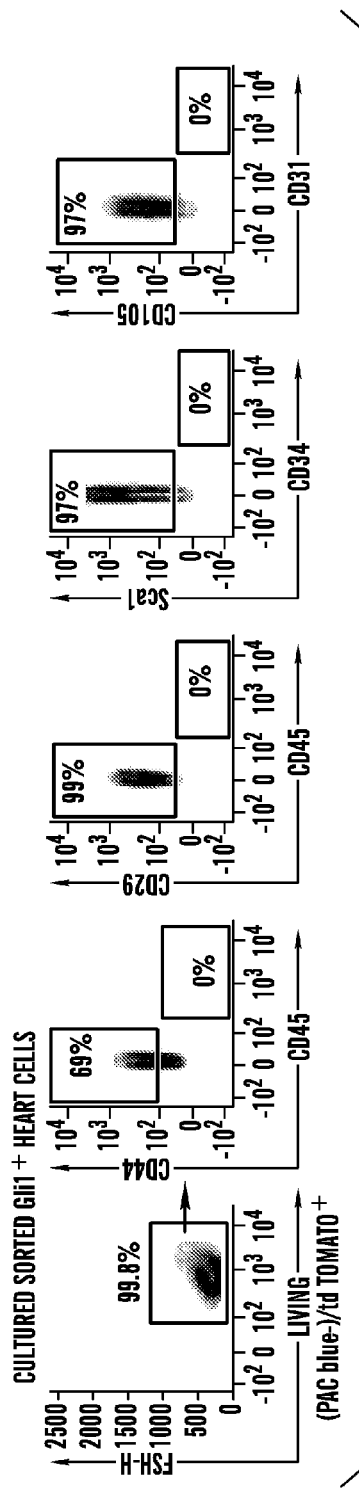

In the bone marrow niche, MSC surround blood vessels and sinusoids but also line endosteum (10, 11). The inventors observed Gli1+ cells lining CD31+ endothelial cells of all bone marrow sinusoids as well as endosteum of the compact bone (data not shown), representing both the vascular and the endosteal niche. Since mouse bone marrow (BM-) MSC in the endosteal niche cannot readily be isolated from the bone marrow, the inventors applied an endosteal bone chip method for their liberation (12). Interestingly, Gli1+ cells migrated out of the bone fragments and proliferated in the culture dish (data not shown). Flow cytometric analysis of these cells indicated that ≈32% had a Gli1+ origin (FIG. 15 A). MSC isolated from bone chips (BM-MSC) as wells as isolated from the myocardium (h-MSC) maintained their typical MSC surface pattern in culture (FIGS. 15A-B). Upon treatment with transforming growth factor beta (TGF-β) both BM-MSC and h-MSC acquired expression of the myofibroblast marker alpha smooth muscle actin (α-SMA, FIGS. 15C-15D). In aggregate, these observations indicate that Gli1 expression defines an MSC population across tissues and organs including bone marrow.

Although a great deal is known regarding the in vitro characteristics of MSC, and indeed MSC are currently being investigated as cell therapy in over a hundred clinical trials, relatively little is known concerning their role in vivo. The inventors performed genetic fate-tracing studies of MSC following induction of chronic injury models to kidney (unilateral ureteral obstruction (UUO) and severe bilateral ischemia reperfusion injury (IRI)), heart (angiotensin-2 (AT2) induced myocardial fibrosis, ascending aortic constriction (AAC)), liver (carbon tetrachloride (CCL4) induced fibrosis) and lung (intratracheal bleomycin instillation). The inventors genetically labeled Gli1+ MSC before injury via tamoxifen injection and followed the fate of recombined cells for up to 52 days. The injury was induced at least 10 days after tamoxifen administration to exclude the possibility of recombination after injury (5). Gli1+ MSC dramatically expanded upon injury of all major organs and acquired α-SMA expression during fibrogenesis in kidney, lung, liver and heart (FIGS. 9 and 16-18). Ki67 staining demonstrates that Gli1+ MSC expand through proliferation during injury (data not shown).

Figure 10C:
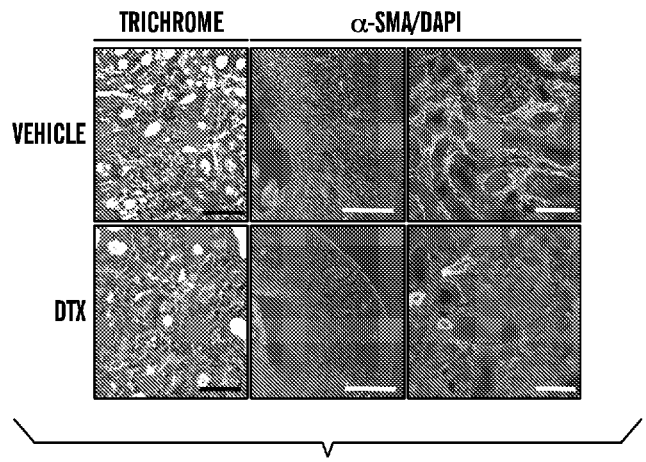
Figure 10D:
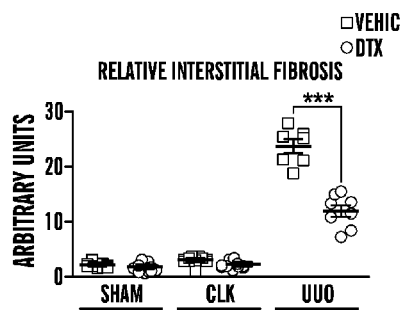
Figure 10F:
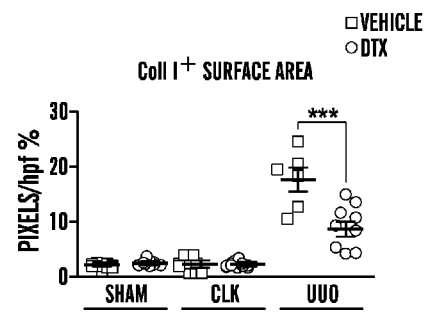
Figure 10E:
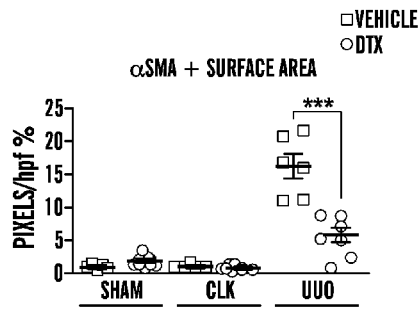
Figure 10G:
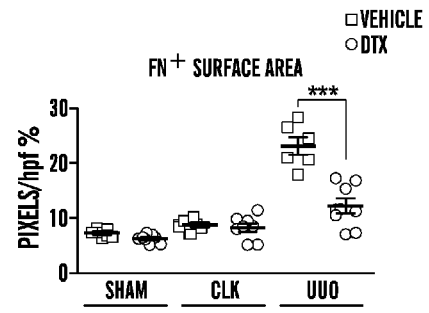

In order to assess the functional contribution of MSC to fibrosis and loss of organ function, the inventors generated mice expressing the human diptheria toxin receptor (HB-EGF) in Gli1+MSC (Gli1CreER$^{t2}$, iDTR). This strategy enabled us to ablate Gli1+MSC following injury by administration of diptheria toxin (DTX). High dose tamoxifen was administered to Gli1CreER$^{t2}$, iDTR mice before they were subjected to either UUO or sham surgery. Following surgery, mice were injected DTX or vehicle (PBS) as indicated (FIG. 10B). Successful ablation of MSC following UUO was verified by quantitative realtime PCR for HB-EGF. Strikingly, significantly reduced renal fibrosis was observed in kidneys from mice receiving DTX compared to vehicle (FIGS. 10C-10L).

Figures 11G, 11H, 11I, 11J:
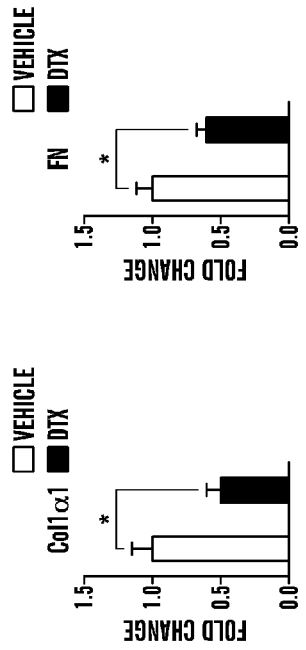
Figure 11L:
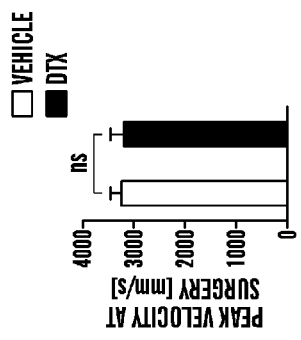
FIG. 11L. Immediately after the surgery, the peak velocity at the AAC suture did not differ between the groups indicating a similar grade of banding severity.
Figure 11K:
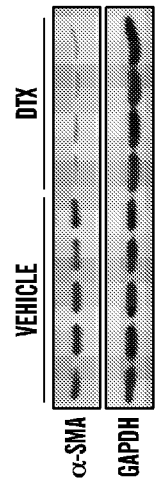
FIG. 11K. Western blot analysis for α-SMA expression.
Figure 11M:
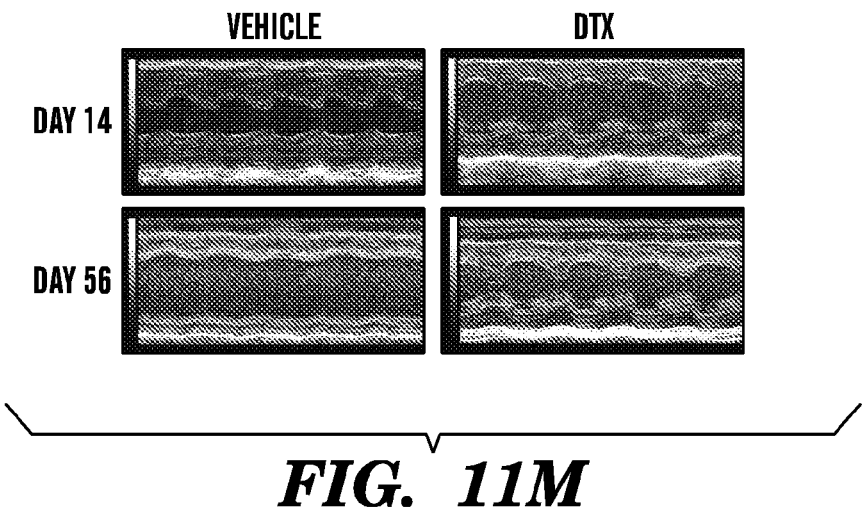
Figure 11N:
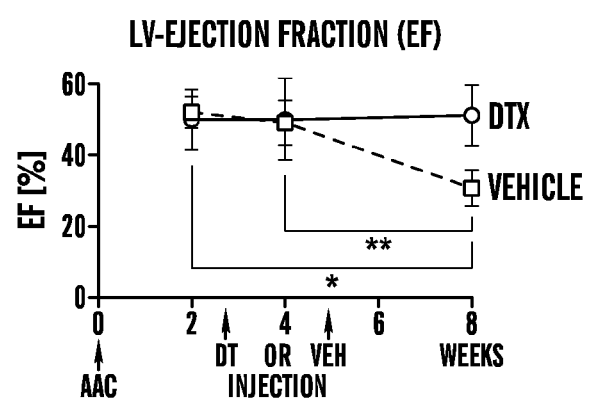

To ask whether ablation of MSC can improve organ function during chronic disease, the inventors utilized the AAC model of heart fibrosis, which enables the non-invasive monitoring of cardiac function via echocardiography. Gli1CreER$^{t2}$; iDTR mice were injected with high dose tamoxifen and subject to AAC surgery followed by injection of DTX or vehicle (FIG. 11A). Ablation of Gli1+ MSC and their descendant myofibroblasts ameliorated cardiac hypertrophy and myocardial fibrosis (FIGS. 11A-11J). Remarkably, echocardiographic analysis of the left ventricular function demonstrated that ablation of MSC rescued chronic heart failure by preserving left ventricular ejection fraction and thus, myocardial function (FIGS. 11L-11N). The inventors conclude that expansion of perivascular Gli1+ MSC and their differentiation into myofibroblasts contributes to scar forming fibrosis and chronic organ failure whereas ablation of this specific cell-type can ameliorate disease progression and rescue organ function.

The inventors have identified perivascular MSC as a source of scar-forming myofibroblasts across major organs and tissues. Recent studies identified Gli1 as a marker of perivascular MSC in the mouse incisor (13), which in light of these current findings indicates that Gli1 is a general marker for MSC during adult homeostasis. The inventors conclude that during conditions of chronic injury, MSC differentiate into myofibroblasts contributing to scar and loss of organ function Eliminating Gli1+ MSC under chronic injury conditions reduced fibrosis and preserved organ function indicating that Gli1+ MSC are a promising cellular target for novel anti-fibrotic therapies.

Materials and Methods

Animals.

All mouse experiments were performed according to the animal experimental guidelines issued by the Animal Care and Use Committee at Harvard University. Gli1-nLacZ (i.e., Gli1$^{tm2Alj}$/J, JAX Stock 008211) Gli1CreER$^{t2}$ (i.e., Gli1$^{tm3(re/ERT2)Alj}$/J, JAX Stock #007913), Rosa26tdTomato (i.e., B6-Cg-Gt(ROSA)26Sort$^{tm(CAG-tdTomato)Hze}$/J JAX Stock #007909) iDTR mice (i.e., C57BL/6-Gt(ROSA) 26Sor$^{tm1(HBEGF)Awai}$/J, JAX Stock #007900) were purchased from Jackson Laboratories (Bar Harbor, Me.). Offspring were genotyped by PCR according to the protocol from the Jackson laboratory.

Mouse Models of Solid Organ Fibrosis.

For lineage tracing studies 6-7 week old mice received 3×0.1 mg/kg bodyweight tamoxifen in corn oil/3% ethanol (Sigma) via intraperitoneal injection 10 days before surgery or disease induction. Unilateral ureteral obstruction (UUO) surgery was performed as previously described (14). Briefly, after flank incision the left ureter was tied off at the level of the lower pole with two 4.0 silk ties. Mice were sacrificed at day 10 after surgery. For the unilateral ischemia re-perfusion injury (IRI), mice were anesthetized with pentobarbital sodium (60 mg/kg body weight, intraperitoneally), the left kidney was exposed through flank incision and subjected to ischemia by clamping the renal pedicle with nontraumatic microaneurysm clamps (Roboz, Rockville, Md.) for 35 min. Body temperatures were controlled at 36.5° C.-37.5° C. throughout the procedure. For the mouse model of angiotensin 2 induced myocardial fibrosis, the inventors implanted osmotic minipumps (Alzet Model 2004) infusing angiotensin 2 (Sigma) dissolved in sterile normal saline (Baxter) at a rate of 1000 ng/kg/min subcutaneously during a ketamine/xylazine (100/13 mg/kg bodyweight) anesthesia. Osmotic minipumps containing normal saline were implanted in control animals. Mice were euthanized at 28 days after surgery. Ascending aortic constriction (AAC) was performed in the Cardiovascular Facility of the Brigham and Women's Hospital as previously described (15). Briefly, mice were anesthetized with 3% isoflurane, intubated and ventilated on a Harvard rodent respirator (Type 845, Hugo Sachs Elektronik, March, Germany) An incision was made at the third intercostal space and ribs were gently spread with a micro dissecting retractor (Biomedical Research Instruments). The ascending aorta was then isolated from the pulmonary artery approximately 3 mm from the base of the heart and ligated around a blunted 27 gauge needle using 8-0 suture (Prolene, ETHICON). The ribs, chest musculature and skin was closed using 5-0 Dexon and 6-0 Prolene suture (ETHICON). Sham-operated mice underwent the same procedure without ligation of the ascending aorta. For the model of bleomycin-induced lung fibrosis, mice were anesthetized with ketamine/xylazine (100/13 mg/kg bodyweight intraperitoneally) and the trachea was exposed by cervical incision. Bleomycin (Hospira) was dissolved in normal saline and intratracheally instilled via a 29 gauge needle at a dose of 2.5 U/kg bodyweight. Mice were euthanized at day 14 and lungs were perfused with Periodate Lysine-Paraformaldehyde (PLP) buffer and inflated to 25 cm $H_2O$ trough the trachea. After ligation of the trachea (3-0 suture) the lungs were immersed in PLP for 2 hours on ice, placed in 18% sucrose over night, and OCT embedded. Control mice underwent the same procedure but were instilled with normal saline. Liver injury and fibrosis was induced by intraperitoneal injection of carbon tetrachloride ($CCl_4$, Sigma dissolved in mineral oil 1:3) at a dose of 1 µl/g twice weekly for 4 weeks. Control mice received intraperitoneal injections of mineral oil (SIGMA) alone. For all surgical procedures mice received buprenorphine (0.1 mg/kg bodyweight subcutaneously) to achieve analgesia.

Cell Specific Ablation Experiments.

For all ablation experiments, bigenic Gli1 CreERt2; iDTR mice received tamoxifen (3×0.4 mg/kg per oral gavage) 10 days before surgery and were then injected with diphtheria toxin dissolved in PBS (List Biological Laboratories) at a dose of 50 ng/g bodyweight intraperitoneally as indicated (i.e., at day 3, 5, 7 following UUO and days 16, 18, 37, 39 following AAC surgery). Control mice received intraperitoneal injections of PBS.

Tissue Preparation and Histology.

Mice were anesthetized with isofluorane (Baxter) and subsequently perfused via the left ventricle with 4° C. PBS for 1 minute. For histological analyses tissue sections were fixed in 10% formaldehyde for 1 h, paraffin embedded and cut with a rotating microtome at 3 µm thickness and stained according to routine histology protocols. For immunofluorescence studies kidneys were fixed in 4% paraformaldehyde on ice for 1 hour, then incubated in 30% sucrose in PBS at 4° C. overnight. OCT-embedded (SAKURA FINETEK) tissues were cryosectioned into 7 µm sections and mounted on Superfrost slides (FISHER SCIENTIFIC). Sections were washed in 1×PBS, blocked in 10% normal goat serum (VECTOR LABS) and incubated with primary antibodies specific for Ki-67 (VECTOR LABS Cat. #VP-RM04), alpha SMA (SIGMA, Cat No. A2547), alpha SMA-FITC (SIGMA, # F3777), fibronectin (ABCAM #ab23750), collagen1α1 (SOUTHERN BIOTECHNOLOGY #1310-01), DsRed (CLONTECH #632496). Secondary antibodies were FITC-, Cy3, or Cy5-conjugated (JACKSON IMMUNORESEARCH). Sections were then stained with DAPI (4',6'-'diamidino-2-phenylindole) and mounted in Prolong Gold (LIFE TECHNOLOGIES).

For quantification of cell expansion pictures (400×, n=5/organ) were taken as follows: in the kidney models random pictures of the inner cortex and outer medulla, in the angiotensin 2 model of myocardial fibrosis random pictures around arteries i.e., periarterial; in the AAC model random pictures of the interstitial myocardium (excluding arteries), in the liver-fibrosis model random pictures around central veins and the periportal field and in the bleomycin induced lung fibrosis model random pictures of interstitial lung (excluding large bronchi) were taken. Positive cells were counted manually using Image J (NIH). Quantification of α-SMA, collagen I and fibronectin positive surface area was performed by taking random pictures (400×, n=5 per organ) of each mouse using the number of stained pixels per total pixels in Adobe Photoshop CS5 (ADOBE SYSTEMS, Inc., San Jose, Calif.). All images were obtained by confocal (Nikon C1 eclipse, Nikon, Melville, N.Y.) or standard microscopy (Nikon eclipse 90i). Fibrosis severity was scored at 400× magnification using a counting grid with 117 intersections (for the kidney 5 random pictures of the inner cortex, for the heart 6 pictures of different left ventricular regions i.e., anterior, anteroseptal, inferoseptal, inferior, inferolateral were used). The number of grid intersections overlying trichrome positive (blue) interstitial area was counted and expressed as a percentage of all grid intersections. For this calculation in the kidney intersections that were in tubular lumen and glomeruli were subtracted from the total number of grid intersections. Cardiomyocyte cross sectional area was determined by measuring the cell surface area of 10 random cardiomyocytes in 400× pictures of the myocardium (3 trichrome stained pictures/heart) using Image J (NIH).

To identify LacZ activity in tissue sections, PFA fixed frozen sections were incubated in standard 5-bromo-4-chloro-3-indolyl-β-d-galactoside (X-gal) for 48 hours counterstained with nuclear fast red and mounted. Fluorescence microangiography was performed as recently described (16).

Flow Cytometry and Cell Sorting.

For flow cytometric analysis or fluorescence activated cell sorting (FACS) of whole organs and tissues mice were euthanized as described above, perfused with sterile PBS via the left ventricle and the organs of interest were placed in FACS Buffer (PBS, 10% FBS, 2% Penicillin Streptomycin, LIFE TECHNOLOGIES). After thoroughly mincing the tissue/organ using a sterile scalpel (Feather), the tissue/organ was placed in GENTLEMACS C Tubes (MILTENYI BIOTEC) containing 1.5 ml DMEM (LIFE TECHNOLOGIES) with 0.1 mg/ml LIBERASE TL (ROCHE). The tissue was then dissociated using the D program of the GENTLEMACS dissociator (MILTENYI BIOTEC) followed by 30 min incubation at 37° C. Following washing steps with FACS buffer and centrifugation (1500 rpm 5 min) the solution was filtered twice trough a 40 μm cell strainer (BD BIOSCIENCES) and transferred to 5 ml Polystyrene Round-Bottom FACS tubes (BD BIOSCIENCES). FACS sorting was performed using the FACSAria II cell sorter (BD BIOSCIENCES). For flow cytometric studies the samples were stained in 100-500 μl FACS Buffer using the following fluorochrome conjugated antibodies: CD31-APC (BIOLEGEND #102410), CD45-FITC (EBIOSCIENCE #17-0291-82), CD34-FITC (EBIOSCIENCE #11-0341-85), CD29-APC (EBIOSCIENCE #17-0291-82), Sca1-APC-Cy7 (BIOLEGEND #108126), CD44-PE-Cy7 (EBIOSCIENCE #25-0441-82), CD105-PE-Cy7 (BIOLEGEND #120410), all 1:100 for 30 min followed by a washing step with FACS buffer. All flow cytometric analyses were performed at a LSR II Flow Cytometer (BD BIOSCIENCES). For all flow cytometric analyses and FACSorting DAPI (1 mg/ml 1:1000) was added in order to exclude dead cells. Data were analyzed by using Flow Jo software (Version 9.6.2, TREE STAR Inc).

Cell Culture Experiments.

All cells were grown in alpha MEM (GLUTAMAX, LIFE TECHNOLOGIES) containing 20% MSC qualified FBS (LIFE TECHNOLOGIES), 2% Penicillin Streptomycin (LIFE TECHNOLOGIES), 1 ng/ml murine basic fibroblast growth factor (THERMO FISHER SCIENTIFIC) and 5 ng/ml murine epidermal growth factor (PEPROTECH). Bone marrow MSC were isolated from compact bone chips of femur, tibia and pelvis according to the protocol by Zhu et al. (12). For osteogenic or adipogenic differentiation FACSorted cells were plated in a 48 well, at a 60-70% or 90-100% confluency the alpha MEM medium was exchanged with osteogenic or adipogenic differentiation medium, respectively (R&D SYSTEMS). After 21 days of cultivation the cells were stained according to routine protocols using Oilred 0 or Alizarin red (SIGMA). For chondrogenic differentiation $2-10 \times 10^4$ cells were resuspended in 1 ml chondrogenic differentiation medium (R&D SYSTEMS) in a 15 ml conical tube (BD BIOSCIENCES) and centrifuged at 1500 rpm for 5 min. The cell-pellets were cultivated upright in the 15 ml conical for 21 days. For detection of chondrogenic differentiation the cell-pellet was fixed in 4% paraformaldehyde. OCT-embedded (SAKURA FINETEK) cell-pellets were cryosectioned into 4 μm sections and mounted on SUPERFROST slides. After PBS washing the sections were stained with ALCIAN blue (SANTA CRUZ BIOTECHNOLOGY) and counterstained with nuclear fast red (SIGMA). For studying the α-SMA gene-expression in vitro FACS sorted tdTomato+ cells from heart or kidney were cultured in 6 wells serum starved over night (0.5% FBS) and treated with 10 ng/ml transforming growth factor beta (TGF-β) or vehicle for 24 hours. For α-SMA staining cells were grown on coverslips (FISHER) coated with collagen I (BD BIOSCIENCES) and treated with the above mentioned dose of TGF-β for 72 hours.

Real Time PCR Experiments.

Tissue or cell-pellets were harvested and immediately snap frozen in liquid nitrogen. RNA from kidneys or cell-culture was extracted according to the manufacturer instructions using the RNeasy Mini Kit (QIAGEN) and 600 ng of total RNA was reverse transcribed with iScript (BIORAD). RNA from hearts (left ventricle) was isolated using TRIZOL Reagent (LIFE TECHNOLOGIES) according to the manufacturer instructions. Following or during the RNA extraction DNA was removed by a DNAse digestion step (LIFE TECHNOLOGIES). Quantitative polymerase chain reactions were carried out with iQ-SYBR Green supermix (BIORAD) and the BIORAD CFX96 Real Time System with the C1000 Touch Thermal Cycler. Cycling conditions were 95° C. for 3 minutes then 40 cycles of 95° C. for 15 seconds and 60° C. for 1 minute, followed by one cycle of 95° C. for 10 seconds. Glyceraldehyde-3-phosphate dehydrogenase (GAPDH) was used as a housekeeping gene. Data was analyzed using the 2-ΔΔct method. Primers are listed in Table 1.

TABLE 1

Primer pairs used for qt-RT-PCR.

| Gene | Sequence |
| --- | --- |
| GAPDH | Fw 5'-AGGTCGGTGTGAACGGAT TTG-3' (SEQ ID NO: 1)<br>Rv 5'-TGTAGACCATGTAGTTGA GGTCA-3' (SEQ ID NO: 2) |
| iDTR (HB-EGF) | Fw 5'-GGAGCACGGGAAAAGAAA G-3' (SEQ ID NO: 3)<br>Rv 5'-GAGCCCGGAGCTCCTTCA CA-3' (SEQ ID NO: 4) |

TABLE 1-continued

Primer pairs used for qt-RT-PCR.

| Gene | Sequence |
|---|---|
| Col1α1 | Fw 5'-TGACTGGAAGAGCGGAGAGT-3' (SEQ ID NO: 5)<br>Rv 5'-GTTCGGGCTGATGTACCAGT-3' (SEQ ID NO: 6) |
| fibronectin | Fw 5'-ATCTGGACCCCTCCTGATAGT-3' (SEQ ID NO: 7)<br>Rv 5'-GCCCAGTGATTTCAGCAAAGG-3' (SEQ ID NO: 8) |
| α-SMA | Fw 5'-CTGACAGAGGCACCACTGAA-3' (SEQ ID NO: 9)<br>Rv 5'-CATCTCCAGAGTCCAGCACA-3' (SEQ ID NO: 10) |

Western Blot.

Tissue was snap frozen in liquid nitrogen immediately after mice were euthanized and stored at −80° C. Kidney tissue samples were homogenized in lysis buffer containing 10 mM HEPES, pH 7.4, 0.32M sucrose, 2 mM EDTA, 1 mM DTT, 1 mM PMSF and 1 protease inhibitor tablet per 10 ml of lysis buffer (ROCHE Cat. No. 11836153001). Protein from heart tissue samples (left ventricles) was isolated via precipitation from the TRIZOL Reagent as described elsewhere (17). The samples were sonicated and protein concentration was determined by the Bradford Assay using BIORAD Protein Assay Dye (BIORAD). 10-20 µg of protein from lysates was loaded on a 10% polyacrylamide gel and separated by SDS electrophoresis. Proteins were transferred to an IMMOBILON membrane (MILLIPORE) blocked in 5% milk in PBST, probed overnight at 4° C. with the primary antibodies: mouse anti-αSMA at 1:4000 (SIGMA #A2547) and rabbit anti-GAPDH at 1:4000 (BETHYL LABORATORIES, #A300-641A). Following incubation with primary antibody blots were washed probed with respective horseradish-peroxidase conjugated secondary antibodies at 1:4000 (DAKO, Cat. No. P0447, P0448) for 1 hour at room temperature and then visualized using the Western Lightning ECL kit from PERKIN ELMER (#NEL100001EA).

Echocardiography.

Echocardiography was performed in the AAC cell-ablation experiment immediately following the AAC surgery to determine the peak velocity at the constriction, 2 weeks after surgery before the randomization to DTX or Vehicle group and at 4 and 8 weeks after the surgery in low dose isoflurane anesthesia (1.5%) using a 28 MHz linear array transducer connected to a digital ultrasound console (VEVO 2100 VISUALSONICS). Mice were gently restrained on a heated platform and pre-warmed ultrasound gel was used on their depilated chest. B-Mode loops were acquired from parasternal short and long-axis views and M-Mode images were recorded from parasternal short-axis view at the mid-papillary level. Peak velocity at the suture was determined by pulse waved (PW) Duplex sonography of the ascending aorta using color duplex sonography as a guide for detecting the area of strongest turbulence. Images and loops were stored and analyzed offline using the Vevo 2100 analysis software (1.6.0 VISUALSONICS). Left ventricular ejection fraction (EF) was calculated by identification of frames with the maximal and minimal cross-sectional area and width in the parasternal long axis view as described before (18).

Statistical Analysis.

Data are presented as mean±SEM. Comparison of two groups was performed using unpaired t-test. Paired t-test was used for comparison of repeated measured in the same group. For multiple group comparison analysis of variance with posthoc Tukey correction was applied. Statistical analyses were performed using GraphPad Prism 5.0c (GRAPHPAD Software Inc., San Diego, Calif.). A p value of less than 0.05 was considered significant.

REFERENCES FOR EXAMPLE 2

1. J. B. Maccallum, A Contribution to the Knowledge of the Pathology of Fragmentation and Segmentation, and Fibrosis of the Myocardium. The Journal of experimental medicine 4, 409 (May 1, 1899).
2. R. Atkins, On Arterio-Capillary Fibrosis. British medical journal 1, 444 (Apr. 3, 1875).
3. B. D. Humphreys et al., Fate tracing reveals the pericyte and not epithelial origin of myofibroblasts in kidney fibrosis. Am J Pathol 176, 85 (January, 2010).
4. C. Hung et al., Role of lung pericytes and resident fibroblasts in the pathogenesis of pulmonary fibrosis. American journal of respiratory and critical care medicine 188, 820 (Oct. 1, 2013).
5. C. Goritz et al., A pericyte origin of spinal cord scar tissue. Science 333, 238 (Jul. 8, 2011).
6. S. Dulauroy, S. E. Di Carlo, F. Langa, G. Eberl, L. Peduto, Lineage tracing and genetic ablation of ADAM12(+) perivascular cells identify a major source of profibrotic cells during acute tissue injury. Nat Med, (Jul. 29, 2012).
7. R. Kramann, D P DiRocco, B. D. Humphreys, Understanding the origin, activation and regulation of matrix-producing myofibroblasts for treatment of fibrotic disease. The Journal of pathology 231, 273 (November, 2013).
8. V. S. Lebleu et al., Origin and function of myofibroblasts in kidney fibrosis. Nat Med, (Jun. 30, 2013).
9. M. Crisan et al., Perivascular multipotent progenitor cells in human organs. Annals of the New York Academy of Sciences 1176, 118 (September, 2009).
10. S. Mendez-Ferrer et al., Mesenchymal and haematopoietic stem cells form a unique bone marrow niche. Nature 466, 829 (Aug. 12, 2010).
11. S. J. Morrison, D. T. Scadden, The bone marrow niche for haematopoietic stem cells. Nature 505, 327 (Jan. 16, 2014).
12. H. Zhu et al., A protocol for isolation and culture of mesenchymal stem cells from mouse compact bone. Nature protocols 5, 550 (March, 2010).
13. H. Zhao et al., Secretion of shh by a neurovascular bundle niche supports mesenchymal stem cell homeostasis in the adult mouse incisor. Cell stem cell 14, 160 (Feb. 6, 2014).
14. S. L. Fabian et al., Hedgehog-Gli pathway activation during kidney fibrosis. Am J Pathol 180, 1441 (April, 2012).
15. R. Liao et al., Cardiac-specific overexpression of GLUT1 prevents the development of heart failure attributable to pressure overload in mice. Circulation 106, 2125 (Oct. 15, 2002).
16. R. Kramann, M. Tanaka, B. D. Humphreys, Fluorescence Microangiography for Quantitative Assessment of Peritubular Capillary Changes after AKI in Mice. J Am Soc Nephrol, (Mar. 20, 2014).

17. A. E. Simoes et al., Efficient recovery of proteins from multiple source samples after TRIzol((R)) or TRIzol((R)) LS RNA extraction and long-term storage. BMC genomics 14, 181 (2013).
18. Y. Zhang et al., Validation of the wall motion score and myocardial performance indexes as novel techniques to assess cardiac function in mice after myocardial infarction. American journal of physiology. Heart and circulatory physiology 292, H1187 (February, 2007).

Figure 1:
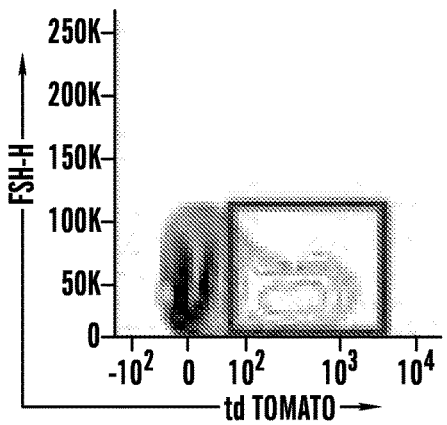
FIG. 1 shows data indicating that Gli1 expression defines a subset of PDGFRb+ kidney pericytes. Flow cytometric analysis of these cells from whole kidney documents an MSC phenotype: CD44+, CD29+, Sca1+, CD105+ and CD31−, CD34−, CD45−.
Figure 1:
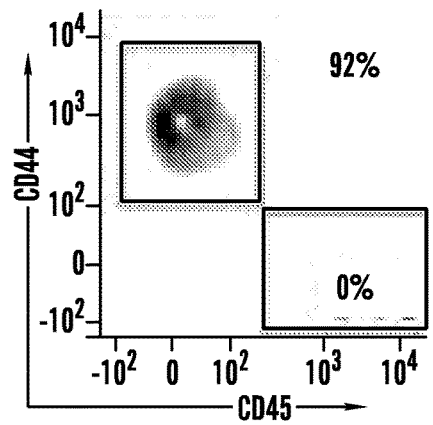
Figure 1:
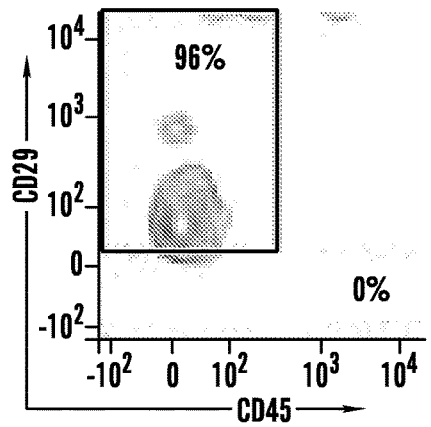
Figure 1:
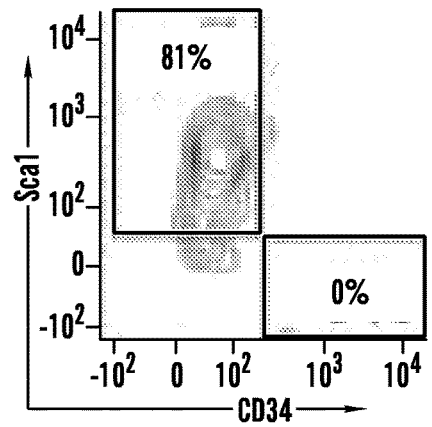
Figure 1:
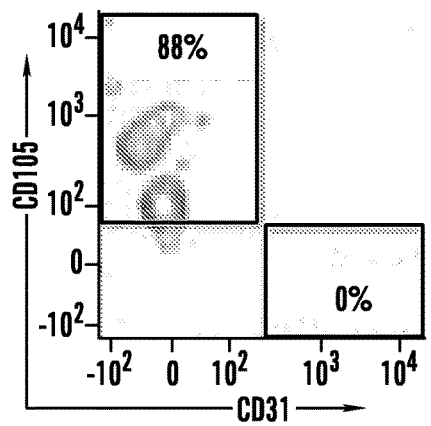
Figure 2:
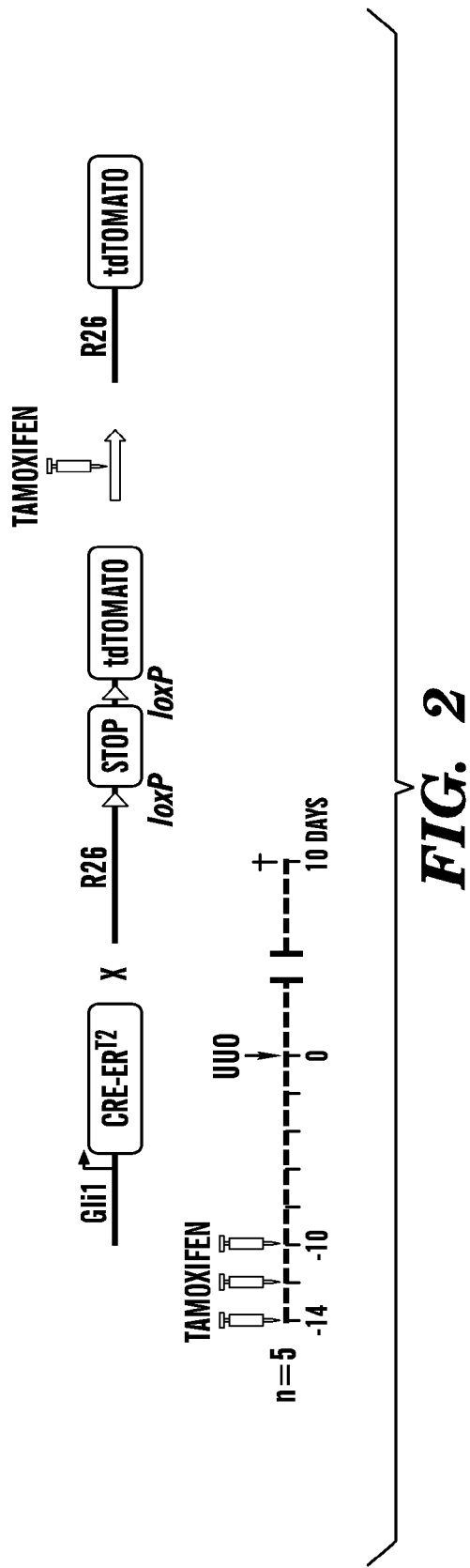
FIG. 2 show that Gli1+ cells dramatically expand and differentiate into myofibroblasts during unilateral ureteral obstruction (UUO). Genetic labeling scheme and UUO timeline. Gli1+ cells are labeled prior to UUO with three pulses of Tamoxifen in Gli1-CreERt2; R26tdTomato bigenic mice.

Example 3: Gli2 Regulates Myofibroblast Cell-Cycle Progression in Kidney Fibrosis and is a Novel Therapeutic Target Knockdown of Gli2 but not Gli1 Induces a G0/G1 Cell-Cycle Arrest In Vitro There are many examples of Hh-dependent regulation of cell proliferation in development and disease (10, 27, 34, 38-40). Gli2−/− skin transplants are characterized by growth arrest in hair follicle development while constitutively active Gli2 induces skin proliferation in Shh null mice, indicating that Gli2 is the effector of Hh-induced proliferation (39). Recent data from the inventors indicates that pharmacologic inhibition of Gli proteins reduces the self-renewal capacity of Gli1+ MSC-like myofibroblast precursors (7). To evaluate the role of Gli1 versus Gli2 on cell proliferation in vitro, the inventors performed siRNA knockdown experiments in the MSC-like cell line 10T1/2 (FIG. 19). Treatment with siRNA against Gli1 reduced mRNA and protein levels of Gli1 alone, while siRNA directed against Gli2 reduced both Gli1 and Gli2 expression, consistent with Gli1 as a downstream transcriptional target of Gli2 (FIGS. 21A2-21B). Flow cytometric analysis of cell-cycle distribution revealed that knockdown of Gli2 (or both Gli1 and Gli2) resulted in G0/G1 arrest with fewer cells in S and G2/M phases, whereas siRNA against Gli1 alone had no effect (FIG. 19C-19D). Knockdown of Gli2 or both Gli1 and Gli2 reduced levels of phosphorylated retinoblastoma (Ser780) with increased levels of the cyclin dependent kinase inhibitor p21, indicating that cells exited the cell cycle at the G1 restriction point (FIG. 1E).

Conditional Knockout of Gli2 or Overexpression of the Gli3 Repressor in Gli1+ Cells Reduces Kidney Fibrosis, but Knockout of Gli1 has No Effect Interstitial myofibroblasts and their perivascular precursors are the only cells in the mouse kidney that express Gli1 and Gli2 (7, 21) and it has been reported that knockout of Gli1 ameliorates kidney fibrosis in mice (22). Since Gli2 can compensate for Gli1 function in development, it was asked whether conditional knockout of Gli2 in Gli1+ cells would provide further additive protection against fibrosis compared to Gli1 knockout alone. To repress the entire Gli family, Gli1-CreERt2 mice were crossed against the R26-Gli3T strain, in which the Gli3 repressor is expressed from Rosa26 locus following Cre-mediated recombination (41). UUO experiments in Gli1-nLacZ and Gli2-nLacZ mice and co-staining for α-SMA and β-Galactosidase confirmed that expression of Gli1 and Gli2 is restricted to the myofibroblast lineage after kidney injury (data not shown).

Wildtype littermates, Gli1KO, conditional Gli2 KO, Gli1/2 KO or Gli3T mice were injected with tamoxifen as indicated, underwent unilateral ureteral obstruction (UUO) surgery and were sacrificed at day 10 following UUO (FIG. 20A).

As expected, Gli1 knockout mice lacked Gli1 expression (FIGS. 22B-22D). Gli2KO and Gli3T mice showed substantially reduced expression of Gli1, indicating that upstream Gli regulates basal Gli1 level. Gli2KO, Gli1/2KO and Gli3T mice exhibited significantly reduced expression of Gli2 compared to Gli1KO where Gli2 levels were unaffected (FIGS. 22C-22D). While Gli2 KO, Gli1/2KO and Gli3T mice showed reduced fibrosis severity, knockout of Gli1, surprisingly, had no appreciable effect when compared to wildtype littermates (FIGS. 22E-22H). These data indicate that knockout of Gli1 in the presence of Gli2 has no effect on kidney fibrosis, while inhibition of both Gli1 and Gli2 by Gli3T or conditional knockout of Gli2 (in haploinsufficient Gli1 or Gli1 knockout mice) reduced fibrosis severity. These observations are in line with previous reports that Gli1 knockout mice show no developmental phenotype in the presence of Gli2 (13, 15), indicating that Gli2 may rescue Gli1 functions, while Gli1 cannot rescue Gli2 functions in the absence of Gli2.

Without wishing to be bound by theory, a possible explanation for Gli1 knockout being not protective following UUO in our hands is the different background of the Gli1 CreERt2 mice compared to Gli1-nLacZ mice previously used to knockout Gli1 (22). The inventors therefore utilized Gli1-nLacZ mice to knockout Gli1, however again a difference in fibrosis severity could not be detected when comparing Gli1-nLacz+/+ mice to wildtype littermates.

Conditional Knockout of Gli2 or Expression of the Gli3 Repressor in Gli+ Cells Halts Kidney Fibrosis Progression by Inducing Myofibroblast-Specific Cell-Cycle Arrest.

Since the in vitro data indicated that Gli2 is required for cell-cycle progression in MSC-like cells, the inventors next asked whether Gli2 knockout or Gli3T expression reduces fibrosis severity by halting myofibroblast cell-cycle progression in vivo. Wildtype littermates, Gli1 KO, Gli2KO, Gli1/2KO and Gli3T mice received tamoxifen, underwent UUO surgery and were euthanized at day 3 following surgery. BrdU was administered 3 hours before sacrifice. The inventors next performed co-staining for BrdU (S-Phase) with phospho-histone H3 (p-H3, G2/M Phase) and α-SMA (myofibroblasts; data not shown). Quantification of stained tubular and interstitial α-SMA+ cells revealed a G0/G1 cell cycle arrest specifically in myofibroblasts (FIG. 21A). The cell-cycle distribution of tubular-epithelial cells was not affected (FIG. 21B), consistent recombination specifically in interstitial myofibroblasts and their Gli1+ precursors.

Protein analysis of whole kidney lysates showed increased levels of the cyclin dependent kinase inhibitor p21 and decreased levels of p-Rb following conditional knockout of Gli2 or expression of the Gli3 repressor (FIG. 21C). These data indicated that interstitial myofibroblasts left the cell-cycle at the G1 restriction point before the phosphorylation of retinoblastoma at Ser780 and consistent with the in vitro findings after siRNA mediated knockdown of Gli2.

The Novel Organic Arsenic Darinaparsin Reduces Gli1 and Gli2 Protein Levels and Induces a Cell-Cycle Arrest of MSC-Like Cells In Vitro.

The inventors were next interested in determining whether this Gli2-dependent pro-fibrotic pathway in kidney myofibroblasts could be targeted therapeutically. Arsenic trioxide (ATO) is used clinically to treat acute promyelocytic leukemia and was recently shown to antagonize both Gli1 and Gli2 (42, 43). It was therefore investigated if darinaparsin (S-dimethylarsino-glutathione), a novel arsenic-based drug with a favorable systemic toxicity profile (44) and currently undergoing clinical studies in hematologic malignancies and solid tumors, (36, 37) inhibits hedgehog effectors Gli1 and Gli2 and affects proliferation of MSC like cells in vitro. Indeed, darinaparsin was recently shown to modulate Gli protein levels in prostate cancer cell lines (45).

The MSC-like cell line 10T1/2 was treated with darinaparsin or vehicle and flow cytometric cell-cycle analysis revealed that darinaparsin (0.5 µM) induces a G0/G1 cell cycle arrest of 10T1/2 cells in vitro (FIG. 22A, 22B). The inventors next asked if darinaparsin treatment in vitro affects Gli protein levels and the regulator proteins of cell-cycle G1/S transition in a similar fashion as previous RNAi studies. Western blot analysis revealed that darinaparsin treatment reduced the protein levels of Gli1 and Gli2 with a subsequent upregulation of p21 and decreased levels of p-Rb (FIG. 4B). These data indicated together with previous RNAi results that the cell-cycle effect of low dose darinaparsin is related to its effect on Gli2 protein level.

Overexpression of Gli2 Drives Cell-Proliferation and Rescues the Cell-Cycle Inhibitory Effect of Darinaparsin.

The results identify Gli2 as a critical regulator of mesenchymal cell proliferation because reduction of Gli2 protein level by either RNAi, conditional knockout or darinaparsin treatment caused cell-cycle arrest. The inventors next investigated whether overexpression of Gli2 was sufficient to increase proliferation and rescue the inhibitory effect of darinaparsin. Gli2 was overexpressed in 10T1/2 cells by retroviral delivery, causing Hh pathway activation as reflected by increased mRNA expression of Gli1 and Ptch1 (FIGS. 24D-24G), as expected. Importantly, Gli2 overexpression increased cell proliferation and rescued the cell-cycle effect of darinaparsin treatment (FIGS. 24H-24I), confirming a central role for Gli2 in mediating these effects.

Coimmunoprecipitation Indicates Darinaparsin Binds Gli2 In Vitro.

Although these results implicate Gli2 as a target of darinaparsin, and arsenicals are known to antagonize Gli1 and Gli2, arsenic also inhibits a number of other pathways and could have been inhibiting Gli2 indirectly. On the other hand, arsenic has been proposed to bind to thiol groups on critical cysteine residues located in the Gli zinc finger domains (47), by extension of its known binding to zinc fingers of the promyelocytic leukemia protein (48). To test this hypothesis the inventors overexpressed myc-tagged Gli2 (pCS2-MT Gli2FL) (49) in human 293T cells. After 72 hours, cells were treated overnight with 0.5 µM darinaparsin or vehicle, and the cell-lysate was incubated with glutathione-s-transferase (GST) agarose beads. Since the arsenic in Darinaparsin (S-methylarsino-glutathione) is bound to glutathione moieties it was expected that GST would bind the glutathione, allowing pull-down of darinaparsin itself and of any protein bound to the arsenic. Indeed, using this strategy it was observed that GST beads pulled down Gli2 only in the presence of darinaparsin, but not in its absence, providing strong evidence that darinaparsin binds directly to Gli2 (FIG. 22J). While Western blot of the cell lysate before immunoprecipitation shows similar Gli2-levels (FIG. 22J, "input"), Gli2 is pulled down with the GST-beads only if the cells were treated with the GSH-moiety containing arsenic (FIG. 22J, "IP DAR"), and the lysate is depleted of Gli2 after incubation with and separation of the GST-beads in the presence of darinaparsin (FIG. 22J, "outflow"). Of note, darinaparsin treatment did not result in enrichment of significant levels of other nonspecific proteins as indicated by Ponceau staining of the membrane.

Darinaparsin Prevents the Increase of Gli1 and Gli2 Normally Observed During Fibrosis and Ameliorates Fibrosis Even when Administered After Injury.

Having established that darinaparsin directly binds to Gli2, it was next investigated whether it would reduce the expression of Gli1 and Gli2 in vivo and most importantly, reduce the severity of kidney fibrosis. Wildtype mice were treated daily with darinaparsin or vehicle starting 2 days prior to UUO surgery and sacrificed at day 10 (FIG. 23A). Western blot analysis revealed a significant reduction of endogenous Gli1 and Gli2 protein levels in the UUO kidneys of darinaparsin treated mice compared to the UUO kidneys of the control group (FIG. 23B). A similar experiment in LacZ reporter mice for Gli1 and Gli2 (Gli1-nLacZ, Gli2-nLacZ) demonstrated that darinaparsin treatment reduces the number of Gli expressing interstitial cells after UUO. Furthermore darinaparsin treatment resulted in reduced mRNA expression of Hh readouts Gli1 and Ptch1.

Strikingly, the severity of fibrosis was significantly reduced in the darinaparsin treatment group (FIGS. 23C-23F). To determine whether darinaparsin ameliorates fibrosis in a therapeutic rather than preventative dosing strategy, the inventors repeated the UUO experiment but started darinaparsin treatment two days after the ureteral ligation surgery. The inventors again observed substantial reductions in fibrotic readouts using this protocol (data not shown).

In order to test whether darinaparsin not only improves fibrosis but preserves kidney function in a therapeutic model, a severe bilateral ischemia-reperfusion injury (IRI) model was used that causes substantial fibrosis and CKD at four weeks as previously reported as an acute kidney injury (AKI) to CKD model (51). A total of 19 mice underwent surgery and were randomized at day 7 after the surgery to two groups with no difference in their day 1 and day 7 blood urea nitrogen (BUN) levels (FIGS. 25H-25I). After randomization mice were treated daily with darinaparsin or vehicle and sacrificed at day 28 (FIG. 23G). Mice in the treatment group showed reduced interstitial fibrosis and reduced expression of fibrotic readouts (FIGS. 23H-23I). Importantly, the anti-fibrotic effect of darinaparsin was accompanied by lower BUN levels at late timepoints after injury, when compared to the vehicle group (FIG. 23H).

Darinaparsin Induces Myofibroblast-Specific Cell Cycle Arrest In Vivo.

Since the previous results indicated that cell specific knockout of Gli2 led to myofibroblast-specific cell-cycle arrest, the inventors next sought to determine the effect of darinaparsin treatment on myofibroblast proliferation in vivo. C57Bl6 mice were injected with darinaparsin or vehicle starting 2 days prior to UUO surgery and sacrificed at day 3. BrdU was administered 3 hours before sacrifice. The inventors next performed the same co-staining experiments as in the in vivo knockout experiments with staining for BrdU (S-Phase), p-H3 (G2/M Phase) and α-SMA (myofibroblasts, FIG. 24A) and quantified stained tubular and interstitial α-SMA+ cells to calculate the cell-cycle stages for both cell-types (FIGS. 26B-26C).

Importantly, darinaparsin treatment resulted in a G0/G1 cell-cycle arrest of interstitial myofibroblasts (FIG. 24B) without altering the cell-cycle distribution of tubular-epithelial cells (FIG. 24C), indicating that myofibroblasts are uniquely sensitive to darinaparsin and consistent with the previous finding that myofibroblasts and their precursors are the only kidney cell type expressing Gli proteins during fibrosis (7, 21).

Western blot analysis of whole kidney lysates at day 10 after UUO revealed significantly increased expression of the cyclin dependent kinase inhibitor p21 in the darinaparsin treated UUO kidneys compared to the vehicle treated group (FIG. 24D). The upregulation of p21 was accompanied by reduced phosphorylated retinoblastoma protein (p-Rb, Ser780) (FIG. 24D, CLK kidneys S9) indicating that most myofibroblasts in darinaparsin-treated UUO kidneys exited the cell cycle at the G1 restriction point. These results are consistent with previous experiments with blockade of the hedgehog-pathway on the level of Gli through conditional knockout of Gli2 or expression of the Gli3 repressor indicating that the in vivo antifibrotic effect of darinaparsin is indeed mediated trough lowering Gli2 protein levels with a subsequent cell-cycle arrest of myofibroblasts.

Treatment with GANT61, a Specific Small-Molecule Gli Antagonist, Ameliorates Kidney Fibrosis Following Unilateral Ureteral Obstruction Surgery.

Collectively these results indicate that Gli2 is a novel therapeutic target in kidney fibrosis, however darinaparsin is an arsenical with an uncertain long term safety profile even though it has reduced toxicity when compared to ATO (44, 50). This could complicate efforts to develop darinaparsin as an anti-fibrotic treatment for patients with CKD. Therefore, the inventors investigated whether targeting of Gli proteins using the specific Gli antagonist 61 (GANT61) might inhibit fibrosis in a similar fashion as darinaparsin to ameliorate kidney fibrosis.

Mice underwent UUO surgery and were treated after surgery as indicated (FIG. 25). Scoring of trichrome stained sections revealed significantly reduced interstitial fibrosis (FIGS. 25B, 25C). Expression of fibrotic readouts Coiled, α-SMA and fibronectin were significantly reduced in UUO kidneys of GANT61 treated mice when compared to the UUO kidneys of the vehicle treated mice (FIGS. 25D-25I). Treatment with GANT61 resulted in significantly reduced Gli1 and Gli2 protein levels of UUO kidneys, accompanied by a reduced mRNA expression of hedgehog readouts Gli1 and Ptch1 (FIGS. 25G-25J) confirming its ability to antagonize Gli proteins in vivo.

Gli Expression is Increased in Human Kidney Fibrosis

Given the inventors' data on Gli inhibition as a novel antifibrotic therapy in mouse kidney fibrosis it was next asked whether the same pathway might be upregulated in human kidney fibrosis. Kidney specimens were freshly obtained from tumor nephrectomies of 10 patients and immediately processed for histology and RNA extraction. Fibrosis severity was scored in Trichrome stained sections by a trained kidney pathologist blinded to mRNA results and clinical details. The kidney specimen were stratified into a low grade fibrosis group (fibrosis grade ≤20%) and high grade fibrosis group (fibrosis grade ≥40%) (FIGS. 26A-26B). In line with the histologic scoring the inventors determined increased mRNA expression of fibrotic readouts collagen1α1, fibronectin and αSMA in the high grade fibrosis group (FIG. 26C). Importantly, it was determined that increased expression of Gli1, Gli2 and Ptch1 mRNA pointing towards Hh pathway activity with upregulation of Gli2 in human kidney fibrosis (FIG. 26D).

The inventors have recently demonstrated that Gli1+ perivascular cells are an important kidney myofibroblast progenitor population (7). The results described herein demonstrate that Gli2 plays a critical functional role in regulating the proliferation of these cells and represents a novel therapeutic target in renal fibrosis. Conditional knockout of Gli2 or overexpression of the Gli3 repressor in Gli1+ cells ameliorates kidney fibrosis by inducing a myofibroblast-specific cell-cycle arrest. The same effects are achieved by Gli2 inhibition via darinaparsin, which the inventors show directly binds Gli2. Notably, this drug inhibits myofibroblasts specifically and had no appreciable effect on tubular epithelium, consistent with the absence of active Hh-Gli signaling in tubule.

The absence of Gli1 had no effect on kidney fibrosis in contrast to the report of Ding et al. (22). The reason for this discrepancy is unclear but the inventors cannot completely rule out a contribution from differing mouse background. On the other hand, the results strongly implicate Gli2 over Gli1 as the critical mediator of pro-fibrotic signaling in kidney, and the findings were consistent across different mouse strains in vivo as well as in a cell-culture model. This conclusion confirms previous reports that Gli2 is the major transcriptional activator of Hh signaling, and is consistent with the observations that Gli1 is not required for development whereas Gli2 knockout mice die at birth (13, 15-17).

Arsenic trioxide (ATO) is an established therapy for acute promyelocytic leukemia and acts via degradation of the oncoprotein AML-RXRα (44). Darinaparsin does not act via AML-RXRα degradation, however, and ATO resistant myeloma cell-lines are susceptible to darinaparsin (44). These findings indicate that darinaparsin has a different mechanism of action than ATO. Darinaparsin was designed as a novel organic arsenic by conjugating dimethylarsenic to glutathione, shows a significantly lower systemic toxicity with a 50-fold higher tolerated maximum dose when compared to ATO (44, 52, 53). Tian et al. reported no significant side effect of darinaparsin on fast cycling cell populations as the bone marrow or intestine (44). Darinaparsin is currently being tested in phase 2 clinical trials for solid tumors and hematopoietic malignancies, however, its molecular mechanism of action has not been fully elucidated (52). It has been reported that ATO antagonizes both Gli1 and Gli2 (42, 43) and a very recent report also suggests that darinaparsin might reduce Gli2 protein levels in prostate tumor initiating cells (45).

The mechanism by which arsenicals inhibit Gli2 function is not defined. Without wishing to be bound by theory, the mechanism probably involves effects on protein stability and subcellular localization. Kim et al. analyzed the effect of arsenic trioxide (ATO) on Hh signaling based on malformations in developing embryos after treatment with arsenic compounds showing a typical Hh dependent pattern (42, 54-56). They reported that short term ATO reduces ciliary accumulation of Gli2 leading to Hh pathway inhibition and long term ATO treatment reduced steady-state levels of Gli2, indicating a direct affect on Gli2 protein stability (42). This is in line with the inventors' observation that darinaparsin treatment reduces Gli2 protein levels in whole UUO kidney lysates and in 10T1/2 cells, with subsequent reduction of downstream Gli1 expression. It was demonstrated that darinaparsin directly binds to Gli2 and that Gli2 overexpression can rescue the cell cycle effect of darinaparsin in vitro. Importantly, these data indicate that darinaparsin treatment mimics the cell-cycle effect of RNAi against Gli2 in vitro or conditional Gli2 knockout in vivo and induces a myofibroblasts specific cell cycle arrest with upregulation of p21 and reduced pRb. The cell-restricted expression of Gli1 and Gli2 in kidney myofibroblasts and their precursors can explain the specific effect of darinaparsin on kidney myofibroblasts while the inventors did not observe cell-cycle alterations in tubular epithelial cells by darinaparsin treatment.

Hh signaling controls proliferation of diverse cell types during embryogenesis (57, 58), it regulates proliferation of cancer cells (59-61) and mounting evidence implicates Hh-Gli signaling in cell cycle progression at the restriction point. In Drosophila Hh signaling induces expression of Cyclin D and Cyclin E, both inhibitors of Rb (62). Nagao et al. reported that Gli2 knockdown prevented human osteosarcoma growth by inducing a G1 cell-cycle arrest via upregulation of p21 with subsequent reduction of Rb phosphorylation (63). Similar effects involving a G0/G1 arrest by p21 upregulation and reduced levels of phosphorylated Rb have been reported by knockdown of Gli2 in human vascular smooth muscle cells (27), human hepatocellular carcinoma cells (64) and human MSC (65). All of these findings support the inventors' observation that lowering Gli2 protein level by darinaparsin treatment or siRNA induces a cell-cycle arrest of myofibroblasts at the restriction point by upregulation of p21/Cip1 with subsequent inhibition of Rb phosphorylation whereas overexpression of Gli2 increases proliferation.

GANT61 was found in a compound screen as a direct Gli antagonist with selectivity for the Hh pathway (66). It has been reported that GANT61 induced a G0/G1 arrest with upregulation of p21 in human colon cancer cells (67). Importantly, in bleomycin induced lung fibrosis GANT61 decreased fibrosis severity, while inhibition of smoothened via GDC-0449 did not show this effect (68). The ability of Gli inhibitor that is structurally distinct from darinaparsin to ameliorate fibrosis strongly supports the central role of Gli in kidney fibrosis and as a novel therapeutic target in CKD.

Thus, Gli2 regulates kidney myofibroblast proliferation and is a novel therapeutic target. Gli2 inhibition, via darinaparsin, reduces fibrosis in two kidney fibrosis models even when administered after the onset of fibrosis by inducing a myofibroblast specific cell-cycle arrest. Furthermore, antagonizing Gli proteins with GANT61 also ameliorated renal fibrosis confirming the relevance of Gli proteins in kidney fibrosis and providing a more specific compound with potentially fewer side effects than arsenics. Importantly, these data also indicate that this pathway is upregulated in human kidney fibrosis, providing strong support for future investigation of Gli inhibition to slow CKD progression in humans.

Methods

Animal Experiments:

All mouse experiments were performed according to the animal experimental guidelines issued by the Animal Care and Use Committee at Harvard University. Wild type mice were 8-10 weeks old males C57Bl/6J from Charles River Laboratories (Wilmington, Mass.).

Gli1CreERt2 (i.e., Gli1tm3(re/ERT2)Alj/J, JAX Stock #007913), Gli2 floxed (i.e., Gli2tm6ALj/J, JAX Stock #007926), Gli3T (i.e., Gt(ROSA)26Sortm3(Gli3)Amc/J JAX Stock #013124), Gli1-nLacZ (JAX Stock 008211), Gli2-nLacZ (JAX stock 0007922) were purchased from Jackson Laboratories (Bar Harbor, Me.).

Gli1-KO mice were generated by generating homozygous Gli1 CreERt2 mice or by breeding heterozygote Gli1-nLacZ (12951/SvImJ background) that harbor a β-galactosidase knock-in at the transcriptional start site that abolishes Gli1 gene function. (15) Offspring were genotyped by PCR according to the protocol from the Jackson laboratory. Wild type littermates were used as controls in the conditional knockout experiments experiment and heterozygote littermates were used as controls for the quantification of LacZ positive cells. For the conditional knockout experiments all mice received tamoxifen (CAYMAN CHEMICALS in corn oil 3% ethanol, 0.4 mg/kg bodyweight p.o.) as indicated.

All mice underwent UUO surgery at 8-10 weeks as previously described. (21) Briefly, after flank incision the left ureter was tied off at the level of the lower pole with two 4.0 silk ties. Mice were sacrificed at day 10 after surgery. For the quantification of proliferation mice were injected with Bromodeoxyuridine (BrdU; Sigma, 100 mg/kg bodyweight in normal saline intraperitoneally) on day 3 after surgery and sacrificed 3 hours after BrdU injection. LacZ positive cells in Gli1-nLacZ+/+ vs Gli1-n-LacZ+/− mice were quantitated at day 7 after UUO surgery. For the bilatereal ischemia re-perfusion injury (IRI) experiments surgery were performed as previously described. (69) Briefly, mice were anesthetized with pentobarbital sodium (60 mg/kg body weight, intraperitoneally), kidneys were exposed through flank incisions and mice were subjected to ischemia by clamping the renal pedicle with nontraumatic microaneurysm clamps (Roboz, Rockville, Md.) for 26 min. Body temperatures were controlled at 36.5° C.-37.5° C. throughout the procedure. Mice were bled 7 days prior to surgery, at day 1, 7, 14, 21 and 28 after surgery by tail vein bleeding. BUN was measured using the Infinity Urea assay (Thermo Scientific) according to the manufacturer instructions.

Darinaparsin Experiments:

Darinaparsin (Zio-101, Ziopharm Oncology Inc., Cambridge, Mass.) was prepared freshly before treatment of cells or animals by dissolving in normal saline (vehicle). For animal experiments a 5 mg/ml stock solution was prepared and animals were given daily 50 mg/kg body weight darinaparsin or vehicle per intraperitoneal injection. In the UUO experiments, mice were randomly assigned to the darinaparsin or vehicle group and treated starting 2 days before surgery (Experiment 1, FIG. 19) or starting 2 days after surgery (Experiment 2, data not shown). The last dose was given 4 hours before sacrifice. In the IRI experiment mice were treated daily starting at day 7 after surgery until they were sacrificed at day 28 after surgery. For the cell-culture experiments a 1 mM stock solution was sterile filtered and a final concentration of 0.5-3 μM was used in the cell-culture medium every 24 h versus normal saline (vehicle).

GANT61 Experiments:

Gant61 (CAYMAN CHEMICALS #13841) was dissolved in ethanol and stored at −80° C. The ethanol solution was further diluted in corn-oil (1:4) immediately before subcutaneous injection (50 mg/kg bodyweight) at day 1, 2, 3, 5, 7 and 9 after UUO surgery. Preparation of Gant61 in this ethanol/oil solution and delivery via subcutaneous injection in mice has been described previously by Lauth et al. (70) Control mice were injected with the vehicle (ethanol/corn oil 1:4) at the same time-points.

Tissue Preparation and Histology:

Mice were anesthetized with isofluorane and subsequently perfused via the left ventricle with 4° C. PBS for 1 minute. For histological analyses tissue sections were fixed in 10% formaldehyde for 1 h, paraffin embedded and cut with a rotating microtome at 3 μm thickness and stained according to routine histology protocols. For immunofluorescence studies kidneys were fixed in 4% paraformaldehyde on ice for 1 hour, then incubated in 30% sucrose in PBS at 4° C. overnight. OCT-embedded (SAKURA FINETEK) kidneys were cryosectioned into 7 μm sections and mounted on Superfrost slides (FISHER SCIENTIFIC). Sections were washed in 1×PBS, blocked in 10% normal goat serum (VECTOR LABS) and incubated with primary antibodies specific BrdU (1:100, ABCAM # ab6326), phospho-Histone H3 (1:100, SANTA CRUZ BIOTECHNOLOGIES, #SC-8656-R), alpha SMA (1:200, Sigma, Cat No. A2547), alpha SMA-Cy3 (1:200, Sigma, # C6198) Secondary antibodies were FITC-, Cy3, or Cy5-conjugated (JACKSON IMMUNORESEARCH). Sections were then stained with DAPI and mounted in Prolong Gold (LIFE TECHNOLOGIES).

Quantification of BrdU+, phospho-Histone H3+ (p-H3+) tubular-epithelial cells and myofibroblasts (α-SMA+) was performed in 6 mice of each group. Pictures (400×, n=7/kidney) were taken randomly across the cortex of the UUO and CLK kidneys, positive cells were counted manually. Cell-cycle stages of myofibroblasts were calculated as follows: G0/G1=all α-SMA+ cells-BrdU+/α-SMA+ cells-p-H3+/α-SMA+ cells; S=BrDU+/α-SMA+ cells; G2/M=p-

H3+/α-SMA+ cells, cell cycle stages of tubular cells were calculated as follows: G0/G1=all tubular cells-BrDU+ tubular cells-p-H3+ tubular cells; S=BrDU+ tubular cells; G2/M=p-H3+ tubular cells. Quantification of α-SMA positive surface area was performed by taking random cortical pictures (200×, n=7/kidney) in UUO and CLK kidneys of each mouse (n=7 vehicle vs n=9 darinaparsin) using the number of stained pixels per total pixels in ADOBE PHOTOSHOP CS5 (ADOBE SYSTEMS, Inc., San Jose, Calif.). All images were obtained by confocal (NIKON C1 eclipse, NIKON, Melville, N.Y.) or standard microscopy (NIKON eclipse 90i).

Fibrosis severity was scored at 400× magnification using a counting grid with 117 intersections. The number of grid intersections overlying trichrome positive (blue) interstitial area was counted and expressed as a percentage of all grid intersections. For this calculation intersections that were in tubular lumen and glomeruli were substracted from the total number of grid intersections.

To identify LacZ activity in kidney sections, PFA fixed frozen sections were incubated in standard 5-bromo-4-chloro-3-indolyl-β-d-galactoside (X-gal) for 48 hours, counterstained with nuclear fast red and mounted.

Cell Culture Experiments:

All cell-lines used within this study were freshly ordered from ATCC and routinely checked for mycoplasma contamination in the inventors' laboratory. 10T1/2 cells (ATCC) and cultured in Basal Medium Eagle (BME, GIBCO; LIFE TECHNOLOGIES) supplemented with 10% fetal bovine serum (FBS), penicillin and streptomycin and 2 mmol/L glutamine (GIBCO). Sonic hedgehog conditioned media was produced from supernatant of confluent Cos7 cells stably transfected with pcDNA3-N-Shh or pcDNA3 control plasmid. For Western blot experiments cells were grown on 10 cm dishes, serum starved in 0.5% FBS for 12 hours and then incubated with darinaparsin (0.5 μM) or vehicle with either Shh preconditioned medium or Cos7 control media (5× i.e., 2 ml preconditioned media in 8 ml BMW 0.5% FBS) for 72 hours.

For cell-cycle analysis cells were grown on 6 well plated until 50% confluency, serum starved in 0.5% FBS for 4 h to synchronize the cell-cycle and then cultured for 48 hours in 10% FBS medium together with 0.5-3 μM darinaparsin or normal saline (vehicle). Before fixation cells were incubated for 75 minutes in 10 μM BrDU and stained according to the BD APC BrdU Flow Kit (BD BIOSCIENCE #552598). Cells were analyzed by flow cytometry (FACS Canto II, BD BIOSCIENCES) within 1 hour after staining, and data were analyzed by using Flow Jo software (Version 7.5, TREE STAR Inc).

SiRNA Knockdown Experiments:

For siRNA experiments cells were transfected with siRNA against Gli1 (LIFE SCIENCES, siRNA ID: s66723, Sequence 5'3' Sense: GCAGGUCUCCUAUCCUGAUtt (SEQ ID NO: 11), Antisense: nAUCAGGAUAGGAGAC-CUGCtg (SEQ ID NO: 12)), Gli2 (LIFE SCIENCES, siRNA ID: s66726, Sequence 5'3' Sense: GGAAAACUU-CAACAAUACAtt (SEQ ID NO: 13), Antisense: UGUAUUGUUGAAGUUU UCCag (SEQ ID NO: 14)), and both Gli1 and Gli2, scrambled siRNA was used as a negative control (LIFE TECHNOLOGIES, #AM4611) and Cy3 labeled siRNA against GAPDH (LIFE TECHNOLOGIES, #AM4649) was used as a positive control for the transfection. Transfection was performed with a final concentration of 5 nM of each siRNA according to the manufacturer instructions using LIPOFECTAMINE RNAiMAX transfection reagent (LIFE TECHNOLOGIES, #3778075). 72 hours after transfection cells were harvested for RNA or protein isolation. For cell cycle analysis cells were split 48 h after transfection at a seeding density of 50%, 24 h after the seeding cells were incubated for 75 min with 10 μM BrDU and subjected to cell-cycle analysis as described above.

Overexpression of Gli2 by Retroviral Delivery:

The RSF91.IRES.EGFP retroviral vector was a kind gift of Dr. Axel Schambach and Dr. Christopher Baum (both Hannover Medical School, Hannover, Germany). The vector was modified with a multiple cloning site containing the SbfI and MluI restriction enzyme sites. The full length Gli2 cDNA was kindly provided by Dr. Hiroshi Sasaki (Riken database RDB #08065, Gene ID 14633). (71) The Gli2 cDNA was PCR amplified using PHUSION Polymerase (New England Biolabs, #m0530) and a N-terminal HA-tag, a 5' SbfI, and 3' MluI site were added and the cDNA was inserted into the multiple cloning site. Ecotropic retroviral particles were produced by calcium phosphate based transient co-transfection of HEK293T cells with the retroviral constructs and packaging plasmid. Viral supernatants were collected at 36-48 h post transfection and 0.22 uM filtered. Cell transduction was performed by incubating the cells with serial dilutions of the retroviral supernatants in the presence of 4 ug/ml Polybrene (SIGMA-ALDRICH, #107689). Cell-cycle flow-cytometric analysis was performed using 4',6-diamidino-2-phenylindole (DAPI) instead of 7AAD for detection of DNA content due to the viral GFP expression.

Gli2 Darinaparsin Binding Assay:

Human 293T/17 (HEK 293T/17, freshly ordered from ATCC) were grown in a 10 cm cell-culture dish until 80% confluent and transfected with pCS2-MT Gli2 FL kindly provided by Dr. Roessler (49) (ADDGENE Plasmid 17648: pCS2-MT GLI2 FL) using Lipofectamine 2000 (LIFE TECHNOLOGIES) according to the manufacturer instructions. 72 hours after transfection the cells were treated with 0.5 μM darinaparsin or vehicle in DMEM 10% FBS for 12 hours, thereafter cells were resuspended in cold (4° C.) PBS and washed twice with PBS. After centrifugation (1500 rpm, 5 minutes) 1 ml of IP-Lysis Buffer (THERMO SCIENTIFIC)+proteinase inhibtior (ROCHE, #1183617000T) was added to the cell pellet and the suspension was homogenized using an insulin syringe. After centrifugation of the protein-solution (15 min, 12000 rpm) the supernatant was transferred into a fresh tube, an aliquot of 100 μl was taken as input control (FIG. 24) and the solution was incubated with 50 μl GST-Agarose beads (PIERCE GST Agarose #20211, THERMO SCIENTIFIC) for 4 hours on a rotator at 4° C. Thereafter the bead-protein solution was centrifuged (5000 rpm, 3 min) and the supernatant was taken as outflow control (FIG. 24), the agarose beads were washed three times by adding 1 ml of the above mentioned IP-Lysis buffer containing proteinase inhibitors followed by vortexing and centrifugation (5000 rpm, 3 min), the supernatant after each centrifugation was discarded. After 3 washes, the GST beads were cooked at 96° C. for 7 minutes in 100 μl Laemmli buffer (BIO-RAD). All protein samples (input, outflow and the final GST bead purification solution) were analysed by western blot with an antibody against c-myc (mouse monoclonal, 9E 10, DSHB, Iowa) the membrane was stained with Ponceau-S (SIGMA) to show specificity (FIG. 6H).

Real Time PCR Experiments:

Kidney tissue or cell-pellets were harvested and immediately snap frozen in liquid nitrogen. RNA was extracted according to the manufacturer instructions using the RNeasy Mini Kit (QIAGEN) and 600 ng of total RNA was reverse transcribed with iScript (BIORAD). Quantitative polymerase chain reactions were carried out with iQ-SYBR Green supermix (BIORAD) and the BIORAD CFX96 Real Time System with the C1000 Touch Thermal Cycler. Cycling conditions were 95° C. for 3 minutes then 40 cycles of 95° C. for 15 seconds and 60° C. for 1 minute, followed by one cycle of 95° C. for 10 seconds. Glyceraldehyde-3-phosphate dehydrogenase (GAPDH) was used as a housekeeping gene. Data was analyzed using the 2-ΔΔct method.

Western Blot:

Kidney tissue was snap frozen in liquid nitrogen and stored at −80° C. immediately after mice were killed. Tissue samples were homogenized in lysis buffer containing 10 mM HEPES, pH 7.4, 0.32M sucrose, 2 mM EDTA, 1 mM DTT, 1 mM PMSF and 1 protease inhibitor tablet per 10 ml of lysis buffer (ROCHE Cat. No. 11836153001). Samples were sonicated and protein concentration was determined by the Bradford Assay using BIO-RAD Protein Assay Dye (BIORAD, Cat. No. 500-0006). 10-40 μg of protein from lysates was loaded on a 7.5 or 10% polyacrylamide gel and separated by SDS electrophoresis. Proteins were transferred to a IMMOBILON membrane (MILLIPORE) blocked in 5% milk in PBST, probed overnight at 4° C. with the primary antibodies: mouse anti-αSMA at 1:4000 (SIGMA, Cat. #A2547), rabbit anti-fibronectin at 1:4000 (ABCAM, #ab23750), rabbit anti-p21 at 1:200 (SANTA CRUZ BIO-TECHNOLOGIES, #sc-471), rabbit anti-phospho-retinoblastoma(72) at 1:1000 (CELL SIGNALING #9307S, Ser780), rat anti-Gli1 at 1:1000 (R&D Systems #MAB3324), goat anti-Gli2 at 1:500 (R&D Systems #AF3635), rabbit anti-Cyclin Eat 1:200 (SANTA CRUZ #sc-481), rabbit anti-Cyclin A at 1:200 (SANTA CRUZ BIOTECHNOLOGIES #sc-751), rabbit anti-HA-Tag at 1:5000 (CELL SIGNALING #3724), mouse anti-c-myc (DSHB, Iowa, 9E 10) and rabbit anti-GAPDH at 1:4000 (BETHYL LABORATORIES, #A300-641A). Following incubation with primary antibody blots were washed probed with respective horseradish-peroxidase conjugated secondary antibodies at 1:5000 (DAKO, Cat. No. P0447, P0448, P0450) for 1 hour at room temperature and then visualized using the Western Lightning ECL kit from PERKINELMER (#NEL100001EA). Quantification of western bands was performed using ImageJ (NIH).

Human Kidney Specimens:

Human kidney specimens from 10 patients undergoing partial or total nephrectomy procedures for urologic indications. Nephrectomy specimens were immediately placed on ice and within 15 minutes of surgical removal, three 5 mm cubes of tissue were cut from portions of non-neoplastic tissue and placed into three separate containers with specific preservatives (neutral buffered formalin, 4% paraformaldehyde in phosphate-buffered saline, or RNA-Later). Trichrome-stained slides from formalin-preserved tissue were examined by a trained senior pathologist for semi-quantitative assessment of cortical tubulointerstitial fibrosis. The study was approved by the Institutional Review Board of Brigham and Women's Hospital and all patients provided written informed consent.

Statistical Analysis:

All results are reported as mean±SEM. Comparison of two groups was performed using unpaired t-test or Mann-Whitney U test where appropriate. For multiple group comparison analysis of variance with posthoc Bonferroni correction was applied. Statistical analyses were performed using GraphPad Prism 5.0c (GRAPHPAD Software Inc., San Diego, Calif.). A p value of less than 0.05 was considered significant.

REFERENCES FOR EXAMPLE 3

1. McCullough K, Sharma P, Ali T, Khan I, Smith W C, MacLeod A, and Black C. Measuring the population burden of chronic kidney disease: a systematic literature review of the estimated prevalence of impaired kidney function. Nephrol Dial Transplant. 2012; 27(5):1812-21.
2. McClellan W M, and Plantinga L C. A public health perspective on CKD and obesity. Nephrol Dial Transplant. 2013; 28 Suppl 4(iv37-42.
3. US Renal Data System: USRDS 2013 Annual Data Report: Atlas of Chronic Kidney Disease and End-Stage Renal Disease in the United States, Bethesda, Md., National Institutes of Health, National Institute of Diabetes and Digestive and Kidney Disease, 2013.
4. US Renal Data System: USRDS 2011 Annual Data Report: Atlas of Chronic Kidney Disease and End-Stage Renal Disease in the United States, Bethesda, Md., National Institutes of Health, National Institute of Diabetes and Digestive and Kidney Disease, 2011.
5. Kramann R, Dirocco D P, Maarouf O H, and Humphreys B D. Matrix Producing Cells in Chronic Kidney Disease: Origin, Regulation, and Activation. Current pathobiology reports. 2013; 1(4).
6. Kramann R, DiRocco D P, and Humphreys B D. Understanding the origin, activation and regulation of matrix-producing myofibroblasts for treatment of fibrotic disease. The Journal of pathology. 2013; 231(3):273-89.
7. Kramann R, Schneider R K, DiRocco D P, Machado F, Fleig S, Bondzie P A, Henderson J M, Ebert B L, and Humphreys B D. Perivascular Gli1 Progenitors Are Key Contributors to Injury-Induced Organ Fibrosis. Cell stem cell. 2014.
8. Hui C C, and Angers S. Gli proteins in development and disease. Annual review of cell and developmental biology. 2011; 27(513-37.
9. Briscoe J, and Therond P P. The mechanisms of Hedgehog signalling and its roles in development and disease. Nat Rev Mol Cell Biol. 2013.
10. Robbins D J, Fei D L, and Riobo N A. The Hedgehog signal transduction network. Science signaling. 2012; 5(246):re6.
11. Matise M P, Epstein D J, Park H L, Platt K A, and Joyner A L. Gli2 is required for induction of floor plate and adjacent cells, but not most ventral neurons in the mouse central nervous system. Development. 1998; 125(15): 2759-70.
12. Litingtung Y, and Chiang C. Specification of ventral neuron types is mediated by an antagonistic interaction between Shh and Gli3. Nature neuroscience. 2000; 3(10): 979-85.
13. Park H L, Bai C, Platt K A, Matise M P, Beeghly A, Hui C C, Nakashima M, and Joyner A L. Mouse Gli1 mutants are viable but have defects in SHH signaling in combination with a Gli2 mutation. Development. 2000; 127(8): 1593-605.
14. Humke E W, Dorn K V, Milenkovic L, Scott M P, and Rohatgi R. The output of Hedgehog signaling is controlled by the dynamic association between Suppressor of Fused and the Gli proteins. Genes Dev. 2010; 24(7):670-82.
15. Bai C B, Auerbach W, Lee J S, Stephen D, and Joyner A L. Gli2, but not Gli1, is required for initial Shh signaling and ectopic activation of the Shh pathway. Development. 2002; 129(20):4753-61.
16. Ding Q, Motoyama J, Gasca S, Mo R, Sasaki H, Rossant J, and Hui C C. Diminished Sonic hedgehog signaling and lack of floor plate differentiation in Gli2 mutant mice. Development. 1998; 125(14):2533-43.
17. Mo R, Freer A M, Zinyk D L, Crackower M A, Michaud J, Heng H H, Chik K W, Shi X M, Tsui L C, Cheng S H, et al. Specific and redundant functions of Gli2 and Gli3 zinc finger genes in skeletal patterning and development. Development. 1997; 124(1):113-23.

18. Bai C B, and Joyner A L. Gli1 can rescue the in vivo function of Gli2. Development. 2001; 128(24):5161-72.
19. Yu J, Carroll T J, and McMahon A P. Sonic hedgehog regulates proliferation and differentiation of mesenchymal cells in the mouse metanephric kidney. Development. 2002; 129(22):5301-12.
20. Aberger F, and Ruiz I A A. Context-dependent signal integration by the GLI code: The oncogenic load, pathways, modifiers and implications for cancer therapy. Seminars in cell & developmental biology. 2014.
21. Fabian S L, Penchev R R, St-Jacques B, Rao A N, Sipila P, West K A, McMahon A P, and Humphreys B D. Hedgehog-Gli pathway activation during kidney fibrosis. Am J Pathol. 2012; 180(4):1441-53.
22. Ding H, Zhou D, Hao S, Zhou L, He W, Nie J, Hou F F, and Liu Y. Sonic hedgehog signaling mediates epithelial-mesenchymal communication and promotes renal fibrosis. J Am Soc Nephrol. 2012; 23(5):801-13.
23. Zhou D, Li Y, Zhou L, Tan R J, Xiao L, Liang M, Hou F F, and Liu Y. Sonic Hedgehog Is a Novel Tubule-Derived Growth Factor for Interstitial Fibroblasts after Kidney Injury. J Am Soc Nephrol. 2014.
24. Dennler S, Andre J, Alexaki I, Li A, Magnaldo T, ten Dijke P, Wang X J, Verrecchia F, and Mauviel A. Induction of sonic hedgehog mediators by transforming growth factor-beta: Smad3-dependent activation of Gli2 and Gli1 expression in vitro and in vivo. Cancer research. 2007; 67(14):6981-6.
25. Dennler S, Andre J, Verrecchia F, and Mauviel A. Cloning of the human GLI2 Promoter: transcriptional activation by transforming growth factor-beta via SMAD3/beta-catenin cooperation. J Biol Chem. 2009; 284(46):31523-31.
26. Xie J, Aszterbaum M, Zhang X, Bonifas J M, Zachary C, Epstein E, and McCormick F. A role of PDGFRalpha in basal cell carcinoma proliferation. Proc Natl Acad Sci USA. 2001; 98(16):9255-9.
27. Li F, Duman-Scheel M, Yang D, Du W, Zhang J, Zhao C, Qin L, and Xin S. Sonic hedgehog signaling induces vascular smooth muscle cell proliferation via induction of the G1 cyclin-retinoblastoma axis. Arterioscler Thromb Vasc Biol. 2010; 30(9):1787-94.
28. Bigelow R L, Jen E Y, Delehedde M, Chari N S, and McDonnell T J. Sonic hedgehog induces epidermal growth factor dependent matrix infiltration in HaCaT keratinocytes. The Journal of investigative dermatology. 2005; 124(2):457-65.
29. Riobo N A, Lu K, Ai X, Haines G M, and Emerson C P, Jr. Phosphoinositide 3-kinase and Ala are essential for Sonic Hedgehog signaling. Proc Natl Acad Sci USA. 2006; 103(12):4505-10.
30. Ji Z, Mei F C, Xie J, and Cheng X. Oncogenic KRAS activates hedgehog signaling pathway in pancreatic cancer cells. J Biol Chem. 2007; 282(19):14048-55.
31. Schnidar H, Eberl M, Klingler S, Mangelberger D, Kasper M, Hauser-Kronberger C, Regl G, Kroismayr R, Moriggl R, Sibilia M, et al. Epidermal growth factor receptor signaling synergizes with Hedgehog/GLI in oncogenic transformation via activation of the MEK/ERK/JUN pathway. Cancer research. 2009; 69(4):1284-92.
32. Stecca B, Mas C, Clement V, Zbinden M, Correa R, Piguet V, Beermann F, and Ruiz I A A. Melanomas require HEDGEHOG-GLI signaling regulated by interactions between GUI and the RAS-MEK/AKT pathways. Proc Natl Acad Sci USA. 2007; 104(14):5895-900.
33. Pasca di Magliano M, Sekine S, Ermilov A, Ferris J, Dlugosz A A, and Hebrok M. Hedgehog/Ras interactions regulate early stages of pancreatic cancer. Genes Dev. 2006; 20(22):3161-73.
34. Wallace V A. Purkinje-cell-derived Sonic hedgehog regulates granule neuron precursor cell proliferation in the developing mouse cerebellum. Current biology: CB. 1999; 9(8):445-8.
35. Dahmane N, and Ruiz i Altaba A. Sonic hedgehog regulates the growth and patterning of the cerebellum. Development. 1999; 126(14):3089-100.
36. Mann K K, Wallner B, Lossos I S, and Miller W H, Jr. Darinaparsin: a novel organic arsenical with promising anticancer activity. Expert opinion on investigational drugs. 2009; 18(11):1727-34.
37. Tsimberidou A M, Camacho L H, Verstovsek S, Ng C, Hong D S, Uehara C K, Gutierrez C, Daring S, Stevens J, Komarnitsky P B, et al. A phase I clinical trial of darinaparsin in patients with refractory solid tumors. Clinical cancer research: an official journal of the American Association for Cancer Research. 2009; 15(14):4769-76.
38. Izzi L, Levesque M, Morin S, Laniel D, Wilkes B C, Mille F, Krauss R S, McMahon A P, Allen B L, and Charron F. Boc and Gas1 each form distinct Shh receptor complexes with Ptch1 and are required for Shh-mediated cell proliferation. Dev Cell. 2011; 20(6):788-801.
39. Mill P, Mo R, Fu H, Grachtchouk M, Kim P C, Dlugosz A A, and Hui C C. Sonic hedgehog-dependent activation of Gli2 is essential for embryonic hair follicle development. Genes Dev. 2003; 17(2):282-94.
40. Li Y, Zhang H, Choi S C, Litingtung Y, and Chiang C. Sonic hedgehog signaling regulates Gli3 processing, mesenchymal proliferation, and differentiation during mouse lung organogenesis. Dev Biol. 2004; 270(1):214-31.
41. Vokes S A, Ji H, Wong W H, and McMahon A P. A genome-scale analysis of the cis-regulatory circuitry underlying sonic hedgehog-mediated patterning of the mammalian limb. Genes Dev. 2008; 22(19):2651-63.
42. Kim J, Lee J J, Kim J, Gardner D, and Beachy P A. Arsenic antagonizes the Hedgehog pathway by preventing ciliary accumulation and reducing stability of the Gli2 transcriptional effector. Proc Natl Acad Sci USA. 2010; 107(30):13432-7.
43. Beauchamp E M, Ringer L, Bulut G, Sajwan K P, Hall M D, Lee Y C, Peaceman D, Ozdemirli M, Rodriguez O, Macdonald T J, et al. Arsenic trioxide inhibits human cancer cell growth and tumor development in mice by blocking Hedgehog/GLI pathway. J Clin Invest. 2011; 121(1):148-60.
44. Tian J, Zhao H, Nolley R, Reese S W, Young S R, Li X, Peehl D M, and Knox S J. Darinaparsin: solid tumor hypoxic cytotoxin and radiosensitizer. Clinical cancer research: an official journal of the American Association for Cancer Research. 2012; 18(12):3366-76.
45. Bansal N, Johnson Farley N, Wu L, Lewis J, Youssoufian H, and Bertino J R. Darinaparsin inhibits prostate tumor initiating cells and Du 145 xenografts and is an inhibitor of hedgehog signaling. Molecular cancer therapeutics. 2014.
46. Mason T A, Kolobova E, Liu J, Roland J T, Chiang C, and Goldenring J R. Darinaparsin is a multivalent chemotherapeutic which induces incomplete stress response with disruption of microtubules and Shh signaling. PLoS One. 2011; 6(11):e27699.
47. Beauchamp E M, and Uren A. A new era for an ancient drug: arsenic trioxide and Hedgehog signaling. Vitamins and hormones. 2012; 88(333-54.

48. Zhang X W, Yan X J, Zhou Z R, Yang F F, Wu Z Y, Sun H B, Liang W X, Song A X, Lallemand-Breitenbach V, Jeanne M, et al. Arsenic trioxide controls the fate of the PML-RARalpha oncoprotein by directly binding PML. Science. 2010; 328(5975):240-3.
49. Roessler E, Ermilov A N, Grange D K, Wang A, Grachtchouk M, Dlugosz A A, and Muenke M. A previously unidentified amino-terminal domain regulates transcriptional activity of wild-type and disease-associated human GLI2 Human molecular genetics. 2005; 14(15): 2181-8.
50. Diaz Z, Mann K K, Marcoux S, Kourelis M, Colombo M, Komarnitsky P B, and Miller W H, Jr. A novel arsenical has antitumor activity toward As2O3-resistant and MRP1/ABCC1-overexpressing cell lines. Leukemia. 2008; 22(10):1853-63.
51. Kramann R, Tanaka M, and Humphreys B D. Fluorescence microangiography for quantitative assessment of peritubular capillary changes after AKI in mice. J Am Soc Nephrol. 2014; 25(9):1924-31.
52. Garnier N, Redstone G G, Dahabieh M S, Nichol J N, del Rincon S V, Gu Y, Bohle D S, Sun Y, Conklin D S, Mann K K, et al. The novel arsenical darinaparsin is transported by cystine importing systems. Molecular pharmacology. 2014; 85(4):576-85.
53. Garnier N, Petruccelli L A, Molina M F, Kourelis M, Kwan S, Diaz Z, Schipper H M, Gupta A, Rincon S D, Mann K K, et al. The novel arsenical Darinaparsin circumvents BRG1-dependent, HO-1-mediated cytoprotection in leukemic cells. Leukemia. 2013.
54. Machado A F, Hovland D N, Jr., Pilafas S, and Collins M D. Teratogenic response to arsenite during neurulation: relative sensitivities of C57BL/6J and SWV/Fnn mice and impact of the splotch allele. Toxicological sciences: an official journal of the Society of Toxicology. 1999; 51(1): 98-107.
55. DeSesso J M, Jacobson C F, Scialli A R, Farr C H, and Holson J F. An assessment of the developmental toxicity of inorganic arsenic. Reprod Toxicol. 1998; 12(4):385-433.
56. Chaineau E, Binet S, Pol D, Chatellier G, and Meininger V. Embryotoxic effects of sodium arsenite and sodium arsenate on mouse embryos in culture. Teratology. 1990; 41(1):105-12.
57. Riobo N A, and Manning D R. Pathways of signal transduction employed by vertebrate Hedgehogs. The Biochemical journal. 2007; 403(3):369-79.
58. Ribes V, Le Roux I, Rhinn M, Schuhbaur B, and Dolle P. Early mouse caudal development relies on crosstalk between retinoic acid, Shh and Fgf signalling pathways. Development. 2009; 136(4):665-76.
59. Hao K, Tian X D, Qin C F, Xie X H, and Yang Y M. Hedgehog signaling pathway regulates human pancreatic cancer cell proliferation and metastasis. Oncology reports. 2013; 29(3):1124-32.
60. Sasai K, Romer J T, Kimura H, Eberhart D E, Rice D S, and Curran T. Medulloblastomas derived from Cxcr6 mutant mice respond to treatment with a smoothened inhibitor. Cancer research. 2007; 67(8):3871-7.
61. Samarzija I, and Beard P. Hedgehog pathway regulators influence cervical cancer cell proliferation, survival and migration. Biochemical and biophysical research communications. 2012; 425(1):64-9.
62. Duman-Scheel M, Weng L, Xin S, and Du W. Hedgehog regulates cell growth and proliferation by inducing Cyclin D and Cyclin E. Nature. 2002; 417(6886):299-304.
63. Nagao H, Ijiri K, Hirotsu M, Ishidou Y, Yamamoto T, Nagano S, Takizawa T, Nakashima K, Komiya S, and Setoguchi T. Role of GLI2 in the growth of human osteosarcoma. The Journal of pathology. 2011; 224(2): 169-79.
64. Zhang D, Liu J, Wang Y, Chen J, and Chen T. shRNA-mediated silencing of Gli2 gene inhibits proliferation and sensitizes human hepatocellular carcinoma cells towards TRAIL-induced apoptosis. J Cell Biochem. 2011; 112 (11):3140-50.
65. Plaisant M, Giorgetti-Peraldi S, Gabrielson M, Loubat A, Dani C, and Peraldi P. Inhibition of hedgehog signaling decreases proliferation and clonogenicity of human mesenchymal stem cells. PLoS One. 2011; 6(2):e16798.
66. Lauth M, Bergstrom A, Shimokawa T, and Toftgard R. Inhibition of GLI-mediated transcription and tumor cell growth by small-molecule antagonists. Proc Natl Acad Sci USA. 2007; 104(20):8455-60.
67. Shi T, Mazumdar T, Devecchio J, Duan Z H, Agyeman A, Aziz M, and Houghton J A. cDNA microarray gene expression profiling of hedgehog signaling pathway inhibition in human colon cancer cells. PLoS One. 2010; 5(10).
68. Moshai E F, Wemeau-Stervinou L, Cigna N, Brayer S, Somme J M, Crestani B, and Mailleux A A. Targeting the hedgehog-glioma-associated oncogene homolog pathway inhibits bleomycin-induced lung fibrosis in mice. American journal of respiratory cell and molecular biology. 2014; 51(1):11-25.
69. Humphreys B D, Valerius M T, Kobayashi A, Mugford J W, Soeung S, Duffield J S, McMahon A P, and Bonventre J V. Intrinsic epithelial cells repair the kidney after injury. Cell stem cell. 2008; 2(3):284-91.
70. Lauth M, and Toftgard R. Non-canonical activation of GLI transcription factors: implications for targeted anti-cancer therapy. Cell Cycle. 2007; 6(20):2458-63.
71. Sasaki H, Nishizaki Y, Hui C, Nakafuku M, and Kondoh H. Regulation of Gli2 and Gli3 activities by an amino-terminal repression domain: implication of Gli2 and Gli3 as primary mediators of Shh signaling. Development. 1999; 126(17):3915-24.
72. Chiariello M, Gomez E, and Gutkind J S. Regulation of cyclin-dependent kinase (Cdk) 2 Thr-160 phosphorylation and activity by mitogen-activated protein kinase in late G1 phase. The Biochemical journal. 2000; 349 Pt 3(869-76.

What is claimed:

1. A method of treating kidney fibrosis in a subject, the method comprising:
   (a) diagnosing a subject as having early stage kidney fibrosis by detecting the presence of Gli1+ myofibroblast cells in a kidney sample obtained from the subject and,
   (b) administering to the subject an inhibitor of Gli2 activity, thereby treating early stage kidney fibrosis in the subject.

2. The method of claim 1, wherein the inhibitor of Gli2 activity also inhibits Gli1 and/or Gli3 activity.

3. The method of claim 1, wherein detecting the presence of Gli1+ cells comprises contacting a biological sample obtained from the subject with an agent that specifically binds Gli1.

4. The method of claim 1, wherein the inhibitor of Gli2 activity is an arsenic-based drug.

5. The method of claim 4, wherein the arsenic-based drug is darinaparsin.

6. The method of claim 1, wherein the inhibitor of Gli2 activity is GANT61.

7. The method of claim 1, wherein the subject is at risk of kidney fibrosis due to an injury to the kidney.

* * * * *

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
```

<223> OTHER INFORMATION: Description of Artificial Sequence: Synthetic
     primer

<400> SEQUENCE: 1
aggtcggtgt gaacggattt g                                              21

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 2
tgtagaccat gtagttgagg tca                                            23

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 3
ggagcacggg aaaagaaag                                                 19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 4
gagcccggag ctccttcaca                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 5
tgactggaag agcggagagt                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 6
gttcgggctg atgtaccagt                                                20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
atctggaccc ctcctgatag t                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcccagtgat tcagcaaag g                                                 21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgacagagg caccactgaa                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
catctccaga gtccagcaca                                                  20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
gcaggucucc uauccugaut t                                                21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: a, c, t, g, u, unknown or other

<400> SEQUENCE: 12

```
naucaggaua ggagaccugc tg                                                   22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
ggaaaacuuc aacaauacat t                                                    21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uguauuguug aaguuuucca g                                                    21
```